US012649730B2

(12) United States Patent
Kim et al.

(10) Patent No.: US 12,649,730 B2
(45) Date of Patent: Jun. 9, 2026

(54) CRYSTALLINE FORMS OF 5-[(1,1-DIOXIDO-4-THIOMORPHOLINYL) METHYL]-2-PHENYL-N-(TETRAHYDRO-2H-PYRAN-4-YL)-1H-INDOL-7-AMINE

(71) Applicant: MITOIMMUNE THERAPEUTICS INC., Seoul (KR)

(72) Inventors: Soon Ha Kim, Seoul (KR); Hye Kyung Chang, Seoul (KR); Hyoung Jin Kim, Seoul (KR); Sae Yeon Lee, Seoul (KR); Sang Kweon Jeon, Seoul (KR); Eun Kyung Yoo, Seoul (KR); Mooyoung Seo, Seoul (KR)

(73) Assignee: MITOIMMUNE THERAPEUTICS INC., Seoul (KR)

( * ) Notice: Subject to any disclaimer, the term of this patent is extended or adjusted under 35 U.S.C. 154(b) by 228 days.

(21) Appl. No.: 18/000,712

(22) PCT Filed: Apr. 11, 2022

(86) PCT No.: PCT/KR2022/005212

§ 371 (c)(1),
(2) Date: Dec. 5, 2022

(87) PCT Pub. No.: WO2022/220519

PCT Pub. Date: Oct. 20, 2022

(65) Prior Publication Data

US 2024/0043409 A1 Feb. 8, 2024

(30) Foreign Application Priority Data

Apr. 12, 2021 (KR) ........................ 10-2021-0047169

(51) Int. Cl.
*C07D 405/12* (2006.01)

(52) U.S. Cl.
CPC ........ *C07D 405/12* (2013.01); *C07B 2200/13* (2013.01)

(58) Field of Classification Search
CPC .. C07D 417/14; C07D 405/12; C07B 2200/13
See application file for complete search history.

(56) References Cited

U.S. PATENT DOCUMENTS

| | | | |
|---|---|---|---|
| 8,658,658 | B2 | 2/2014 | Su et al. |
| 2010/0291533 | A1 | 11/2010 | Kim et al. |
| 2016/0051558 | A1 | 2/2016 | Cho et al. |
| 2017/0035776 | A1 | 2/2017 | Kim et al. |
| 2017/0165272 | A1 | 6/2017 | Kim et al. |

FOREIGN PATENT DOCUMENTS

| | | | | |
|---|---|---|---|---|
| KR | 101098583 | B1 | 12/2011 | |
| KR | 101325272 | B1 | 11/2013 | |
| KR | 101513784 | B1 | 4/2015 | |
| KR | 101636563 | B1 | 7/2016 | |
| KR | 20160115827 | A | 10/2016 | |
| KR | 101852304 | B1 | 4/2018 | |
| KR | 101941004 | B1 | 1/2019 | |
| KR | 102006247 | B1 | 8/2019 | |
| WO | 2009025478 | A1 | 2/2009 | |
| WO | 2015111947 | A1 | 7/2015 | |
| WO | 2016072692 | A2 | 5/2016 | |
| WO | 2016153304 | A1 | 9/2016 | |
| WO | WO-2018034519 | A1 * | 2/2018 | ............ A61K 35/34 |

OTHER PUBLICATIONS

Coornaert et al. "Novel drug discovery strategies for atherosclerosis that target necrosis and necroptosis" Expert Opinion on Drug Discovery, 13(6):477-488 (2018).
English translation of International Search Report corresponding to International Patent Application No. PCT/KR2022/005212 (4 pages) (mailed Jul. 8, 2022).
Cao et al. "Endoplasmic Reticulum Stress and Oxidative Stress in Cell Fate Decision and Human Disease" Antioxidants & Redox Signaling, 21(3):396-413 (2014).
Cloonan et al. "Mitochondrial dysfunction in lung ageing and Disease" The European Respiratory Review, 29:200165 (2020).
Dubinin et al. "Duchenne muscular dystrophy is associated with the inhibition of calcium uniport in mitochondria and an increased sensitivity of the organelles to the calcium-induced permeability transition" BBA—Mol. Basis of Disease, 1866:165674 (2020).
Eirin et al. "Mitochondrial injury and dysfunction in hypertension-induced cardiac damage" European Heart Journal, 35:3258-3266 (2014).
Johns, Donald R. "Mitochondrial DNA and Disease" The New England Journal of Medicine, 333(10):638-644 (1995).
Khan et al. "Mitochondrial disorders: Challenges in diagnosis & treatment" Indian Journal of Medical Research, 141:13-26 (2015).
Li et al. "Mitochondrial dysfunction in fibrotic diseases" Cell Death Discovery, 6:80 (2020).
Madreiter-Sokolowski et al. "Interrelation between ROS and Ca2+ in aging and age-related diseases" Redox Biology, 36:101678 (2020).
Mattson et al. "Neuronal and glial calcium signaling in Alzheimer's disease" Cell Calcium, 34:385-397 (2003).
Suomalainen et al. "Mitochondrial diseases: the contribution of organelle stress responses to pathology" Nature Reviews Molecular Cell Biology, 19:77-92 (2018).

* cited by examiner

*Primary Examiner* — Brenda L Coleman
*Assistant Examiner* — Madeline E Braun
(74) *Attorney, Agent, or Firm* — Myers Bigel, P.A.

(57) ABSTRACT

The present invention relates to a Crystalline Form A of a compound of Chemical Formula 1 having physically and chemically outstanding characteristics compared to amorphous forms and other crystalline forms of the compound of Chemical Formula 1. Crystalline Form A of the compound of Chemical Formula 1 according to the present invention, compared to amorphous forms or other crystalline forms, does not denature even at prolonged exposure to harsh conditions, has low water sorption, is advantageous for formulation as the crystalline form does not change even under pressure or when pulverized, and the crystalline form itself has excellent stability, being useful for storage for extended periods.

6 Claims, 25 Drawing Sheets

Compound 1
Off white powder

Recrystallization 3g scale up product
White powder

Before recrystallization

After recrystallization 2g scale recrystallization product

MV = 70.50 µm STD = 56.34µm Duration: 0.12 Copt= 3.38

$D_5$ = 4.70 µm $D_{10}$ = 9.99 µm $D_{15}$ = 16.01 µm $D_{20}$ = 22.03 µm $D_{25}$ = 27.75 µm $D_{30}$ = 33.25 µm $D_{35}$ = 38.65 µm $D_{40}$ = 44.02 µm $D_{45}$ = 49.54 µm $D_{50}$ = 55.38 µm $D_{55}$ = 61.52 µm $D_{60}$ = 68.84 µm $D_{65}$ = 76.87 µm $D_{70}$ = 87.02 µm $D_{75}$ = 99.55 µm $D_{80}$ = 115.38 µm $D_{85}$ = 134.67 µm $D_{90}$ = 158.06 µm $D_{95}$ = 189.19 µm $D_{97}$ = 206.74 µm

| | Target % P/Po | Change In Mass (%) - ref Sorption | Desorption | Hysteresis |
|---|---|---|---|---|
| Cycle 1 | 0.0 | -0.0024 | -0.0024 | |
| | 10.0 | 0.0682 | 0.0641 | -0.0040 |
| | 20.0 | 0.1264 | 0.1039 | -0.0225 |
| | 30.0 | 0.1851 | 0.1451 | -0.0400 |
| | 40.0 | 0.2335 | 0.1824 | -0.0511 |
| | 50.0 | 0.2872 | | |
| | 60.0 | 0.3561 | | |
| | 70.0 | 0.4340 | | |
| | 80.0 | 0.5242 | | |
| | 90.0 | 0.6193 | | |
| | 95.0 | 0.7356 | | |
| Cycle 2 | 0.0 | 0.0301 | 0.0301 | |
| | 10.0 | 0.1009 | 0.1031 | 0.0022 |
| | 20.0 | 0.1536 | 0.1522 | -0.0015 |
| | 30.0 | 0.2019 | 0.2027 | 0.0008 |
| | 40.0 | 0.2569 | 0.2561 | -0.0008 |
| | 50.0 | | 0.3140 | |
| | 60.0 | | 0.3900 | |
| | 70.0 | | 0.4835 | |
| | 80.0 | | 0.5595 | |
| | 90.0 | | 0.6516 | |
| | 95.0 | | 0.7356 | |

CRYSTALLINE FORMS OF 5-[(1,1-DIOXIDO-4-THIOMORPHOLINYL) METHYL]-2-PHENYL-N-(TETRAHYDRO-2H-PYRAN-4-YL)-1H-INDOL-7-AMINE

TECHNICAL FIELD

The present invention relates novel Crystalline Forms of the compound of Chemical Formula 1 below, 5-[(1,1-dioxido-4-thiomorpholinyl)methyl]-2-phenyl-N-(tetrahydro-2H-pyran-4-yl)-1H-indol-7-amine.

[Chemical Formula 1]

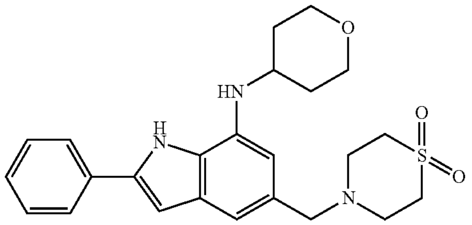

BACKGROUND ART

Various Crystalline Forms or amorphous forms may exhibit various solid state physical characteristics, such as moisture sorption, behavior in response to compression, stability during storage, and fluidity of milled solid. These properties in turn impact the suitability of certain solid states as active pharmaceutical ingredients for commercial manufacturing. For example, fluidity impacts the facility of handling of a substance during processing as a pharmaceutical product. If the particles of a powdered compound do not flow easily past each other, then a formulation expert should take this fact into consideration in developing tablet or capsule formulations, and such formulations may require use of lubricants such as colloidal silicon dioxide, talc, starch, or calcium phosphate tribasic.

Different Crystalline Forms or amorphous forms of the same drug may have substantial differences in pharmaceutically important properties, such as rate of dissolution and bioavailability. Rate of dissolution is not only a consideration in the preparation of syrups, elixirs and other liquid drugs but may also cause the results of therapy to differ. For example, the rate of dissolution of an active ingredient in the gastric juice of a patient affects to the rate at which an orally administered active ingredient can reach the patient's bloodstream, and thereby causes the outcome of therapy to differ.

Meanwhile, the compound of Chemical Formula 1, 5-[(1,1-dioxido-4-thiomorpholinyl)methyl]-2-phenyl-N-(tetrahydro-2H-pyran-4-yl)-1H-indol-7-amine is a compound disclosed through International Patent Publication WO2009-025478, and is a substance reported to exhibit preventive or therapeutic and ameliorative effects against cell necrosis and related disease.

The present inventors, in the process of developing products using the compound of Chemical Formula 1, have carried out continuous research into Crystalline Forms of Chemical Formula 1 which are convenient to manufacture and have excellent stability. As a result, the present inventors have confirmed that, among Crystalline Forms of the compound of Chemical Formula 1, Crystalline Form A has the most physically and chemically outstanding characteristics when compared to an amorphous form and other crystalline forms.

PRIOR ART LITERATURE

Patent Literature (Patent Literature 0001) International Patent Publication WO 2009-025478

DISCLOSURE

Technical Problem

A purpose of the present invention is to provide a Crystalline Form A of the compound of Chemical Formula 1, having physically and chemically outstanding properties compared to an amorphous form and other crystalline forms of the compound of Chemical Formula 1.

Another purpose of the present invention is to provide a method for preparing a Crystalline Form A of the compound of Chemical Formula 1.

Another purpose of the present invention is to provide a pharmaceutical composition comprising a Crystalline Form A of the compound of Chemical Formula 1 as an active ingredient.

Technical Solution

The present invention provides a Crystalline Form A of the compound of Chemical Formula 1, having physically and chemically outstanding properties compared to an amorphous form and other crystalline forms of the compound of Chemical Formula 1.

'Crystalline Form A' is a substance named crystalline Form XII in the crystalline form screening process of the compound of Formula 1 and was later renamed as 'Pattern A' or 'Crystalline Form A'. 'Crystalline Form A', 'pattern A' or 'Crystalline Form XII' are used interchangeably herein. According to X-ray powder diffraction (XRPD) analysis, Crystalline Form A has a crystalline structure different from that of other crystalline forms.

According to one example of the present invention, Crystalline Form A of the compound of Chemical Formula 1 is characterized in that it is identified with an X-ray powder diffraction pattern having at least 4, for example, 4, 5, 6, 7, 8, 9 or 10 diffraction peaks selected from 2[Θ] values 7.64±0.2, 12.32±0.2, 12.62±0.2, 15.26±0.2, 17.32±0.2, 19.18±0.2, 19.61±0.2, 19.95±0.2, 20.60±0.2, 21.12±0.2, 22.94±0.2, 24.11±0.2, and 28.15±0.2.

In particular, the X-ray powder diffraction pattern is characterized in that it has diffraction peaks at 2[Θ] values selected from among 7.64±0.2, 15.26±0.2, 17.32±0.2, 19.18±0.2, 21.12±0.2, and 22.94±0.2.

More specifically, Crystalline Form A of the compound of Chemical Formula 1 is characterized in that it is identified with an X-ray powder diffraction pattern whose peak positions coincide with the peak positions listed in Table 1 below.

TABLE 1

| 2-Theta(°) | Distance(Å) | Counts | Intensity % |
|---|---|---|---|
| 7.635 | 11.5699 | 1107 | 53.0 |
| 9.436 | 9.3652 | 101 | 4.8 |
| 11.653 | 7.5877 | 160 | 7.7 |
| 12.32 | 7.1787 | 518 | 24.8 |
| 12.62 | 7.0083 | 230 | 11.0 |
| 15.259 | 5.8018 | 1395 | 66.8 |
| 16.662 | 5.3164 | 79 | 3.8 |

TABLE 1-continued

| 2-Theta(°) | Distance(Å) | Counts | Intensity % |
|---|---|---|---|
| 17.316 | 5.1169 | 2089 | 100.0 |
| 17.631 | 5.0263 | 74 | 3.5 |
| 17.889 | 4.9542 | 68 | 3.3 |
| 18.816 | 4.7123 | 99 | 4.7 |
| 19.182 | 4.6231 | 672 | 32.2 |
| 19.613 | 4.5225 | 432 | 20.7 |
| 19.953 | 4.4461 | 532 | 25.5 |
| 20.596 | 4.3088 | 434 | 20.8 |
| 20.856 | 4.2556 | 182 | 8.7 |
| 21.121 | 4.2028 | 667 | 31.9 |
| 21.675 | 4.0967 | 129 | 6.2 |
| 22.753 | 3.9050 | 420 | 20.1 |
| 22.943 | 3.8731 | 1004 | 48.1 |
| 23.547 | 3.7751 | 159 | 7.6 |
| 24.108 | 3.6884 | 352 | 16.9 |
| 24.718 | 3.5988 | 141 | 6.7 |
| 25.342 | 3.5116 | 163 | 7.8 |
| 27.068 | 3.2915 | 59 | 2.8 |
| 28.146 | 3.1678 | 228 | 10.9 |
| 28.453 | 3.1344 | 81 | 3.9 |
| 28.992 | 3.0773 | 135 | 6.5 |
| 29.395 | 3.036 | 81 | 3.9 |
| 30.11 | 2.9655 | 64 | 3.1 |
| 30.721 | 2.9080 | 104 | 5.0 |

In another example, Crystalline Form A of the compound of Chemical Formula 1 provided by the present invention is characterized in that it has a melting point starting at 272.7° C. (±2.5) with a peak maximum at 273.4° C. (±2.5).

The present invention provides a method for preparing Crystalline Form A of a compound represented by Chemical Formula 1, the method comprising a step of stirring the compound of Chemical Formula 1 with a solution comprising a solvent selected from DMSO, DMF or NMP under heat for 1 to 24 hours; and a step of growing crystals by cooling the solution over 1 to 72 hours to 0 to 25° C. while stirring.

Here, the compound of Chemical Formula 1 used as a starting material may be an amorphous form or any Crystalline Form thereof.

Meanwhile, the heating may be carried out by raising the temperature to a range of 50 to 120° C.

Further, the cooling may be carried out at a rate of 5 to 20° C./h.

Another example of the present invention provides a method for preparing Crystalline Form A of a compound represented by Chemical Formula 1, the method comprising a step of crystallizing by adding an anti-solvent in a solution obtained by dissolving the compound of Chemical Formula 1 in a solvent; and a step of growing crystals by cooling the solution over 6 to 48 hours to 0 to 25° C. while stirring.

Likewise, here, the compound of Chemical Formula 1 used as a starting material may be an amorphous form or any Crystalline Form thereof.

In one example of the present invention, the method for preparing a Crystalline Form A of the compound of Chemical Formula 1 may additionally comprise, in the step of adding the anti-solvent, adding a Crystalline Form A of the compound of Chemical Formula 1 as a seed crystal.

As the solvent, any solvent may be used without limitation so long as the solvent is able to dissolve the compound of Chemical Formula 1. For example, the solvent may be selected from among DMSO, DMF and NMP, although it is not limited to these.

The anti-solvent is a solvent in which the target compound is insoluble or exhibits low solubility and may use to precipitate the target compound by adding the anti-solvent to a solution in which the compound is dissolved. Therefore, in the method for preparing Crystalline Form A according to the present invention, the compound may be crystallized by selecting and adding a suitable anti-solvent in consideration of the type of solvent in which the compound of Chemical Formula 1 is dissolved, solubility of the compound therein, and the like, and the crystal generated here may be one with an X-ray powder diffraction pattern and endothermic peaks.

In one example of the present invention, ethanol or MTBE may be used as the anti-solvent, but the anti-solvent is not limited to these.

In one example of the present invention, the weight of solvent compared to the weight of the compound of Chemical Formula 1 may be at least twice. Whereas there is no limit on the maximum amount of solvent used, as dissolving the compound of Chemical Formula 1 will suffice, but considering reaction economics, the solvent is preferably used within a range of 2 to 10 times the weight of the compound of Chemical Formula 1.

Meanwhile, the amount of anti-solvent used for crystallization is determined by the amount of solvent used. In one example of the present invention, the weight of anti-solvent compared to the weight of the solvent may be twice or more. Whereas there is no upper limit on the amount of anti-solvent used either, the weight or anti-solvent compared to solvent is preferably 2 to 15 times.

In the method for preparing Crystalline Form A of the compound of Chemical Formula 1, a filtering or drying step may be carried out after the method in order to remove impurities, excess solvent, etc. to obtain a product at high purity.

The present invention further provides a pharmaceutical composition comprising Crystalline Form A of the compound of Chemical Formula 1 and a pharmaceutically acceptable carrier.

In relation to the pharmaceutical composition comprising Crystalline Form A of the compound of Chemical Formula 1, identified uses of the compound of Chemical Formula 1 are as follow.

According to WO2009-025478, the compound of Chemical Formula 1 is reported to exhibit preventive, therapeutic and ameliorative effects against cell necrosis and associated diseases. According to WO2009-025478, cell necrosis and associated diseases are selected from the group comprised of acute/chronic hepatic disease (e.g. hepatitis, hepatic fibrosis, hepatocirrhosis), neurodegenerative disease (e.g. dementia, Parkinson's disease, Huntington's disease), ischemic cardiac disease, ischemic reperfusion injury (Korean Registered Patent 10-1325272), ischemic stroke or ischemic injury, pancreatitis, bacterial/viral sepsis, diabetes mellitus or diabetic complications, diabetic vascular disease [in particular, these diabetes are caused by pancreatic cell destroying substances, and mediated by virus, hyperglycemia, fatty acid, diet, toxin, streptozotocin and the like], necrotizing proctitis, cystic fibrosis, rheumatoid arthritis, degenerative arthritis, nephropathy, bacterial infection, viral infection (e.g. HIV), multiple sclerosis, leukemia, lymphoma, neonatal respiratory distress syndrome, asphyxia, tuberculosis, endometriosis, angiasthenia, psoriasis, chilblain, steroid treatment complications, gangrene, tenderness, hemoglobinuria, burns, hyperthermia, Crohn's disease, celiac disease, compartment syndrome, spinal cord injury, glomerulonephritis, muscular dystrophy, inherited metabolic disorder, mycoplasma disease, anthrax, Andersen's disease, congenital mitochondrial disease, phenylketonuria, placental infarction, syphilis, aseptic necrosis and the like In addition, necrosis and associated diseases caused by drugs and toxic substances are selected from the group consisting of the necrosis associated with alcoholism, the exposure to, and/or administration and/or self-administration of, cocaine, drugs (e.g., paracetamol), antibiotics, anti-cancer agent, Adriamycin, puromycin, bleomycin, NSAID, cyclosporine, chemical toxins (e.g., carbon tetrachloride, cyanide, methanol, ethylene glycol), poison gas, agrochemicals, heavy metals (e.g., lead, mercury, cadmium), or injury due to the exposure to radioactivity/UV and associated necrosis thereof.

Further, the compound of Chemical Formula 1 is additionally expected to exhibit preventive, therapeutic and improvement effects in necrosis and the associated diseases of acute/chronic kidney disease, traumatic brain damage, the neurogenerative disease of amyotrophic lateral sclerosis (ALS), necrotizing colitis, viral infection (e.g. SARS-CoV), skin disease including psoriasis and allergic dermatitis, and organ preservation/organ transplantation (see Korean Registered Patents 10-1098583 and 10-1941004).

Further, a pharmaceutical composition comprising the compound of Chemical Formula 1 is able to regulate intracellular calcium and is able to improve ER (Endoplasmic Reticulum) stress and mitochondrial malfunction due to abnormal intracellular calcium levels. Accordingly, a pharmaceutical composition comprising the compound of Chemical Formula 1 is expected to exhibit preventive or therapeutic and improvement effects with regard to illnesses associated with the same. Associated illnesses are as follow.

Inflammatory pulmonary disease including acute lung injury syndrome/acute pulmonary disease, pneumonia, tuberculosis, asthma, pulmonary hypertension, chronic obstructive pulmonary disease, idiopathic pulmonary fibrosis, and cystic fibrosis (See Mitochondrial dysfunction in fibrotic diseases. *Cell Death Discov.* 2020 Sep. 5; 6:80. Mitochondrial dysfunction in lung aging and diseases. *Eur Respir Rev.* 2020 Oct. 15; 29(157):200165, see Korean registered patent 10-1636563)

Demyelinating disease including demyelination and amyotrophic lateral sclerosis, hypertension including pulmonary hypertension, stroke, prion disease, epilepsy, ataxia, migraines, reduced cognitive skills, seizure, tremors, psychological illness (e.g., depression) (See Neuronal and glial calcium signaling in Alzheimer's disease. *Cell Calcium.* October-November 2003; 34(4-5):385-97. Mitochondrial disorders: challenges in diagnosis & treatment. *Indian J Med Res.* 2015 January; 141(1):13-26.)

Insulin resistance, hyperlipidemia, atherosclerosis, inflammatory bowel disease (IBD) including Crohn's Disease and ulcerative colitis, various cancers and metastasis of cancer (See reticulum stress and oxidative stress in cell fate decision and human disease. *Antioxid Redox Signal.* 2014 Jul. 20; 21(3):396-413.)

Visual impairment-associated disease (e.g., retinitis pigmentosa, optic neuropathy, cataract, glaucoma), anemia, cholestasis, hypoparathyroidism, pancytopenia, pancreatic disorder, lactic acidosis, lactacidemia, loss of hearing, short stature, intestinal obstruction, cardiac conduction defect, cardiomyopathy, endometriosis, infertility, early menopause (See Mitochondrial diseases: the contribution of organelle stress responses to pathology. *Nat Rev Mol Cell Biol.* 2018 February; 19(2):77-92. Seminars in medicine of the Beth Israel Hospital, Boston. Mitochondrial DNA and disease. *N Engl J Med.* 1995 Sep. 7; 333(10):638-44. Mitochondrial injury and dysfunction in hypertension-induced cardiac damage. *Eur Heart J.* 2014 Dec. 7; 35(46): 3258-3266.

Muscular atrophy diseases including limb gridle/Becker muscular dystrophy (LGMD/BMD) and Duchenne muscular dystrophy (DMD) (Duchenne muscular dystrophy is associated with the inhibition of calcium uniport in mitochondria and an increased sensitivity of the organelles to the calcium-induced permeability transition. See *Biochim Biophys Acta Mol Basis Dis.* 2020 May 1; 1866(5):165674.)

Aging and aging-related diseases (See Interrelation between ROS and $Ca^{2+}$ in aging and age-related diseases. *Redox Biology.* 2020; 6:101678.).

According to WO2009-025478, a pharmaceutical composition comprising the compound of Chemical Formula 1 exhibits not only liver protection and liver function improvement effects, but also preventive and therapeutic effects against acute and chronic liver conditions such as fatty liver, hepatic fibrosis, liver cirrhosis, and virus or drug-induced hepatitis. Further, as a result the pharmaceutical composition may prevent or treat liver disease complications such as portal hypertension but is not limited to such. Even further, the pharmaceutical composition according to the present invention is effective in preventing and treating liver disease selected from among liver transplant, alcoholic or non-alcoholic fatty liver (See Korean Registered Patent 10-2006247), hepatic fibrosis, liver cirrhosis, and virus or drug-induced hepatitis, and is effective against acute and chronic alcoholic liver disease. Further, the composition according to the present invention is effective in treating or preventing fatty liver caused by fatty acids or acute or chronic liver disease caused by fatty liver.

According to Korean Registered Patent No. 10-1852304, the compound of Chemical Formula 1 may be used in a stem cell culturing step to improve the differentiation efficiency and maturity of stem cell-derived cardiomyocytes.

Therefore, the present invention further provides a composition comprising Crystalline Form A of the compound of Chemical Formula 1 for inducing differentiation of stem cells into cardiomyocytes.

Further, according to WO2016-072692, the compound of Chemical Formula 1 may be used to prevent and treat mucositis.

Accordingly, the present invention provides the use of a pharmaceutical composition comprising Crystalline Form A of a compound of Formula 1 and a pharmaceutically acceptable carrier for the prevention or treatment of the diseases listed above, and a method for preventing or treating the diseases listed above comprising administering the pharmaceutical composition to a subject in need thereof. In the present invention, "treatment" means the interrupting or delaying the progress of the disease when applied to the subject showing the onset of disease symptoms, and "prevention" means the interrupting or delaying the sign of the onset of disease when applied to the subject that does not show, but is at risk of, the onset of disease symptoms.

In the present invention, "pharmaceutical composition" may comprise pharmaceutically acceptable carriers, together with the compounds of the present invention.

The compound of Chemical Formula 1 according to the present invention may be administered in various oral and non-oral dosage forms for clinical administration, and when formulated, is prepared using diluents or excipients such as commonly used fillers, bulking agents, binding agents, wetting agents, disintegrating agents, or surfactants.

Solid formulations for oral administration include tablets, pills, powders, granules, capsules and troches, and such solid formulations are prepared by mixing at least one of the compounds of the present invention with at least one excipient, for example, starch, calcium carbonate, sucrose, lactose, or gelatin. Further, in addition to simple excipients, lubricating agents such as magnesium stearate, or talc is used. Liquid formulations for oral administration include suspensions, liquids for internal use, emulsions, or syrups, and in addition to the commonly used simple diluents water and liquid paraffin, various excipients, for example wetting agents, sweeteners, aromatics, and preservatives may be included.

Formulations for non-oral administration include sterile aqueous solutions, non-aqueous solvents, suspensions, emulsions, lyophilized preparations, suppositories. As the non-aqueous solvent and the suspension solvent, propylene glycol, polyethylene glycol, vegetable oil such as olive oil, injectable ester such as ethyl oleate, and the like can be used. As the base of the suppository, witepsol, macrogol, tween 61, cacao butter, laurin butter, glycerol, gelatin and the like can be used.

Further, the effective human dose for the compound of Chemical Formula 1 according to the present invention may vary depending on the age, body weight, sex, mode of administration, health status and severity of illness of the patients, and is normally approximately 0.001-100 mg/kg/day, preferably 0.01-35 mg/kg/day. For an adult patient with a body weight of 70 kg, it is normally 0.07-7000 mg/day, preferably 0.7-2500 mg/day, and depending on the judgment of a physician or pharmacist it may be administered once a day or divisionally across multiple administrations at certain time intervals.

Effects of Invention

Crystalline Form A of the compound of Chemical Formula 1 according to the present invention, compared to amorphous forms or other crystalline forms, does not denature even at prolonged exposure to harsh conditions, has low water sorption, is advantageous for formulation as the crystalline form does not change even under pressure or when pulverized, and the crystalline form itself has excellent stability, being useful for storage for extended periods.

BEST MODE(S) FOR CARRYING OUT THE INVENTION

Figure 1:
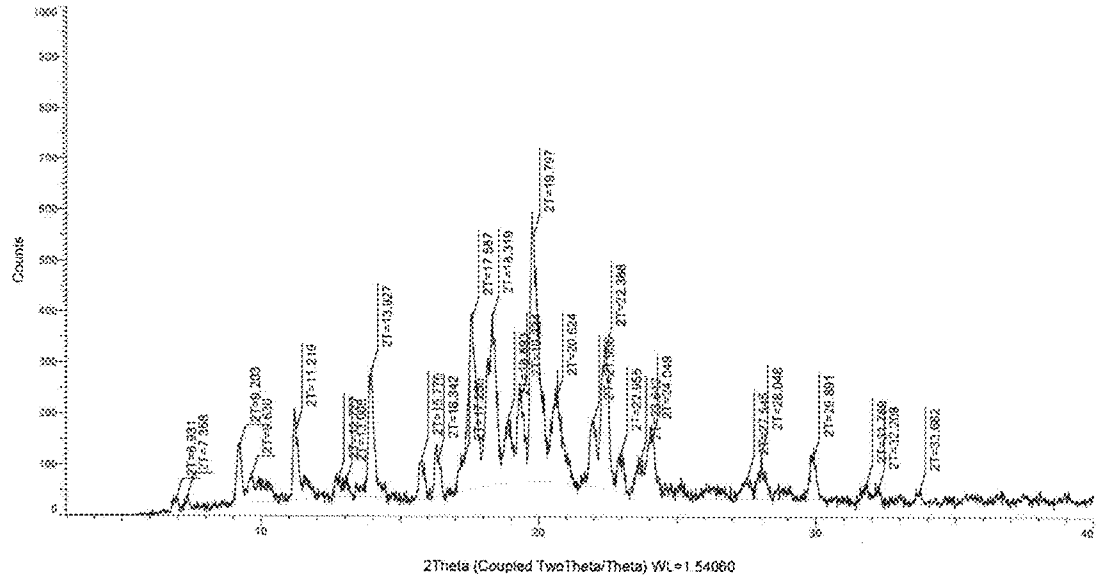
FIG. 1 shows X-ray powder diffraction pattern (XRPD) analysis results for P9 prior to purification.

The advantages and characteristics of the present invention, and method for achieving the same, shall become evident with reference to the embodiments which are described in detail in the following. However, the present invention is not limited to the embodiments disclosed in the following and may be realized in various forms. The present embodiments are solely intended to complete the disclosure of the present invention, and to inform persons having ordinary skill in the art of the full scope of the invention; the present invention is defined solely by the appended claims.

EXAMPLES

Abbreviations

The following abbreviations are used in the present application.

| | |
|---|---|
| MeOH | Methanol |
| EtOH | Ethanol |
| DMSO | Dimethyl sulfoxide |
| NMP | N-methylpyrrolidone |
| DMF | N,N-dimethylformamide |
| MTBE | Methyl t-butyl ether |
| MIBK | Methyl isobutyl ketone |
| ACN | Acetonitrile |
| MEK | Methyl ethyl ketone |
| EtOAc | Ethyl acetate |
| IPA | Isopropanol |
| TGA/DSC | Thermogravimetric analysis/differential scanning calorimetry |
| RH | Relative humidity |
| RPM | Revolutions per minute |

Equipment, Standards and Methodologies Used

1. X-Ray Powder Diffraction (XRPD)

Measurements were carried out using a Bruker D8 Advance power diffractometer. X-ray diffraction patterns were measured rotating the specimen between 3° and 40° using Cu K-alpha X-rays (1=1.54179 Å) (40 kV/40 mA).

Rate of specimen rotation=15 RPM

Scanning rate=18.5°/min

2. Differential Scanning Calorimetry (DSC)

Measurements were taken Using TA DSC Q2000 and Discovery DSC-2500 placing approximately 1 mg specimen in a hermetic aluminum pan with a pinhole and heating from 25° C. to 300° C. at a rate of 10° C./min.

3. Thermal Gravimetric Analysis (TGA)

TGA Q50 or TA Q5000 was used, and measurements were carried out by placing approximately 4 mg specimen in an open platinum pan and heating from 30° C. to 300° C. at a rate of 10° C./min.

4. Particle Size Distribution Analysis (PSD)

Measurements were carried out using a Sympatec HELOS particles size analyzer in a dispersing system using RODOS under 0.5 bar pressure.

5. Polarized Light Microscopy (PLM)

A 5-megapixel CCD Nikon LV100POL microscope having a 20× magnification physical lens.

6. Water Sorption and Desorption Study, DVS Cycle

Using SMS DVS Advantage 1, 10 mg sample was placed in a mesh stainless steel basket. The overall test cycle comprises scanning two times (sorption and desorption) at 10% RH intervals in a 40 to 90% range (60 to 360 minutes for each humidity level) at a constant temperature (25° C.).

Example 1: Preparation of 5-[(1,1-dioxido-4-thiomorpholinyl)methyl]-2-phenyl-N-(tetrahydro-2H-pyran-4-yl)-1H-indol-7-amine

[Reaction Scheme 1]

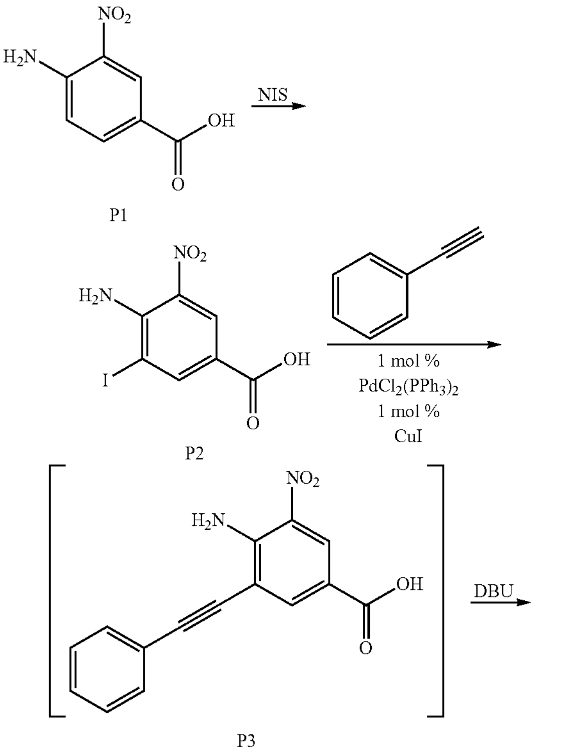

P1

P2

P3

-continued

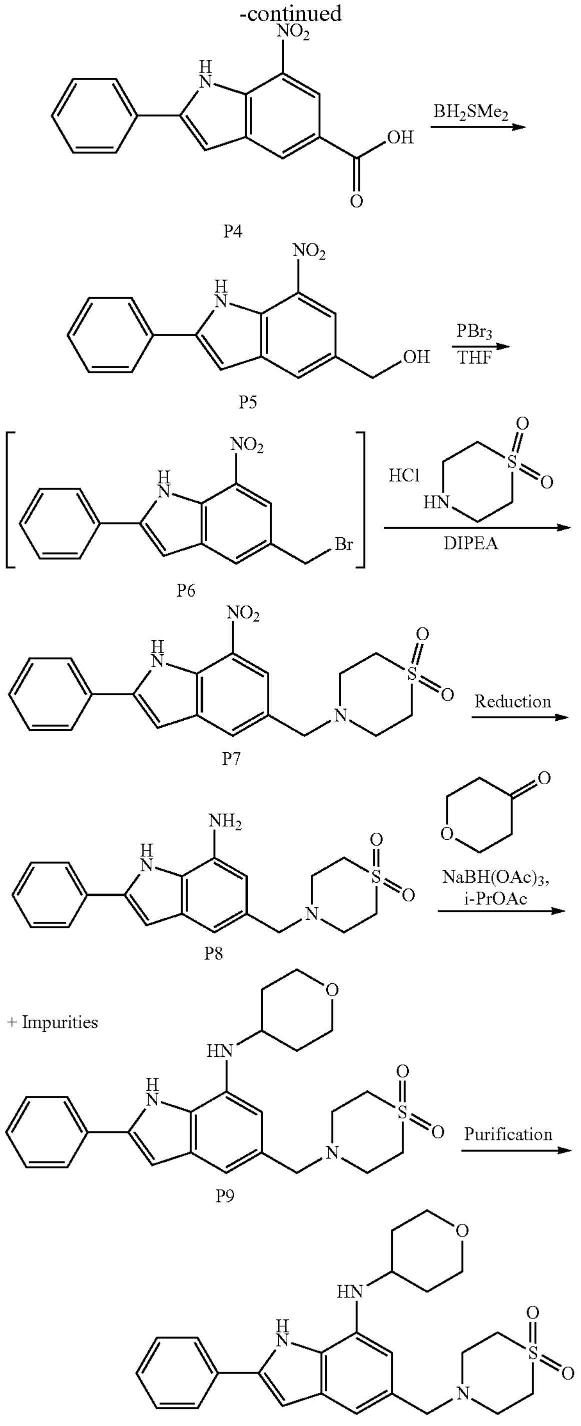

compound 1

The method for preparing the compound of Chemical Formula 1 disclosed in WO2009-025478 is as shown in Reaction Scheme 1 above.

P9 prepared in accordance with Reaction Scheme 1 includes a large amount of impurities and foreign materials. The compound of Chemical Formula 1 has very low solubility, and purification was therefore a very important step. To remove color and foreign materials from the P9 initially obtained for research was dissolved in DMSO then filtered, and EtOH was added as anti-solvent to yield a purified compound named the compound of Chemical Formula 1.

Figure 2:
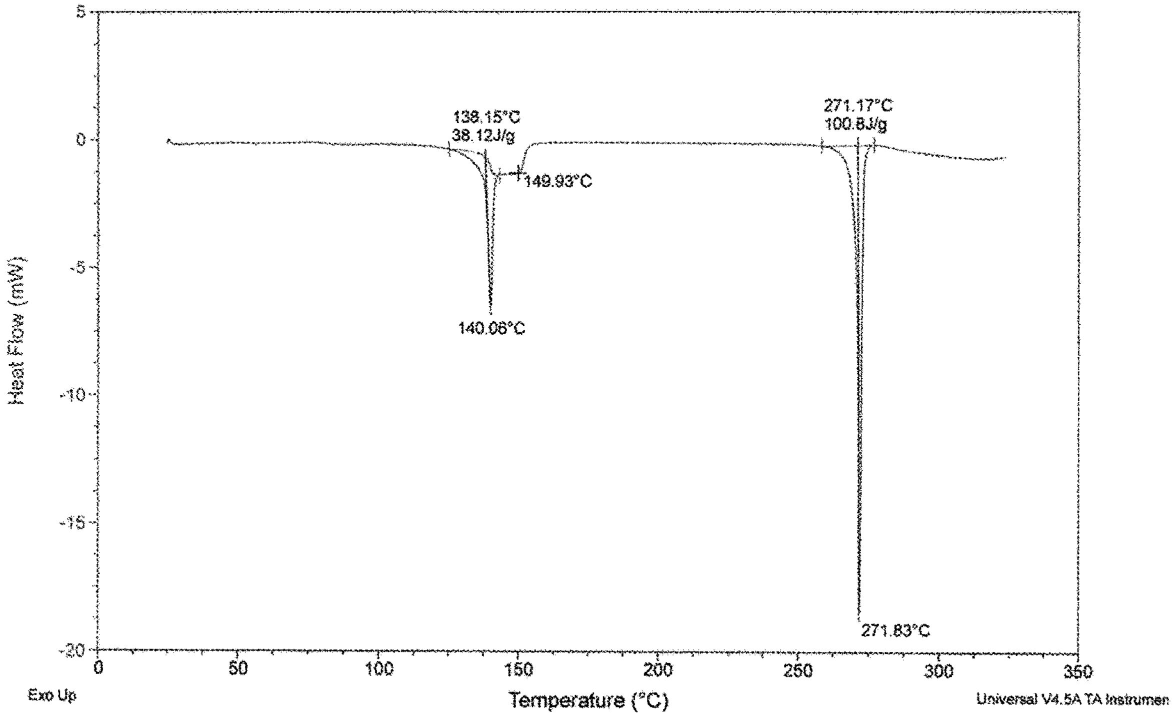
FIG. 2 shows differential scanning calorimetry (DSC) results for P9 prior to purification.
Figure 3:
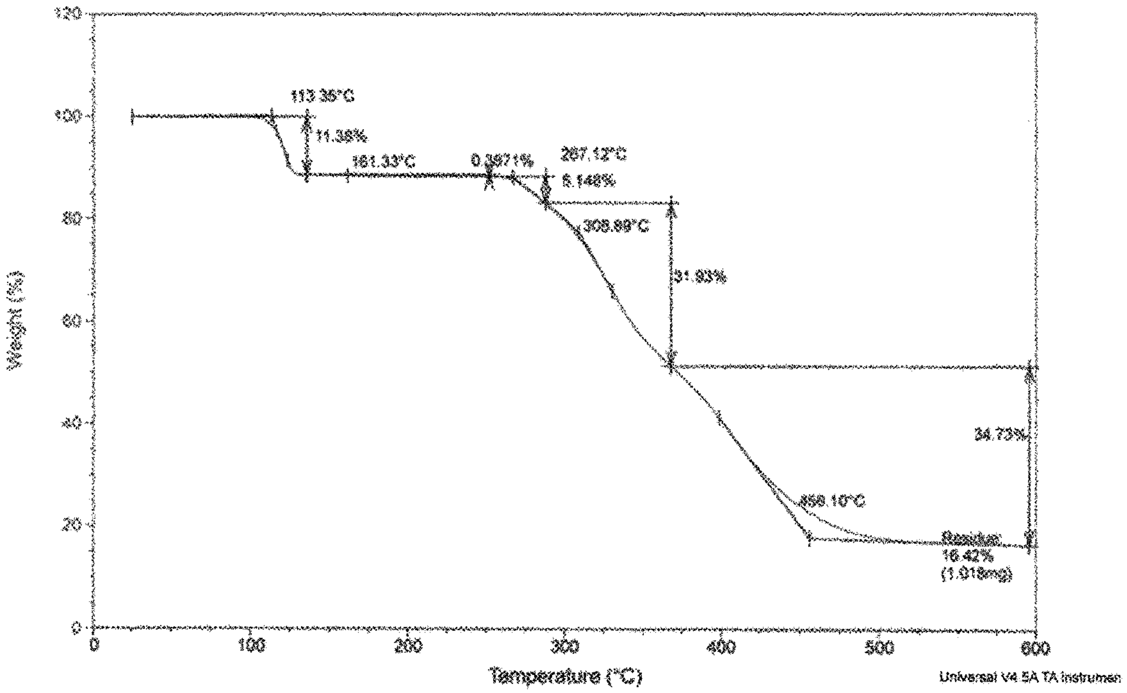
FIG. 3 shows thermal gravimetric analysis (TGA) results for P9 prior to purification.

FIG. 1 and Table 2 show X-ray powder diffraction pattern (XRPD) analysis results for P9 prior to purification. FIG. 2 shows differential scanning calorimetry (DSC) results for P9 prior to purification, and FIG. 3 shows thermal gravimetric analysis (TGA) results for P9 prior to purification.

P9 was identified as Crystalline Form V according to results of later experiments. 11.4% mass reduction was observed at up to 160° C., with a melting point of 271° C.

TABLE 2

List of characteristic XRPD peaks of P9 (Crystalline Form V)

| 2-Theta(°) | Distance(Å) | Counts | Intensity % |
|---|---|---|---|
| 6.931 | 12.74359 | 22.4 | 4.7 |
| 7.358 | 12.00503 | 30.2 | 6.3 |
| 9.203 | 9.60138 | 112 | 23.3 |
| 9.630 | 9.17694 | 49.5 | 10.3 |
| 11.219 | 7.88062 | 134 | 27.8 |
| 12.727 | 6.94995 | 29.7 | 6.2 |
| 13.008 | 6.80032 | 23.6 | 4.9 |
| 13.927 | 6.35345 | 245 | 51.0 |
| 15.776 | 5.61291 | 78.2 | 16.2 |
| 16.342 | 5.41964 | 67.7 | 14.1 |
| 17.256 | 5.13477 | 52.9 | 11.0 |
| 17.587 | 5.03886 | 333 | 69.3 |
| 18.319 | 4.83894 | 329 | 68.4 |
| 18.893 | 4.69343 | 126 | 26.1 |
| 19.334 | 4.58729 | 162 | 33.6 |
| 19.797 | 4.48093 | 481 | 100.00 |
| 20.624 | 4.30307 | 162 | 33.6 |
| 21.956 | 4.04498 | 125 | 25.9 |
| 22.388 | 3.96797 | 271 | 56.3 |
| 22.955 | 3.87117 | 73.2 | 15.2 |
| 23.642 | 3.76027 | 61.3 | 12.7 |
| 24.049 | 3.69749 | 102 | 21.1 |
| 27.545 | 3.23567 | 40.1 | 8.3 |
| 28.046 | 3.17899 | 86.8 | 18.0 |
| 29.891 | 2.98685 | 75.3 | 15.6 |
| 31.789 | 2.81269 | 32.4 | 6.7 |
| 32.209 | 2.77699 | 19.6 | 4.1 |
| 33.682 | 2.65879 | 17.7 | 3.7 |

To reduce or remove residual DMSO, color and impurities, etc. in the purified substance (P9), a second heating/slurrifying purification step using EtOH was carried out to obtain a solid which was named the compound of Chemical Formula 1. Crystalline forms IV, V, VIII, XI, XII and others were further identified depending on the concentrations, temperature, or duration of the process.

For mass production of highly pure and stable clinical substances at a GMP facility, establishing optimized and standardized purification conditions and conditions for preparing the most stable crystalline form are very important. Accordingly, the compound of Chemical Formula 1 prepared for research purposes was used for purification studies and study of multiple crystalline forms.

Example 2: Screening of Solvents for Purification

The solubility of the compound of Chemical Formula 1 was screened to find a suitable solvent for obtaining the compound of Chemical Formula 1 without foreign materials or color and having the most stable crystalline form. Specifically, solubility and purity of the compound of Chemical Formula 1 were analyzed for various solvents using supernatant at 25° C. and 50° C.

TABLE 3

Solubility of the compound of Chemical Formula 1 in various solvents at 25° C. and 50° C.

| | Solubility (mg/mL) | | Purity (TRS, %) | |
|---|---|---|---|---|
| Solvents | 25° C. | 50° C. | 25° C. | 50° C. |
| MeOH | 0.59 | 1.15 | 2.33 | 3.64 |
| EtOH | 1.41 | 1.08 | 2.06 | 2.42 |
| IPA | 0.32 | 0.54 | 2.21 | 3.65 |
| 1-Butanol | 0.65 | 1.00 | 5.52 | 4.89 |
| ACN | 3.09 | 4.04 | 3.26 | 4.86 |
| Acetone | 5.29 | 17.50 | 9.83 | 2.82 |
| MEK | 6.08 | 8.12 | 11.78 | 9.24 |
| MIBK | 2.10 | 2.82 | 65.92 | 58.06 |
| EtOAc | 1.36 | 1.86 | 3.74 | 2.98 |
| iPrOAc | 0.71 | 0.91 | 4.49 | 3.36 |
| MTBE | 0.06 | 0.07 | 19.33* | 11.87* |
| DMF | 206.03 | 332.99 | 4.05 | 1.85 |
| THF | 17.40 | 16.26 | 4.81 | 4.62 |
| 2-MeTHF | 2.78 | 3.41 | 8.16 | 9.74 |
| NMP | 160.03 | 192.42 | 4.92 | 4.84 |
| DMSO | 43.35 | 238.15 | 9.49 | 6.92 |
| $CHCl_3$ | 4.70 | 4.62 | 3.34 | 5.14 |
| Toluene | 0.02 | 0.02 | 41.21* | 46.12* |
| Heptane | <LOQ | <LOQ | <LOQ | <LOQ |
| Water | 0.001 | 0.046 | 59.06* | 0.83 |
| MeOH/$H_2O$ = 1:1(v/v) | 0.03 | 0.08 | 23.04* | 20.52* |
| Acetone-$H_2O$ (1:2) | 0.08 | 0.16 | 23.27* | 21.68* |
| Acetic acid-$H_2O$ (1:1) | 52.77 | 75.61 | 10.83 | 28.75 |

TRS (total related substance) = 100% − purity % (DS dissolved in organic solvent analyzed with HPLC)
*Purity reduced due to relatively low concentration in HPLC assay As can be seen in Table 3, solubility of the compound of Chemical Formula 1 is very low in most solvents, and the solvents exhibiting solubility of 40 mg/mL or higher were DMF, NMP and DMSO. However, DMF, NMP and DMSO also have high solubility for impurities, and it was thought that a recrystallization study using anti-solvent was suitable as a purification study. As the anti-solvent, priority consideration was given to MeOH, EtOH, IPA or EtOAc, which have low total related substance (TRS) content.

Carrying out purification and polymorphs studies based on the above results, it was discovered by the compound of Chemical Formula 1 has various crystalline forms, and the process is described in Example 3.

Example 3: Preparation of Crystalline Forms

Example 3-1: Crystalline Form IV—Slurry Method (DMF Solvate)

600 mg of the compound of Chemical Formula 1 was placed in 4 mL DMF and agitated for one day at 25° C. The supernatant was removed using an ultracentrifuge, and the remaining solid was vacuum dried to obtain crystals. This was named Crystalline Form IV of the compound of Chemical Formula 1, and XRPD, DSC/TGA and $^1$H NMR were measured.

TABLE 4

List of characteristic XRPD peaks of Crystalline Form IV

| 2-Theta(°) | Distance(Å) | Counts | Intensity % |
|---|---|---|---|
| 8.519 | 10.3703 | 1173 | 11.6 |
| 9.495 | 9.3070 | 111 | 1.1 |
| 10.499 | 8.4189 | 307 | 3.0 |
| 13.581 | 6.5146 | 177 | 1.8 |
| 15.438 | 5.7349 | 295 | 2.9 |
| 16.484 | 5.3732 | 265 | 2.6 |
| 17.060 | 5.1930 | 10069 | 100.0 |
| 18.013 | 4.9204 | 267 | 2.7 |
| 19.016 | 4.6630 | 103 | 1.0 |
| 21.118 | 4.2034 | 1389 | 13.8 |
| 21.757 | 4.0814 | 668 | 6.6 |
| 22.245 | 3.9929 | 400 | 4.0 |
| 22.565 | 3.9370 | 67 | 0.7 |
| 23.189 | 3.8325 | 94 | 0.9 |
| 23.367 | 3.8038 | 64 | 0.6 |
| 23.915 | 3.7178 | 55 | 0.5 |
| 24.184 | 3.6771 | 832 | 8.3 |
| 24.345 | 3.6530 | 400 | 4.0 |
| 25.104 | 3.5444 | 150 | 1.5 |
| 27.331 | 3.2605 | 150 | 1.5 |
| 28.274 | 3.1538 | 418 | 4.2 |
| 28.966 | 3.0800 | 53 | 0.5 |
| 29.207 | 3.0551 | 163 | 1.6 |
| 29.581 | 3.0173 | 130 | 1.3 |
| 30.008 | 2.9754 | 314 | 3.1 |
| 31.785 | 2.8130 | 74 | 0.7 |
| 33.991 | 2.6353 | 80 | 0.8 |
| 34.466 | 2.6000 | 271 | 2.7 |
| 36.039 | 2.4901 | 110 | 1.1 |
| 38.076 | 2.3614 | 57 | 0.6 |

Figure 4:
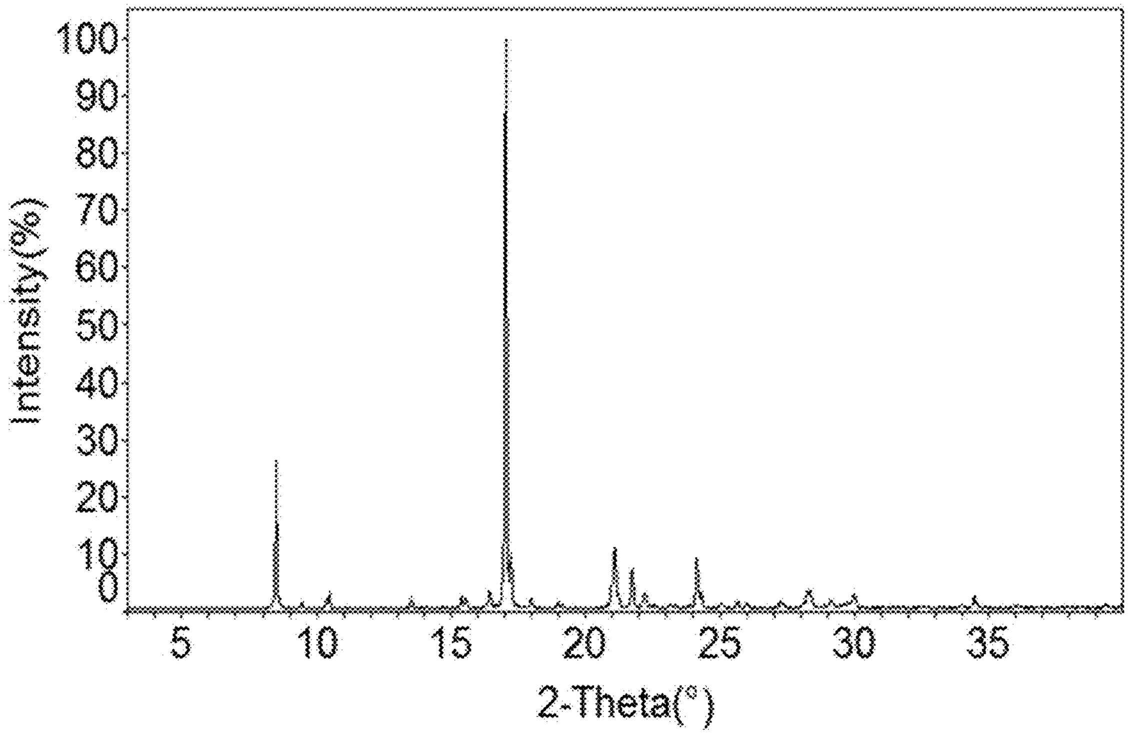
FIG. 4 shows X-ray powder diffraction pattern (XRPD) analysis results for Crystalline Form IV.

FIG. 4 and Table 4 show X-ray powder diffraction pattern (XRPD) analysis results for Crystalline Form IV.

The form of Crystalline Form IV is characterized in that it is identified using a X-ray powder diffraction pattern having at least four diffraction peaks at 2[Θ] values selected from 8.52±0.2, 17.06±0.2, 21.12±0.2, 21.76±0.2, 24.18±0.2, 24.35±0.2 and 28.27±0.2.

Figure 5:
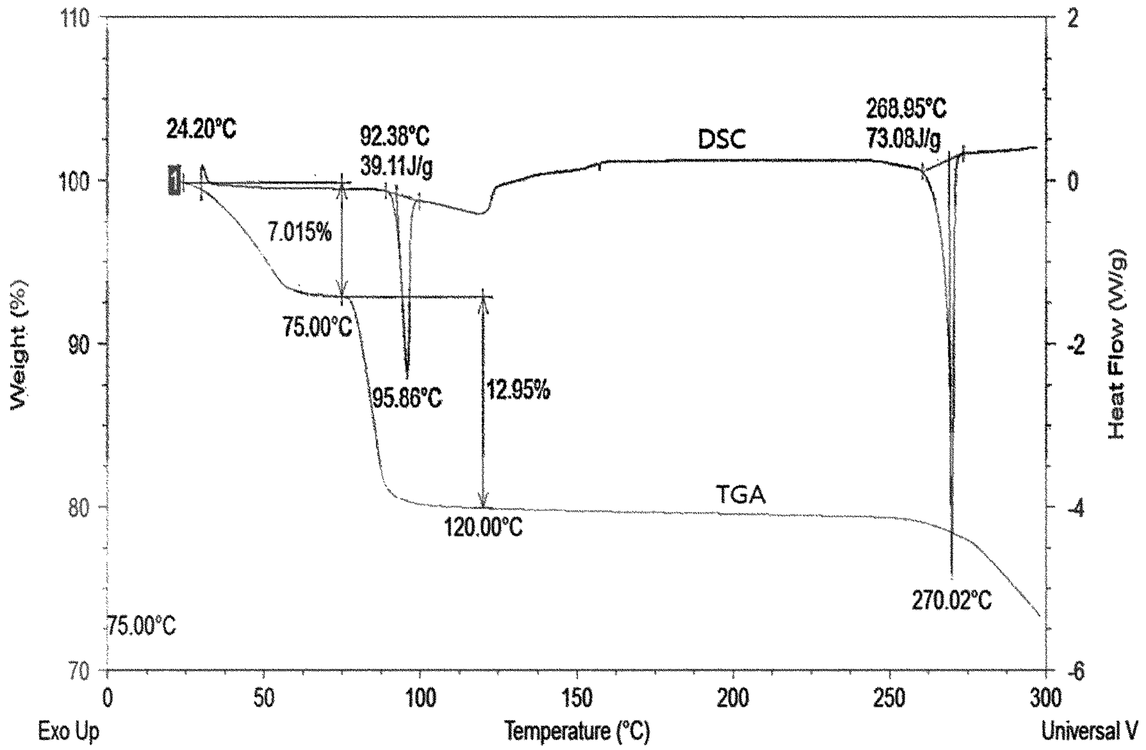
FIG. 5 shows TGA/DSC overlay results for Crystalline Form IV.

FIG. 5 shows TGA/DSC overlay results for Crystalline Form IV.

Meanwhile, $^1$H NMR results were as follow.

$^1$H NMR (400 MHz, DMSO-d6) δ ppm 1.41-1.54 (m, 1H), 2.06 (br d, J=11.29 Hz, 2H), 2.74 (s, 3H, DMF), 2.89 (s, 7H), 3.09 (br d, J=4.77 Hz, 4H), 3.46-3.56 (m, 2H), 3.59-3.71 (m, 3H), 3.90-4.00 (m, 2H), 5.35 (d, J=7.78 Hz, 1H), 6.32 (s, 1H), 6.76 (s, 2H), 7.27-7.35 (m, 1H), 7.48 (t, J=7.65 Hz, 2H), 7.80 (d, J=7.28 Hz, 2H), 7.96 (s, 1H, DMF), 10.94 (s, 1H).

Based on XRPD, DSC/TGA and $^1$H NMR results, Crystalline Form IV is a DMF solvate (the compound of Chemical Formula 1: DMSO=1:1).

Figure 6:
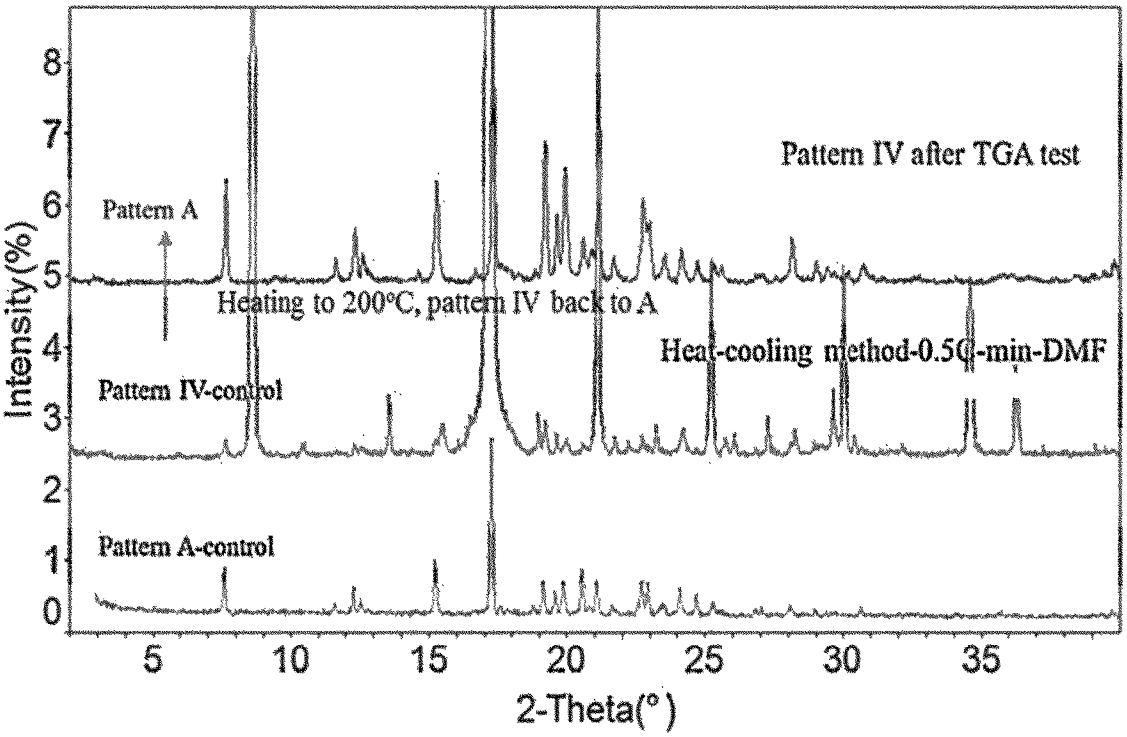
FIG. 6 shows XRPD results measured after TGA testing of Crystalline Form IV.

Meanwhile, FIG. 6 shows XRPD results measured after TGA testing (heating to 200° C. then cooling) of Crystalline Form IV. In the XRPD results of FIG. 6, when Crystalline Form IV is heated to 200° C. then chilled, DMF was removed, and another crystalline form was observed. This was named Crystalline Form XII (later, renamed as "pattern A" or Crystalline A").

Figure 7:
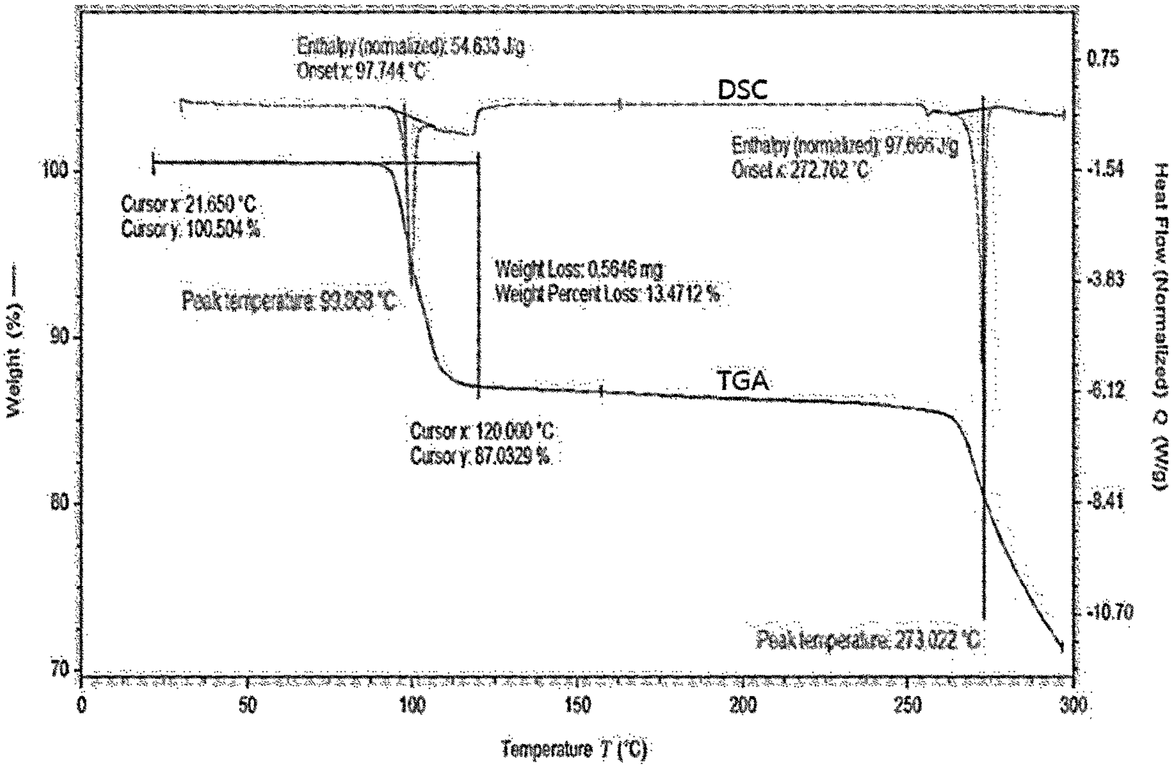
FIG. 7 shows TGA/DSC overlay results for Crystalline Form IV.

Example 3-2: Crystalline Form IV (DMF Solvate)—Recrystallization 200 mg of the compound of Chemical Formula 1 was placed in 0.4 mL DMF and heated to 50° C. The suspension obtained was filtered at 50° C., and the solution obtained was chilled to 0° C. at a rate of 0.5° C./min to obtain a solid which was vacuum dried to obtain a crystalline form. In TGA and DSC analysis of the obtained crystalline form, as seen in FIG. 7, the TGA/DSC overlay results of Crystalline Form IV identical to that of FIG. 5 were observed, confirming that the crystalline form was Crystalline Form IV (the compound of Chemical Formula 1: DMSO=1:1).

Example 3-3: Crystalline Form V (Metastable)—Solvent/Anti-Solvent 600 mg of the compound of Chemical Formula 1 was placed in 2 mL DMSO, and to the supernatant (1.5 mL) obtained from the suspension using a centrifuge (1.5 mL), EtOH in an amount seven times that of DMSO (10.5 mL) was slowly added at room temperature over 1 hour (agitating at 700 RPM). The solid obtained using a centrifuge was vacuum dried to obtain a crystal. This was named Crystalline Form V of the compound of Chemical Formula 1, and XRPD, DSC/TGA and $^{1}$H NMR were measured.

TABLE 5

List of characteristic XRPD peaks of Crystalline Form V

| 2-Theta(°) | Distance(Å) | Counts | Intensity % |
|---|---|---|---|
| 2.247 | 39.28 | 121 | 1.3 |
| 6.817 | 12.9562 | 2284 | 24.8 |
| 9.116 | 9.6929 | 478 | 5.2 |
| 9.517 | 9.2851 | 278 | 3.0 |
| 11.135 | 7.9392 | 109 | 1.2 |
| 12.989 | 6.81 | 82 | 0.9 |
| 13.837 | 6.3944 | 2089 | 22.7 |
| 16.246 | 5.4513 | 128 | 1.4 |
| 17.372 | 5.1005 | 899 | 9.8 |
| 18.058 | 4.9084 | 154 | 1.7 |
| 18.268 | 4.8524 | 902 | 9.8 |
| 18.669 | 4.749 | 201 | 2.2 |
| 19.084 | 4.6468 | 5081 | 55.2 |
| 19.661 | 4.5115 | 5264 | 57.2 |
| 19.953 | 4.4461 | 161 | 1.7 |
| 20.512 | 4.3264 | 9207 | 100.0 |
| 22.262 | 3.99 | 279 | 3.0 |
| 22.84 | 3.8903 | 945 | 10.3 |
| 23.903 | 3.7197 | 156 | 1.7 |
| 26.112 | 3.4098 | 120 | 1.3 |
| 27.452 | 3.2464 | 569 | 6.2 |
| 27.849 | 3.2009 | 400 | 4.3 |
| 28.778 | 3.0997 | 1268 | 13.8 |
| 33.582 | 2.6665 | 74 | 0.8 |
| 34.497 | 2.5977 | 556 | 6.0 |
| 38.689 | 2.3254 | 1161 | 12.6 |

Figure 8:
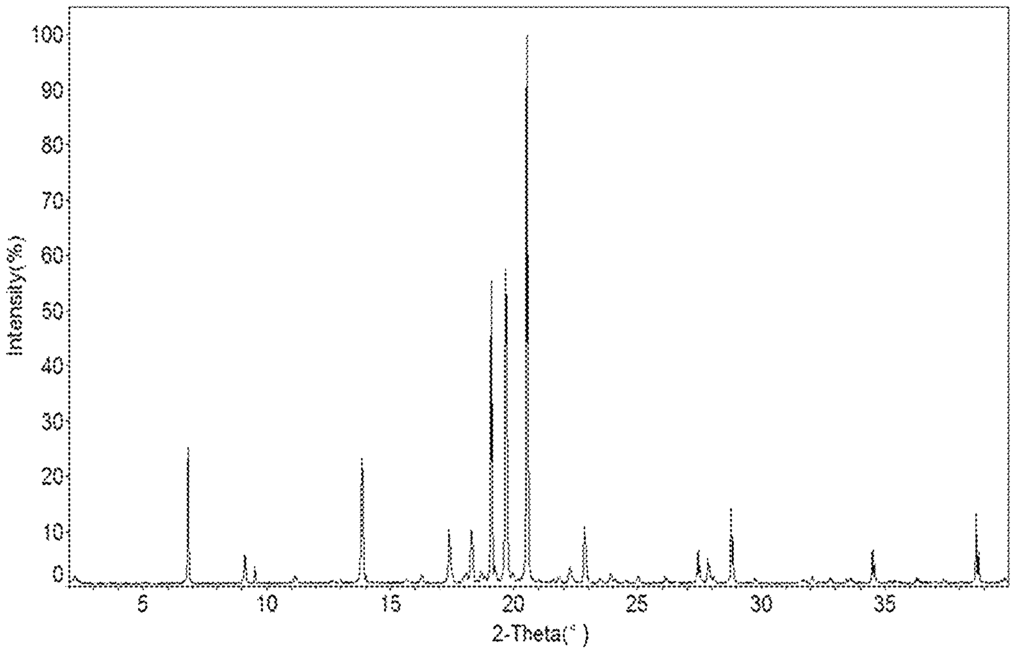
FIG. 8 shows X-ray powder diffraction pattern (XRPD) analysis results for Crystalline Form V.

FIG. 8 and Table 5 shows X-ray powder diffraction pattern (XRPD) analysis results for Crystalline Form V.

The form of Crystalline Form V is characterized in that it is identified using a X-ray powder diffraction pattern having at least four diffraction peaks at 2[Θ] values selected from 6.82±0.2, 13.84±0.2, 19.08±0.2, 19.66±0.2, 20.51±0.2, 22.84±0.2, 23.78±0.2, and 38.69±0.2.

Figure 9:
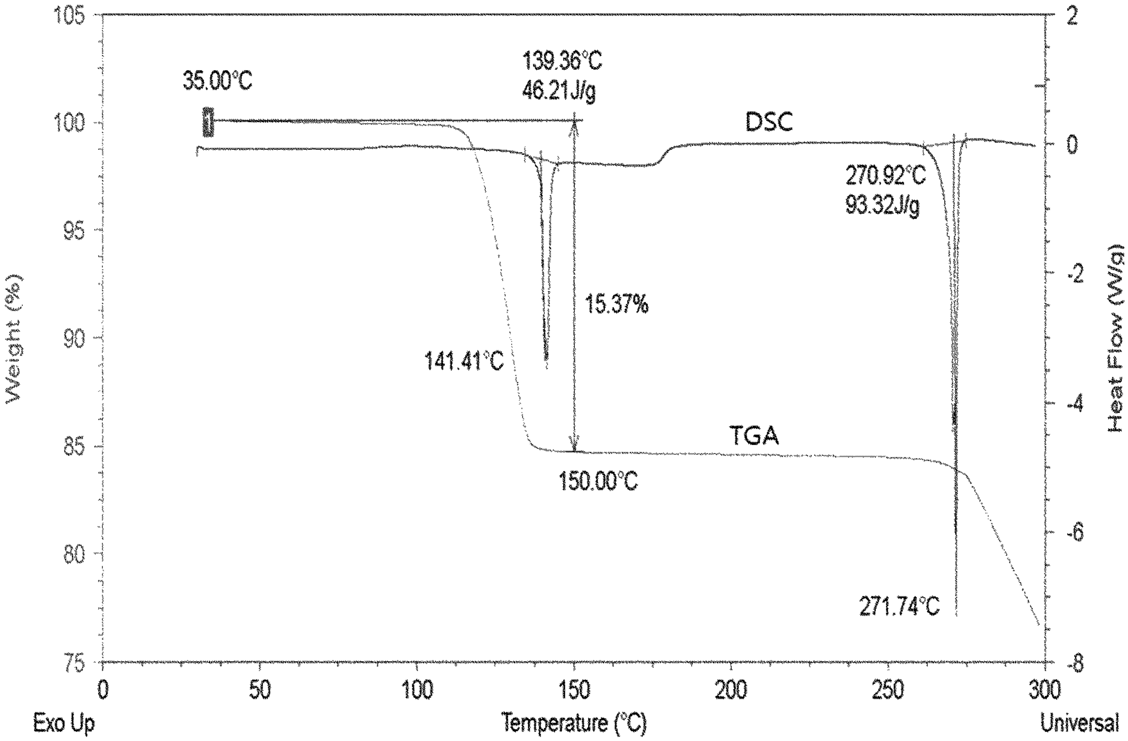
FIG. 9 shows TGA/DSC overlay results for Crystalline Form V.

FIG. 9 shows TGA/DSC overlay results for Crystalline Form V.

Meanwhile, $^{1}$H NMR results were as follow.

$^{1}$H NMR (400 MHz, CHLOROFORM-d) δ ppm 1.22-1.34 (m, 1H), 1.56-1.72 (m, 4H), 2.16 (br d, J=12.88 Hz, 2H), 2.64 (s, 3H), 3.05 (br d, J=9.26 Hz, 8H), 3.55-3.81 (m, 6H), 4.10 (br d, J=11.63 Hz, 2H), 6.49 (s, 1H), 6.77 (d, J=1.50 Hz, 1H), 7.02 (s, 1H), 7.28 (s, 1H), 7.32-7.39 (m, 1H), 7.47 (t, J=7.63 Hz, 2H), 7.73 (br d, J=7.38 Hz, 2H), 8.68 (br s, 1H)

Figure 10:
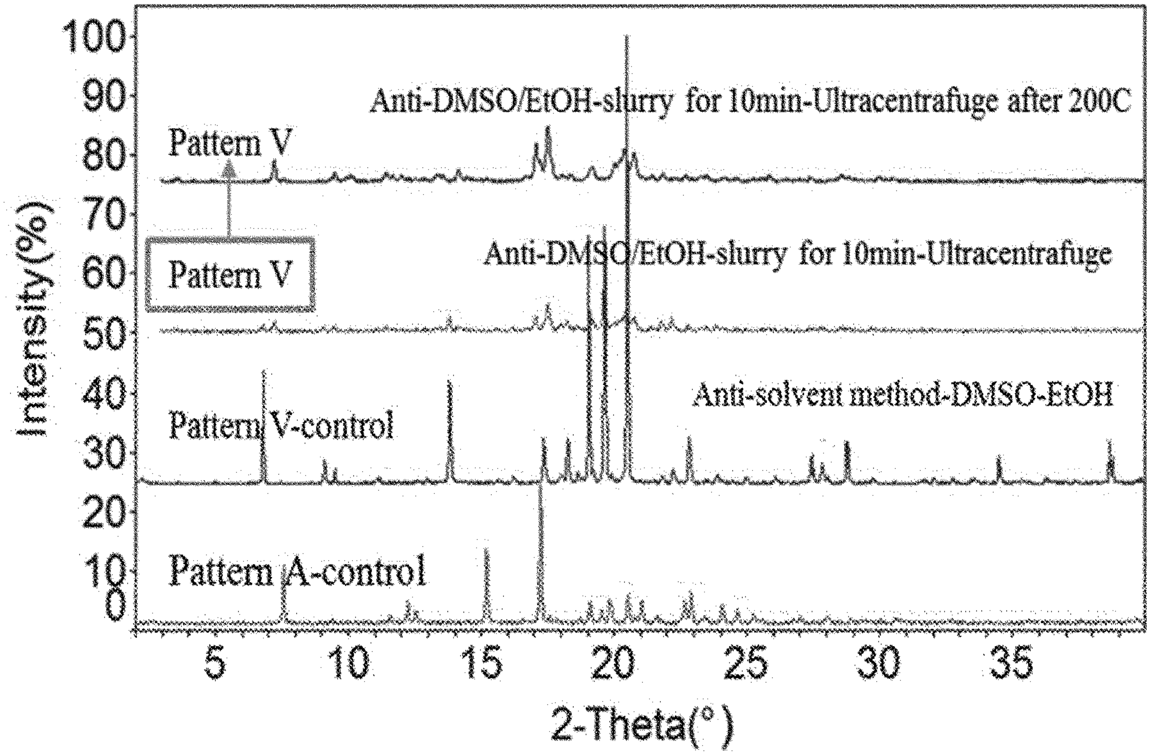
FIG. 10 shows XRPD results measured after TGA testing of Crystalline Form V.

Whereas DMSO appeared to exist in Crystalline Form V based on $^{1}$H-NMR and TGA/DSC data, it continued to maintain Crystalline Form V even after heating to 200° C. to remove DMSO and chilling, and therefore appears to be a crystalline form which is not a DMSO solvate (FIG. 10). FIG. 10 shows XRPD results measured after TGA testing (heating to 200° C. then cooling) of Crystalline Form V.

Example 3-4: Crystalline Form VIII (DMSO Solvate)—Slurry Method 50 mg of the compound of Chemical Formula 1 in 1 mL DMSO was agitated for 4 weeks in a slurry state at room temperature. The solid obtained using a centrifuge was vacuum dried to obtain crystals. This was named Crystalline Form VIII of the compound of Chemical Formula 1, and XRPD, DSC/TGA and $^{1}$H NMR were measured.

TABLE 6

List of characteristic XRPD peaks of Crystalline Form VIII

| 2-Theta(°) | Distance(Å) | Counts | Intensity % |
|---|---|---|---|
| 6.879 | 12.8395 | 230 | 11.0 |
| 9.106 | 9.7034 | 135 | 6.5 |
| 10.153 | 8.7053 | 159 | 7.6 |
| 11.064 | 7.9906 | 109 | 5.2 |
| 11.769 | 7.5135 | 67 | 3.2 |
| 13.752 | 6.4339 | 559 | 26.8 |
| 14.056 | 6.2956 | 63 | 3.0 |
| 14.730 | 6.0088 | 158 | 7.6 |
| 16.171 | 5.4765 | 210 | 10.1 |
| 16.871 | 5.2509 | 61 | 2.9 |
| 17.321 | 5.1154 | 133 | 6.4 |
| 17.930 | 4.9431 | 456 | 21.8 |
| 19.180 | 4.6236 | 77 | 3.7 |
| 19.470 | 4.5554 | 114 | 5.5 |
| 19.814 | 4.4772 | 101 | 4.8 |
| 20.181 | 4.3964 | 2089 | 100.0 |
| 20.675 | 4.2925 | 154 | 7.4 |
| 21.081 | 4.2109 | 161 | 7.7 |
| 21.369 | 4.1547 | 96 | 4.6 |
| 22.819 | 3.8939 | 191 | 9.1 |
| 23.247 | 3.8232 | 91 | 4.4 |
| 23.923 | 3.7166 | 64 | 3.1 |
| 24.201 | 3.6745 | 80 | 3.8 |
| 25.188 | 3.5327 | 94 | 4.5 |
| 25.842 | 3.4448 | 406 | 19.4 |
| 26.412 | 3.3717 | 271 | 13.0 |
| 27.698 | 3.2180 | 125 | 6.0 |
| 28.374 | 3.1429 | 53 | 2.5 |
| 29.050 | 3.0712 | 29 | 1.4 |
| 29.679 | 3.0075 | 201 | 9.6 |
| 30.443 | 2.9338 | 65 | 3.1 |
| 31.388 | 2.8476 | 27 | 1.3 |
| 33.015 | 2.7109 | 111 | 5.3 |
| 33.355 | 2.6841 | 76 | 3.6 |
| 33.830 | 2.6475 | 78 | 3.7 |
| 34.588 | 2.5911 | 35 | 1.7 |
| 34.811 | 2.5750 | 38 | 1.8 |
| 35.347 | 2.5372 | 38 | 1.8 |
| 35.687 | 2.5138 | 34 | 1.6 |
| 36.400 | 2.4662 | 40 | 1.9 |
| 36.874 | 2.4356 | 34 | 1.6 |
| 38.733 | 2.3228 | 35 | 1.7 |
| 39.649 | 2.2713 | 51 | 2.4 |

Figure 11:
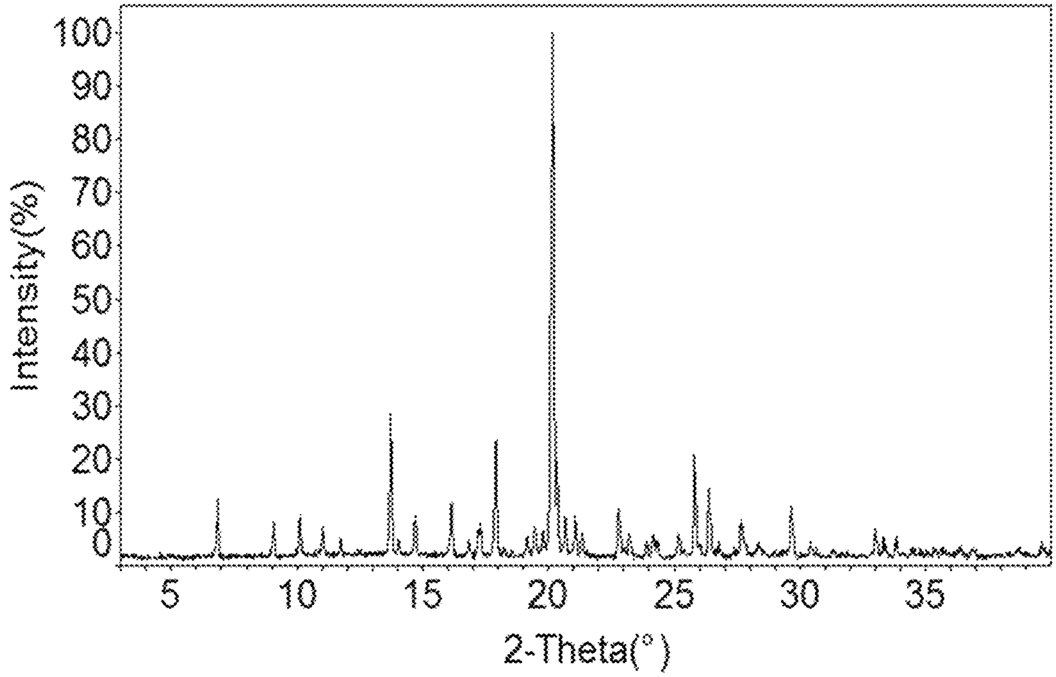
FIG. 11 shows X-ray powder diffraction pattern (XRPD) analysis results for Crystalline Form VIII.

FIG. 11 and Table 6 show X-ray powder diffraction pattern (XRPD) analysis results for Crystalline Form VIII.

The form of Crystalline Form VIII is characterized in that it is identified using a X-ray powder diffraction pattern having at least four diffraction peaks at 2[Θ] values selected from 6.88±0.2, 13.75±0.2, 16.17±0.2, 17.93±0.2, 20.18±0.2, 22.82±0.2, 25.84±0.2, 26.41±0.2 and 29.68±0.2.

Figure 12:
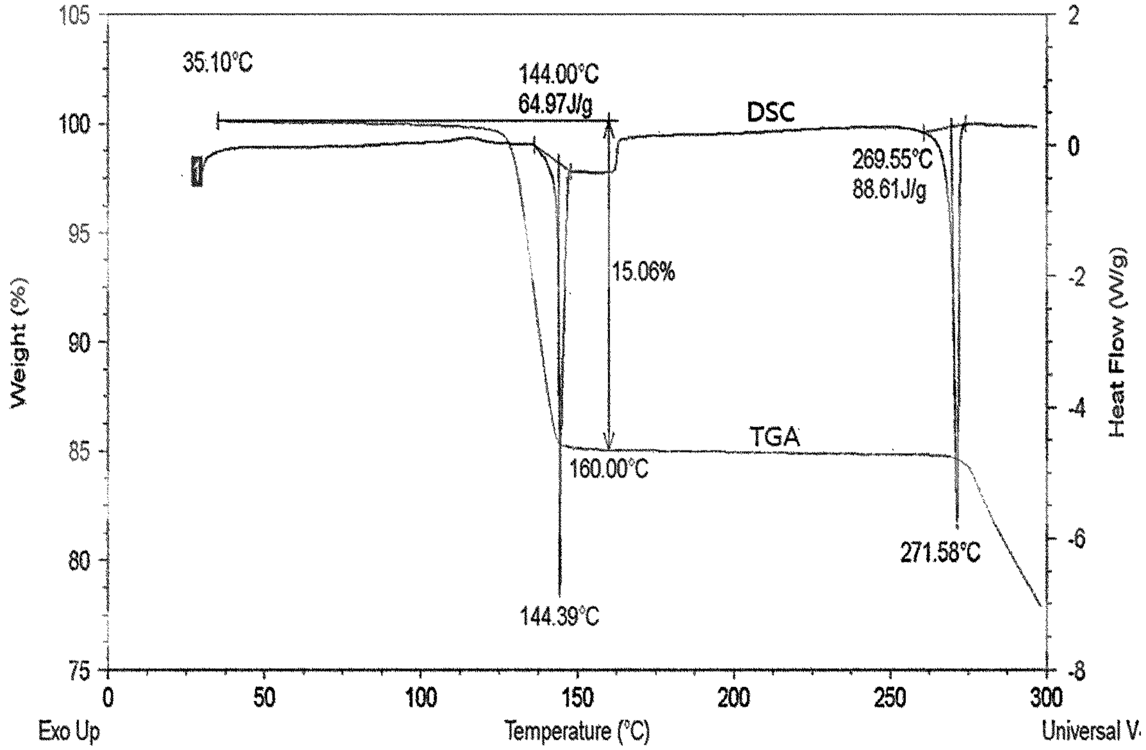
FIG. 12 shows TGA/DSC overlay results for Crystalline Form VIII.

FIG. 12 shows TGA/DSC overlay results for Crystalline Form VIII.

Meanwhile, $^{1}$H NMR results were as follow.

$^{1}$H NMR (400 MHz, CHLOROFORM-d) δ ppm 1.58-1.77 (m, 4H), 2.16 (br d, J=11.54 Hz, 2H), 2.58-2.70 (m, 7H, DMSO peak), 2.93-3.14 (m, 8H), 3.55-3.78 (m, 5H), 4.10 (dt, J=11.80, 3.26 Hz, 2H), 6.47 (s, 1H), 6.76 (d, J=2.01 Hz, 1H), 7.00 (s, 1H), 7.28 (s, 1H), 7.31-7.38 (m, 1H), 7.46 (t, J=7.65 Hz, 2H), 7.70-7.82 (m, 2H), 8.99 (br s, 1H).

Figure 13:
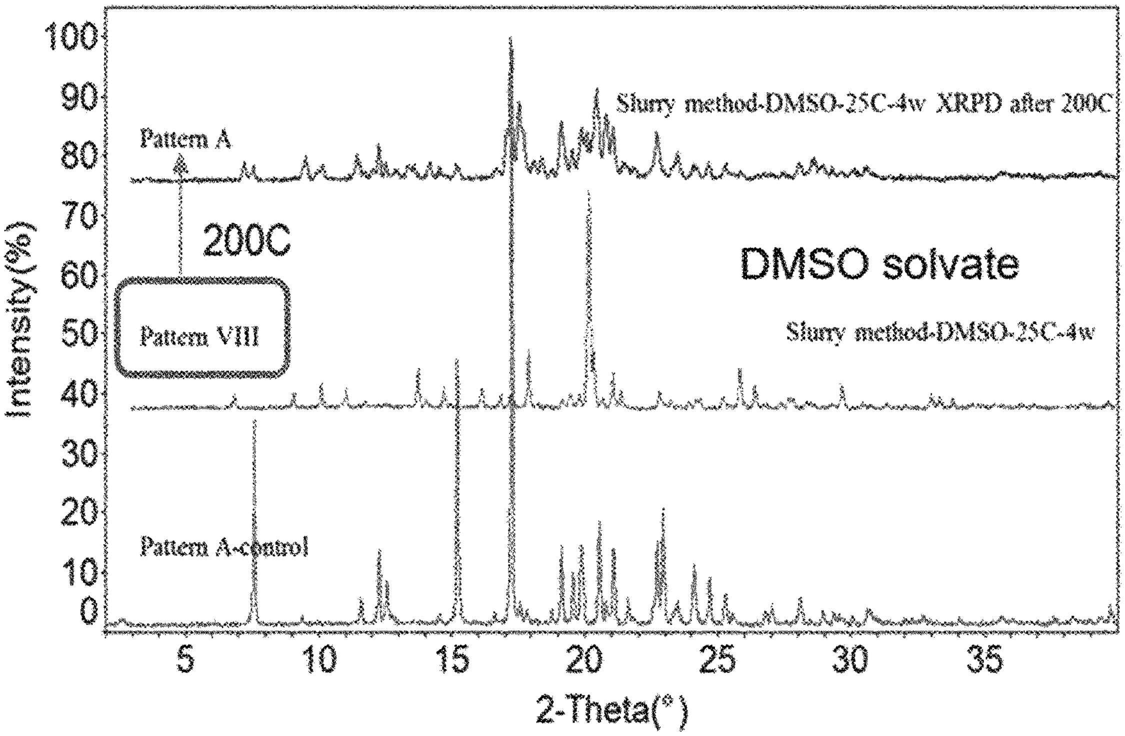
FIG. 13 shows XRPD results measured after TGA testing of Crystalline Form VIII.

Crystalline Form VIII appears to be a DMSO solvate (the compound of Chemical Formula 1: DMSO=1:1) based on $^{1}H$ NMR and TGA/DSC data. When heated to 200° C. and chilled in TGA/XRPD, DMSO was removed from the DMSO solvate and a different crystalline form was observed, identified as Crystalline Form XII (FIG. 13). FIG. 13 shows XRPD results measured after TGA testing (heating to 200° C. then cooling) of Crystalline Form VIII.

Example 3-5: Crystalline Form XII—Slurry Method 100 mg of Crystalline Form V of the compound of Chemical Formula 1 obtained in Example 3-3 was placed in 1 mL EtOH and agitated for 3 days at room temperature. A 0.45 μm polytetrafluoroethylene (PTFE) filter was used to dry the generated solid at 50° C. to obtain crystals. This was named Crystalline Form XII of the compound of Chemical Formula 1 (later renamed as "Pattern A" or "Crystalline Form A"), and XRPD and DSC were measured.

TABLE 7

List of characteristic XRPD peaks of Crystalline Form XII

| 2-Theta(°) | Distance(Å) | Counts | Intensity % |
|---|---|---|---|
| 7.633 | 11.5720 | 1194 | 18.7 |
| 11.623 | 7.6072 | 316 | 5.0 |
| 12.314 | 7.1820 | 850 | 13.3 |
| 12.586 | 7.0274 | 342 | 5.4 |
| 12.786 | 6.918 | 92 | 1.4 |
| 15.242 | 5.8081 | 1576 | 24.7 |
| 16.647 | 5.3209 | 86 | 1.3 |
| 17.282 | 5.1268 | 6381 | 100 |
| 17.608 | 5.0326 | 242 | 3.8 |
| 17.89 | 4.9539 | 128 | 2.0 |
| 18.794 | 4.7176 | 141 | 2.2 |
| 19.162 | 4.6279 | 946 | 14.8 |
| 19.59 | 4.5277 | 599 | 9.4 |
| 19.933 | 4.4507 | 910 | 14.3 |
| 20.586 | 4.3109 | 1093 | 17.1 |
| 20.819 | 4.2633 | 183 | 2.9 |
| 21.103 | 4.2065 | 1001 | 15.7 |
| 21.669 | 4.0978 | 222 | 3.5 |
| 21.852 | 4.064 | 101 | 1.6 |
| 22.734 | 3.9082 | 677 | 10.6 |
| 22.939 | 3.8737 | 1001 | 15.7 |
| 23.546 | 3.7752 | 308 | 4.8 |
| 24.109 | 3.6884 | 794 | 12.4 |
| 24.698 | 3.6017 | 535 | 8.4 |
| 25.29 | 3.5187 | 246 | 3.9 |
| 25.536 | 3.4853 | 121 | 1.9 |
| 26.819 | 3.3214 | 109 | 1.7 |
| 27.047 | 3.294 | 206 | 3.2 |
| 28.127 | 3.1699 | 343 | 5.4 |
| 28.971 | 3.0794 | 177 | 2.8 |
| 29.411 | 3.0343 | 113 | 1.8 |
| 30.663 | 2.9133 | 241 | 3.8 |
| 32.726 | 2.7342 | 103 | 1.6 |
| 35.661 | 2.5156 | 130 | 2.0 |
| 36.057 | 2.4888 | 82 | 1.3 |
| 38.365 | 2.3443 | 79 | 1.2 |
| 39.407 | 2.2847 | 81 | 1.3 |

Figure 14:
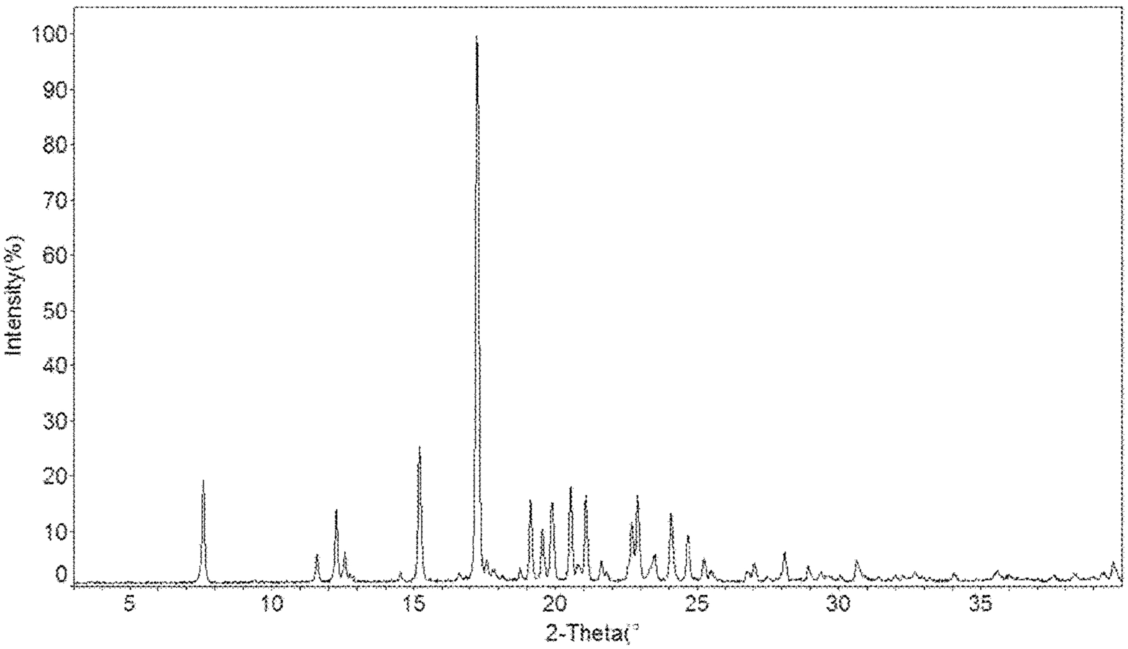
FIG. 14 shows X-ray powder diffraction pattern (XRPD) analysis results for Crystalline Form XII.

FIG. 14 and Table 7 show X-ray powder diffraction pattern (XRPD) analysis results for Crystalline Form XII.

The form of Crystalline Form XII is characterized in that it is identified using a X-ray powder diffraction pattern having at least four diffraction peaks at 2[Θ] values selected from 7.64±0.2, 12.32±0.2, 12.62±0.2, 15.26±0.2, 17.32±0.2, 19.18±0.2, 19.61±0.2, 19.95±0.2, 20.60±0.2, 21.12±0.2, 22.94±0.2, 24.11±0.2, and 28.15±0.2.

Figure 15:
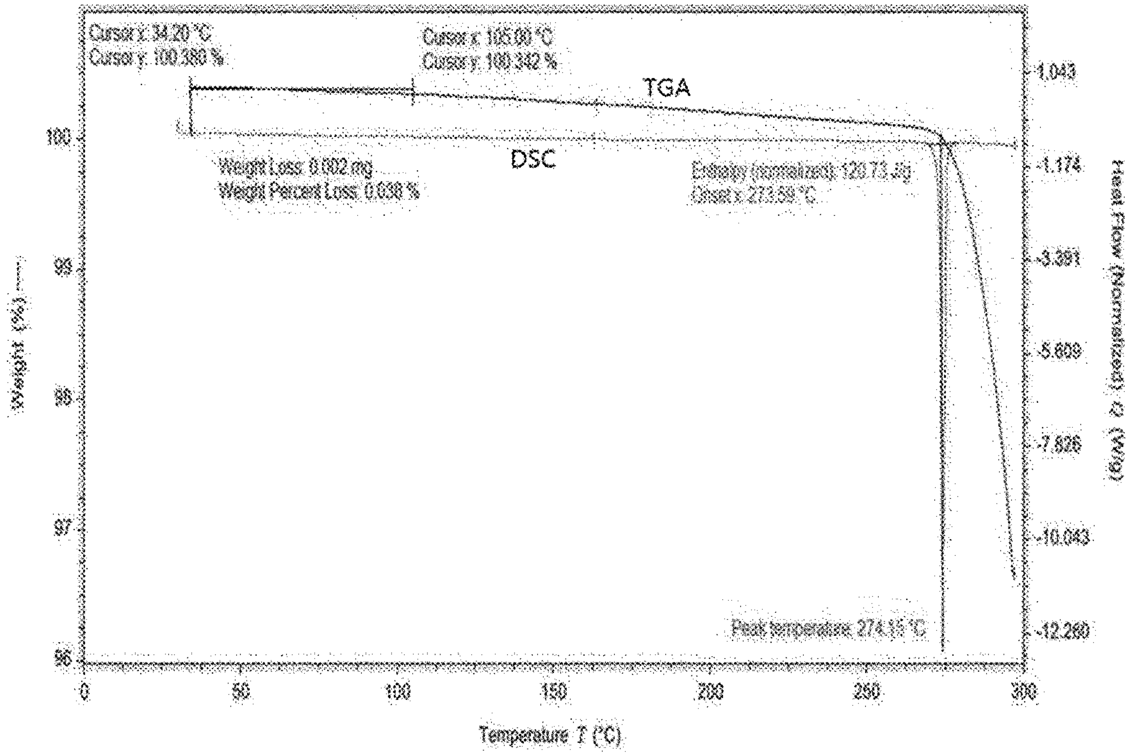
FIG. 15 shows TGA/DSC overlay results for Crystalline Form XII.

FIG. 15 shows TGA/DSC overlay results for Crystalline Form XII.

From the above results, it can be known that the mesomorphic form V is converted into the more stable Crystalline form XII through slurrification.

Example 3-6: Crystalline Form XI (NMP Solvate)—Slurry Method 500 mg of the compound of Chemical Formula 1 was placed in 1 mL NMP, then agitated for 3 hours at 25° C. The supernatant was removed using an ultracentrifuge, and the remaining solid was vacuum dried to obtain crystals. This was named Crystalline Form XI of the compound of Chemical Formula 1, and XRPD, DSC/TGA, and $^{1}H$ NMR were measured.

TABLE 8

List of characteristic XRPD peaks of Crystalline Form XI

| 2-Theta(°) | Distance(Å) | Counts | Intensity % |
|---|---|---|---|
| 8.419 | 10.4941 | 157 | 7.8 |
| 9.617 | 9.1887 | 84 | 4.2 |
| 10.071 | 8.7762 | 96 | 4.7 |
| 10.482 | 8.4330 | 75 | 3.7 |
| 13.216 | 6.6935 | 66 | 3.3 |
| 13.701 | 6.4578 | 94 | 4.6 |
| 15.417 | 5.7426 | 149 | 7.4 |
| 15.620 | 5.6686 | 107 | 5.3 |
| 16.605 | 5.3344 | 170 | 8.4 |
| 16.889 | 5.2453 | 2024 | 100.0 |
| 17.297 | 5.1225 | 860 | 42.5 |
| 17.869 | 4.9598 | 115 | 5.7 |
| 19.240 | 4.6093 | 51 | 2.5 |
| 19.445 | 4.5611 | 34 | 1.7 |
| 20.369 | 4.3564 | 164 | 8.1 |
| 20.954 | 4.2359 | 810 | 40.0 |
| 21.178 | 4.1918 | 335 | 16.6 |
| 21.338 | 4.1606 | 225 | 11.1 |
| 22.100 | 4.0189 | 45 | 2.2 |
| 23.163 | 3.8368 | 669 | 33.1 |
| 24.040 | 3.6988 | 165 | 8.2 |
| 24.655 | 3.6080 | 61 | 3.0 |
| 25.209 | 3.5298 | 50 | 2.5 |
| 26.556 | 3.3537 | 143 | 7.1 |
| 27.428 | 3.2491 | 73 | 3.6 |
| 27.845 | 3.2014 | 254 | 12.5 |
| 28.275 | 3.1537 | 140 | 6.9 |
| 28.966 | 3.0799 | 108 | 5.3 |
| 29.311 | 3.0445 | 47 | 2.3 |
| 29.983 | 2.9778 | 142 | 7.0 |
| 30.366 | 2.9411 | 25 | 1.2 |
| 31.065 | 2.8765 | 45 | 2.2 |
| 31.437 | 2.8433 | 53 | 2.6 |
| 32.573 | 2.7467 | 37 | 1.8 |
| 34.053 | 2.6306 | 82 | 4.1 |
| 34.871 | 2.5707 | 34 | 1.7 |
| 36.130 | 2.4840 | 27 | 1.3 |
| 36.988 | 2.4283 | 27 | 1.3 |
| 38.121 | 2.3587 | 37 | 1.8 |
| 38.710 | 2.3242 | 67 | 3.3 |

Figure 16:
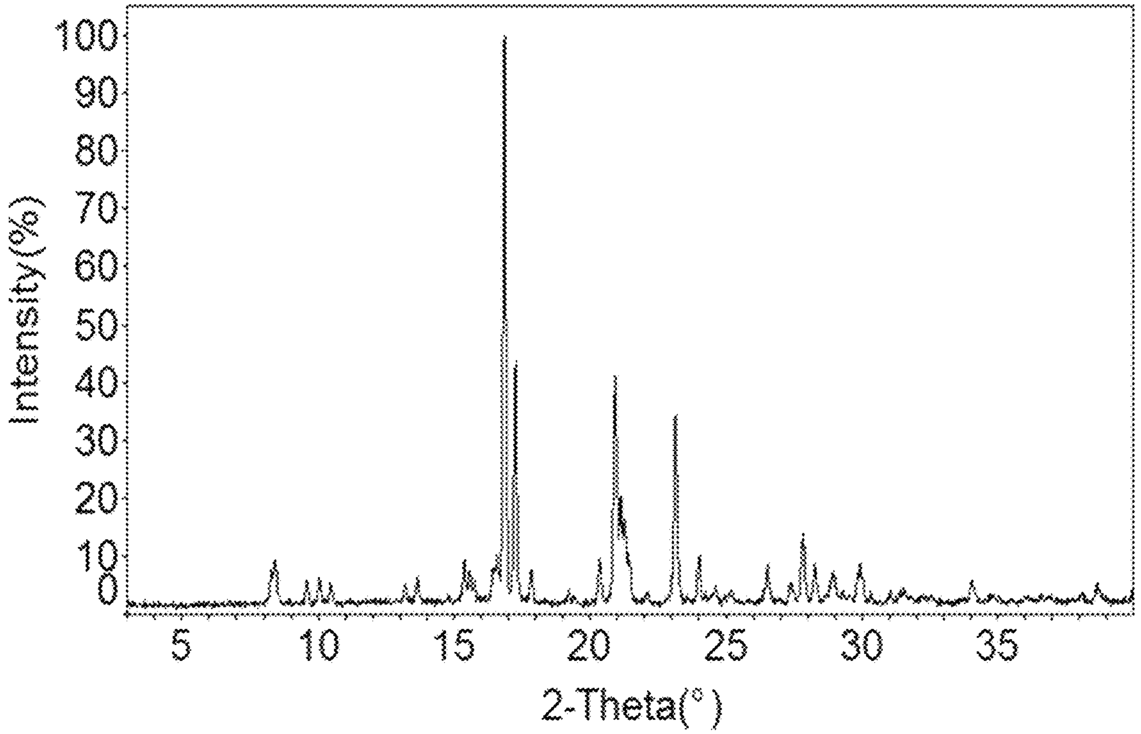
FIG. 16 shows X-ray powder diffraction pattern (XRPD) analysis results for Crystalline Form XI.

FIG. 16 and Table 8 show X-ray powder diffraction pattern (XRPD) analysis results for Crystalline Form XI.

The form of Crystalline Form XI is characterized in that it is identified using a X-ray powder diffraction pattern having at least four diffraction peaks at 2[Θ] values selected from 16.89±0.2, 17.30±0.2, 20.37±0.2, 20.95±0.2, 21.18±0.2, 21.34±0.2, 23.16±0.2, 24.04±0.2, and 27.85±0.2.

Figure 17:
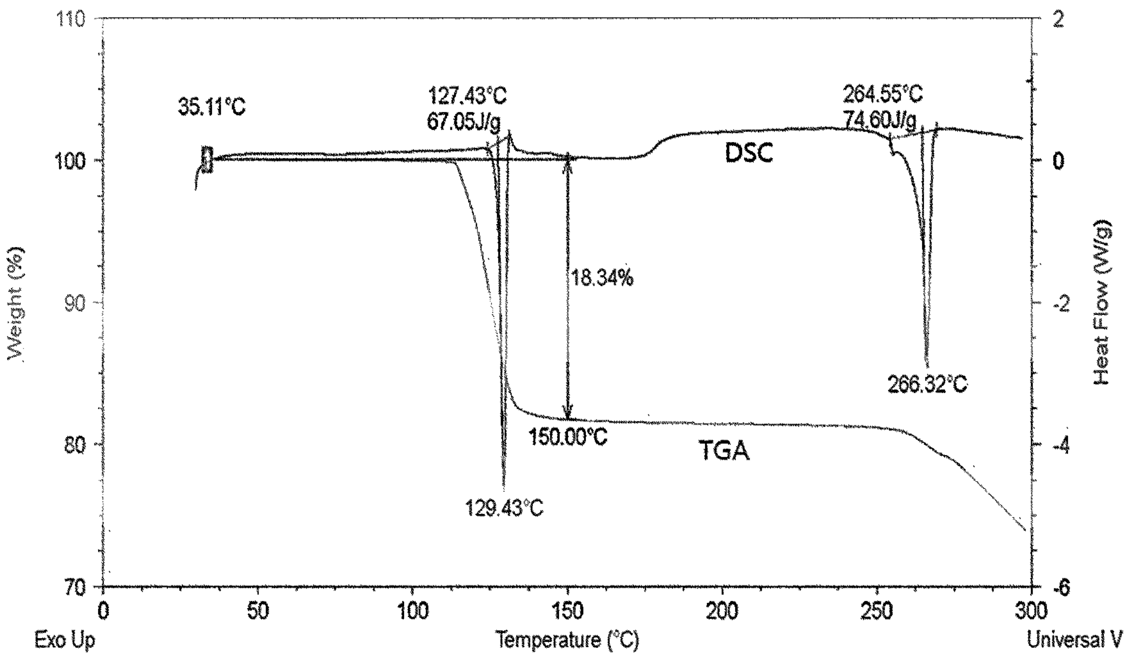
FIG. 17 shows TGA/DSC overlay results for Crystalline Form XI.

FIG. 17 shows TGA/DSC overlay results for Crystalline Form XI.

Meanwhile, the $^1$H NMR results were as follow.

$^1$H NMR (400 MHz, DMSO-$d_6$) δ ppm 1.40-1.54 (m, 2H), 1.84-1.96 (m, 2H), 2.06 (br d, J=11.54 Hz, 2H), 2.13-2.23 (m, 2H), 2.70 (s, 3H, NMP-Me), 2.89 (br s, 4H), 3.08 (br d, J=4.52 Hz, 4H), 3.46-3.56 (m, 2H), 3.59-3.72 (m, 3H), 3.89-3.99 (m, 2H), 5.35 (d, J=7.53 Hz, 1H), 6.32 (s, 1H), 6.76 (s, 2H), 7.28-7.35 (m, 1H), 7.48 (t, J=7.78 Hz, 2H), 7.80 (d, J=7.53 Hz, 2H), 10.94 (s, 1H).

Based on the XRPD, DSC/TGA and $^1$H NMR results, Crystalline form XI was an NMP solvate (the compound of Chemical Formula 1: NMP=1:1).

Figure 18:
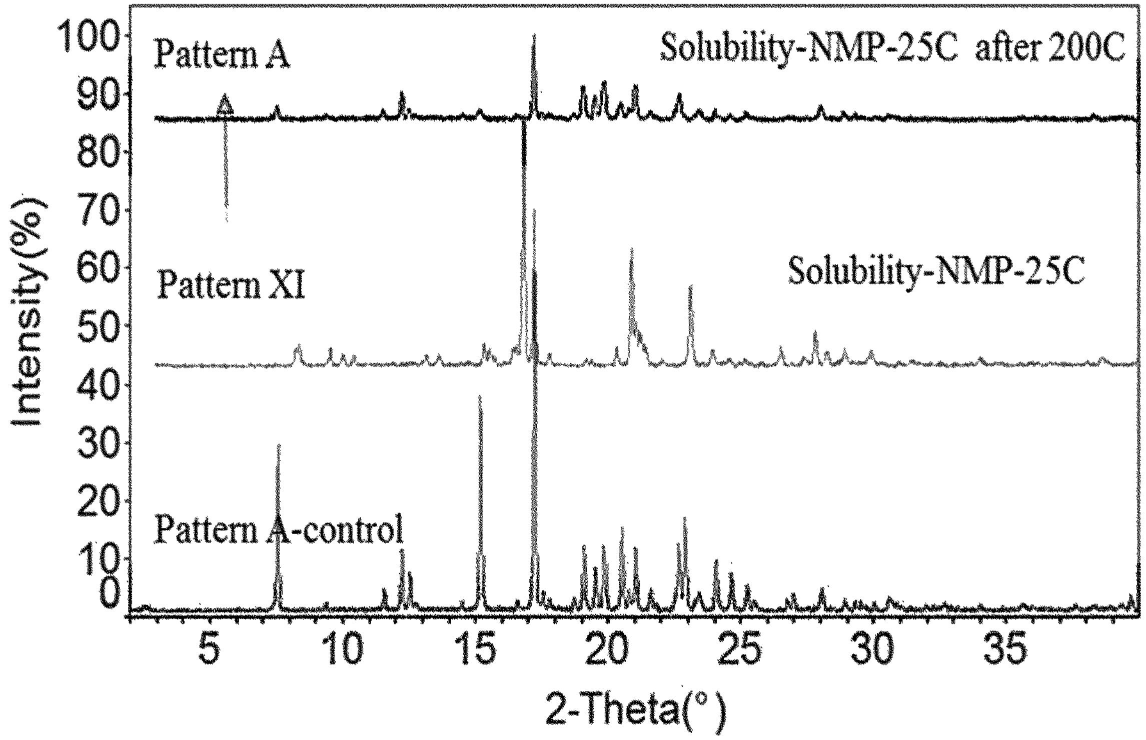
FIG. 18 shows XRPD results measured after TGA of Crystalline Form XI.

Meanwhile, in the TGA/XRPD results, when heated to 200° C. and chilled, NMP was removed with conversion to Crystalline Form XII (FIG. 18). FIG. 18 shows XRPD results measured after TGA testing (heating to 200° C. then cooling) of Crystalline Form XI.

Summary of Example 3

TABLE 9

Comparison of 5 crystalline forms in Example 3

| | Crystalline Form IV | Crystalline Form V | Crystalline Form VIII | Crystalline Form XI | Crystalline Form XII (Crystalline A) |
|---|---|---|---|---|---|
| Melting point and enthalpy (° C./J/g) | 96/270 39.11/73.08 | 141/272 46.21/93.32 | 144/272 64.97/88.61 | 129/266 67.05/74.60 | 274 120.73 |
| Mass loss rate (TGA, %) | 12.95% (<120° C.) | 15.37% (<150° C.) | 15.06% (<160° C.) | 18.34% (<150° C.) | 0.04% (<160° C.) |
| Summary | DMF solvate (1:1) | Anhydrous, metastable | DMSO solvate (1:1) | NMP solvate (1:1) | Anhydrous, most stable |

Example 4: Stability Testing of 5 Crystalline Forms

Stability testing was carried out over 8 weeks at harsh conditions (40° C., 75%, relative humidity) on the 5 crystalline forms obtained in Example 3.

Table 10 below show the results of stability testing of the 5 crystalline forms.

TABLE 10

Results from stability testing of 5 crystalline forms

| Initial Crystalline Form | Condition | Appear-ance | XRPD Patterns | Purity | Assay |
|---|---|---|---|---|---|
| Crystalline Form IV (DMF Solvate) | Initial | Yellow powder | Pattern IV | 99.87% | 100.00% |
| | 40° C./75% RH, 1 week | Yellow powder | Pattern A | 99.73% | 101.81% |
| | 40° C./75% RH, 2 weeks | Yellow powder | Pattern A | 99.88% | 105.36% |
| | 40° C./75% RH, 4 weeks | Yellow powder | Pattern A | 99.87% | 99.58% |
| | 40° C./75% RH, 8 weeks | Yellow powder | Pattern A | 99.86% | 104.25% |
| Crystalline Form V (DMSO metastable) | Initial | Light yellow powder | Pattern V | 99.37% | 100.00% |
| | 40° C./75% RH, 1 week | Light yellow powder | Pattern A | 99.60% | 103.86% |
| | 40° C./75% RH, 2 weeks | Light yellow powder | Pattern A | 99.21% | 103.99% |

TABLE 10-continued

Results from stability testing of 5 crystalline forms

| Initial Crystalline Form | Condition | Appear-ance | XRPD Patterns | Purity | Assay |
|---|---|---|---|---|---|
| | 40° C./75% RH, 4 weeks | Light yellow powder | Pattern A | 99.16% | 98.50% |
| | 40° C./75% RH, 8 weeks | Yellow powder | Pattern A | 99.36% | 104.75% |
| Crystalline Form VIII (DMSO solvate) | Initial | White powder | Pattern VIII | 99.94% | 100.00% |
| | 40° C./75% RH, 1 week | White powder | Pattern A | 99.95% | 106.67% |
| | 40° C./75% RH, 2 weeks | White powder | Pattern A | 99.91% | 102.74% |
| | 40° C./75% RH, 4 weeks | White powder | Pattern A | 99.83% | 105.56% |
| | 40° C./75% RH, 8 weeks | White powder | Pattern A | 100.00% | 107.08% |

TABLE 10-continued

Results from stability testing of 5 crystalline forms

| Initial Crystalline Form | Condition | Appear-ance | XRPD Patterns | Purity | Assay |
|---|---|---|---|---|---|
| Crystalline Form XI (NMP solvate) | Initial | Off white powder | Pattern XI | 99.55% | 100.00% |
| | 40° C./75% RH, 1 week | Off white powder | Pattern A + XI | 99.70% | 95.79% |
| | 40° C./75% RH, 2 weeks | Off white powder | Pattern A + XI | 99.36% | 105.59% |
| | 40° C./75% RH, 4 weeks | Off white powder | Pattern A | 99.56% | 103.58% |
| | 40° C./75% RH, 8 weeks | Off white powder | Pattern A | 99.58% | 104.04% |
| Crystalline Form XII (Crystalline Form A) | Initial | Off white powder | Pattern A | 98.85% | 100.00% |
| | 40° C./75% RH, 1 week | Off white powder | Pattern A | 99.19% | 101.17% |
| | 40° C./75% RH, 2 weeks | Off white powder | Pattern A | 98.69% | 102.12% |
| | 40° C./75% RH, 8 weeks | Off white powder | Pattern A | 99.88% | 102.17% |

As can be seen in Table 10, there was almost no change in purity under harsh conditions for all 5 crystalline forms. Crystalline forms IV, VIII and XI were confirmed to be DMF, DMSO and NMP solvates, respectively based on $^1$H NMR spectroscopy and DSC/TGA results and were found to become converted into Crystalline Form XII after observing for 8 weeks under harsh conditions (40° C., 75% relative humidity). Crystalline Form V was not a solvate but a metastable form, which was found to also be converted into Crystalline Form XII. Accordingly, it was judged that Crystalline Form XII was the most stable crystalline form, and Crystalline Form XII was renamed Crystalline Form A or Pattern A (Crystalline Form XII=Crystalline Form A or Pattern A).

Example 5: Optimization Step I

Example 5-1 Deciding the Initial Concentration of the Compound of Chemical Formula 1

Figure 19:
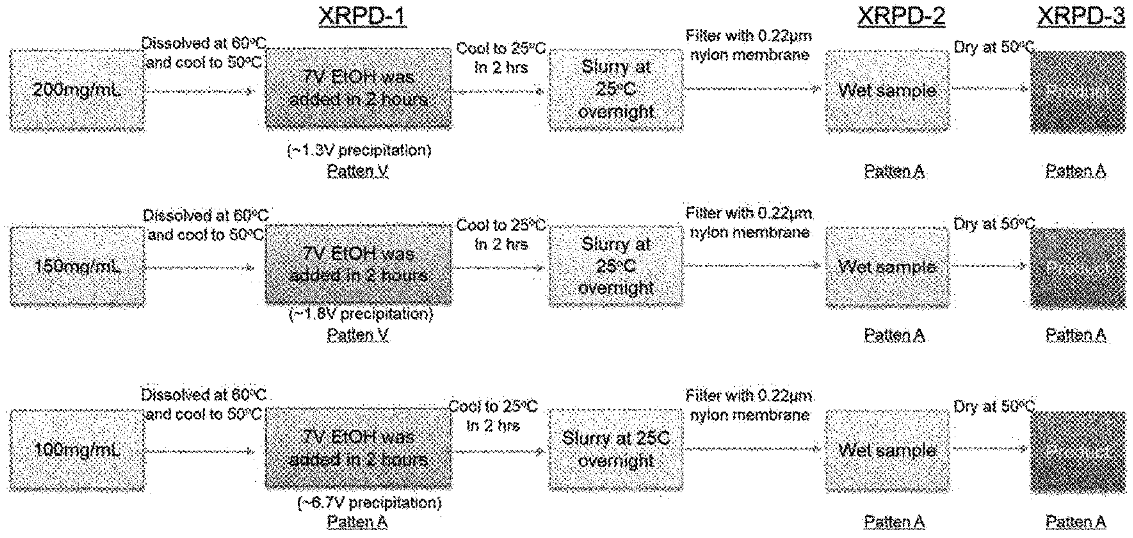
FIG. 19 shows mimetic diagrams for small-scale recrystallization tests (Test 1 to 3) for the compound of Chemical Formula 1.

FIG. 19 shows mimetic diagrams for small-scale recrystallization tests (Test 1 to 3) for the compound of Chemical Formula 1. As shown in FIG. 19, to decide the initial concentration of the compound of Chemical Formula 1 to DMSO solvent, the compound of Chemical Formula 1 was dissolved to concentrations of 100, 150 and 200 mg/mL, EtOH in an amount 7 times the amount of the compound of Chemical Formula 1 was added over two hours at 50° C., followed by agitation for 19 hours at room temperature. XRPD was measured and yield was calculated for each step, with the solid generated immediately after addition of EtOH (XRPD-1), the solid generated after agitating for 1 day at room temperature (XRPD-2), and the solid vacuum dried at 50° C.(XRPD-3).

TABLE 11

Results of small-scale recrystallization tests (Tests 1~3) on the compound of Chemical Formula 1

| Test no. | Conc. (mg/mL) | Method | DMSO/EtOH | XRPD-1-wet | XRPD-2-wet | XRPD-3-dry | Yield (%) | Purity (%) |
|---|---|---|---|---|---|---|---|---|
| 1 | 200 | Anti- | 1 V:7 V | V | A | A | 87.53 | 100.00 |
| 2 | 150 | solvent | 1 V:7 V | V | A | A | 83.39 | 100.00 |
| 3 | 100 | | 1 V:7 V | A | A | A | 76.55 | 100.00 |

As can be seen in Table 11, the initial Crystalline Form V was generated at 150 and 200 mg/mL concentrations and was observed to convert into Crystalline Form A as time passed. Based on the results of these tests, the initial concentration for crystallization was chosen to be 200 mg/mL, where the yield was highest.

Example 5-2. Deciding the DMSO/EtOH Ratio

Figure 20:
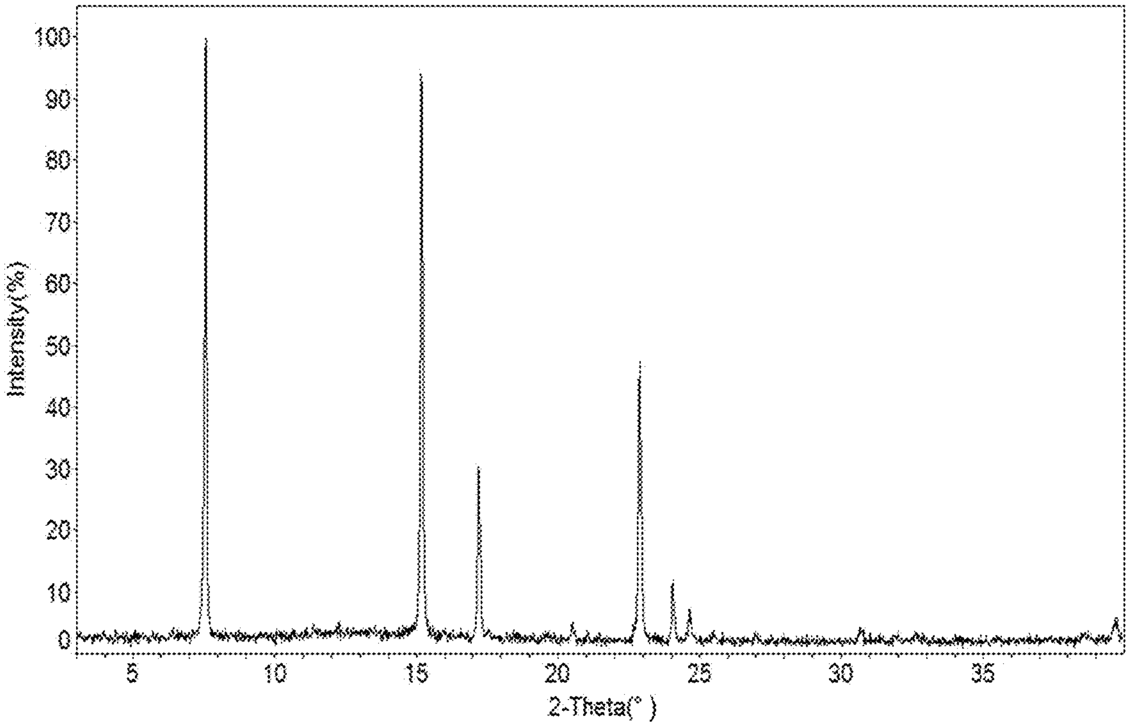
FIG. 20 shows X-ray powder diffraction pattern (XRPD) analysis results for Intermediate Form-I, which is an intermediate of the process of conversion from Crystalline Form V to Crystalline Form A (test 4).
Figure 21:
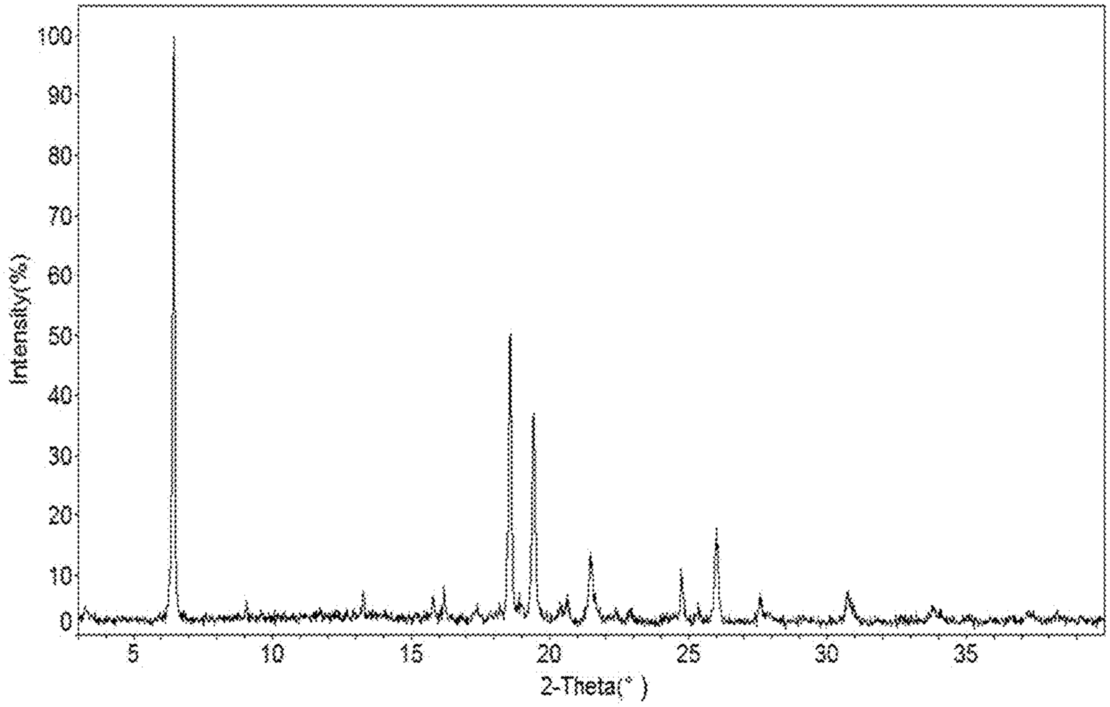
FIG. 21 shows X-ray powder diffraction pattern (XRPD) analysis results for Intermediate Form-II, which is an intermediate of the process of conversion from Crystalline Form V to Crystalline Form A (test 5).

To decide the ratio of anti-solvent EtOH to the compound of Chemical Formula 1 200 mg/mL DMSO solution, 5 times and 7 times EtOH was added respectively over 2 hours at 50° C., followed by 16 hours agitation at room temperature. The solid obtained by filtering was vacuum dried at 50° C. XRPD was measured for each of the specimens prior to drying, and changers during the drying process were observed as well, and the yield was obtained (Table 12). The solid obtained from 7 times EtOH had a yield of 84.15% and exhibited XRPD spectrums exhibiting characteristic peaks of Crystalline Form V before drying and those corresponding to halfway between the conversion from Crystalline Form V to Crystalline Form A after drying (test 4, Intermediate-I) (FIG. 20). In contrast, the solid obtained from 5 times EtOH had a yield of 76.55% and exhibited characteristic peaks of Crystalline Form V prior to drying, and those of a new characteristic intermediate crystalline form different from the pattern from the conversion from Crystalline Form V to Crystalline Form A after drying (test 5, Intermediate-II) (FIG. 21). Based on these results, it was decided that DMSO:EtOH=1:7 was a better condition for yield and recrystallization in Crystalline Form A than 1:5.

TABLE 12

Results from small-scale recrystallization testing on the compound of Chemical Formula 1 (Test 4~5)

| Test No. | Conc. (mg/mL) | Method | DMSO/EtOH | XRPD-1-wet | XRPD-2-wet | XRPD-3-dry | Yield (%) | Purity (%) |
|---|---|---|---|---|---|---|---|---|
| 4 | 200 | Anti-solvent | 1 V:7 V | V | V | V→A* (Intermediate I) | 84.15 | 100.00 |
| 5 | 200 | Anti-solvent | 1 V:5 V | V | V | Not A, not V (Intermediate II) | 76.55 | 100.00 |

Note: XRPD-1, XRPD-2 and XRPD-3 represent the crystalline forms immediately after adding anti-solvent, after agitating for one day, and after drying, respectively V→A*: Intermediate step in conversion from Crystalline Form V to Crystalline Form A FIG. 20 and Table 13 show XRPD analysis results for Intermediate Form-I.

TABLE 13

List of characteristic XRPD peaks of Intermediate-I (Intermediate-I)

| 2-Theta(°) | Distance(Å) | Counts | Intensity % |
|---|---|---|---|
| 7.611 | 11.6057 | 1072 | 100 |
| 15.223 | 5.8152 | 1005 | 93.8 |
| 17.246 | 5.1375 | 302 | 28.2 |
| 22.919 | 3.8771 | 497 | 46.4 |
| 24.084 | 3.6921 | 105 | 9.8 |
| 24.656 | 3.6078 | 58 | 5.4 |

FIG. 21 and Table 14 show XRPD analysis results for Intermediate Form-II.

TABLE 14

List of characteristic XRPD peaks of Intermediate-II (test 5, Intermediate-II)

| 2-Theta(°) | Distance(Å) | Counts | Intensity % |
|---|---|---|---|
| 6.489 | 13.6102 | 1137 | 100 |
| 16.219 | 5.4604 | 66 | 5.8 |
| 18.605 | 4.7652 | 559 | 49.2 |
| 19.465 | 4.5566 | 405 | 35.6 |
| 21.509 | 4.1279 | 132 | 11.6 |
| 24.781 | 3.5898 | 101 | 8.9 |
| 26.045 | 3.4184 | 186 | 16.4 |
| 30.78 | 2.9024 | 61 | 5.4 |

100 mg of Intermediate-I obtained above was placed in 1 mL EtOH, then agitated for 3 days at room temperature. The solid generated using a 0.45 μm PTFE filter was dried in vacuum at 50° C. XRPD analysis at completion of drying identified the solid as Crystalline Form A (Table 15). From these results, it could be known that Crystalline Form V is a metastable crystalline form and converts into the more stable Crystalline Form A with sufficient time and under sufficient conditions.

TABLE 15

Result of additional slurrification for Intermediate-I

| No. | Conc. (mg/mL) | Method | Solvent | Initial XRPD | Final XRPD | Yield (%) | Purity (%) |
|---|---|---|---|---|---|---|---|
| Test 4 | 100 | Slurry | EtOH | V→A (Intermediate-I) | A | 80.00 | 100.00 |

Further, in a case using DMSO/EtOH mixed solvent, conditions in the crystallization process may cause crystalline forms of different converting patterns midway. Therefore, it became necessary to establish a preparation process wherein the most stable crystalline form is generated from the time point where recrystallization initially begins.

Example 5-3. Optimizing Time for Dropwise Addition of Anti-Solvent (EtOH) to DMSO Solution Using the crystallization method used in Example 5-2 but more slowly adding EtOH in an amount seven times that of DMSO over 24 hours and 35 hours (In test 7, after dropwise addition of 6.7% EtOH, 20% of Form A was added as a seed crystal), the XRPD was analyzed for the crystalline forms obtained from each step. Considered together with the results from Example 5-1 (dropwise addition of 19 hours), changing the time over which EtOH was added dropwise and use of seed crystal could not avoid generation of the initial Crystalline Form V, but it was found that after completion of drying, pure Crystalline Form A without other crystalline forms could be obtained.

TABLE 16

Results for recrystallization of compound of chemical formula 1 according to the different addition time of anti-solvent dropwisely (Test 6~7)

| No. | Solvent | Anti-solvent | Conc. (mg/mL) | Ratio | Adding time | Slurry time | XRPD-1-wet | XRPD-2-wet | XRPD-3-dry | Purity (%) | Yield (%) |
|---|---|---|---|---|---|---|---|---|---|---|---|
| Test 6 | DMSO | EtOH | 200 | 1:7 | 24 h | 13 h | V | A | A | 100.00 | 72.28 |
| Test 7 | | | 200 | 1:7 | 35 h | 21 h | V* | A | A | 99.97 | 86.36 |

*Seed crystal added

Example 6: Recrystallization of the Compound of Chemical Formula 1 in DMSO/MTBE Solvent 5 times and 7 times MTBE anti-solvent was added to the compound of Chemical Formula 1 150 mg/mL DMSO solution at 50° C. over 3 hours, then agitated for 18 hours at room temperature. The solid obtained by filtering was vacuum dried for 18 hours at 50° C. Here, changes in the drying process were examined by measuring respective XRPDs prior to and after vacuum drying. The solid obtained from 7×MTBE had a yield of 64.73%, exhibiting the XRPD of Crystalline Form V both before and after drying. The solid obtained from 5×MTBE at 59.27% yield also exhibited the Crystalline Form V both before and after drying.

TABLE 17

Results for recrystallization of the compound of Chemical Formula 1 in DMSO/MTBE solvent (Test 8~9)

| No. | Conc. (mg/mL) | Method | DMSO/MTBE | XRPD-3 | Yield (%) | Purity (%) |
|---|---|---|---|---|---|---|
| Test 8 | 150 | Anti-solvent | 1 V:7 V | V | 64.73 | 100.00 |

TABLE 17-continued

Results for recrystallization of the compound of Chemical Formula 1 in DMSO/MTBE solvent (Test 8~9)

| No. | Conc. (mg/mL) | Method | DMSO/MTBE | XRPD-3 | Yield (%) | Purity (%) |
|---|---|---|---|---|---|---|
| Test 9 | 150 | Anti-solvent | 1 V:7 V | V | 59.27 | 100.00 |

Example 7: Recrystallization of the Compound of Chemical Formula 1 in NMP/EtOH Solvent 7 times the anti-solvent EtOH was added to the compound of Chemical Formula 1 150 mg/mL NMP solution at 25° C. over 24 to 35 hours, followed by 22 to 33 hours agitation at room temperature. The solid obtained by filtering was vacuum dried for 2 hours at 50° C. Here, changes in the drying process were examined by measuring respective XRPDs prior to and after vacuum drying. The solid was obtained at a yield of 65 to 74%, and in the NMP/EtOH combination as well, initial formation of Crystalline Form XI was observed.

TABLE 18

Results for recrystallization of the compound of Chemical Formula 1 in NMP/EtOH solvent (Test 10~11)

| No. | Solvent | Anti-solvent | Conc. (mg/mL) | Ratio | Adding time | Slurry time | XRPD-1-wet | XRPD-2-wet | XRPD-3-dry | Purity (%) | Yield (%) |
|---|---|---|---|---|---|---|---|---|---|---|---|
| Test 10 | NMP | EtOH | 150 | 1:7 | 24 h | 22 h | X1 (NMP solvate) | A | A | 100.00 | 74.37 |
| Test 11 | | | 150 | 1:7 | 35 h | 33 h | N/A | XI (NMP solvate) | A | 100.00 | 65.33 |

Analysis of Results of Examples 5 Through 7

Observing the results of Examples 5, 6, and 7, it was found that under various possible mixed solvent conditions, colored crystalline forms were yielded as well as individual intermediate crystalline forms which are unstable. Giving consideration to form, yield and residual solvent toxicity, the DMSO/EtOH combination appeared to be the best candidate, and the following optimization was carried out.

TABLE 19

Summary of mixed solvent results used for recrystallization of the compound of Chemical Formula 1

| Solvent Condition | DMSO/EtOH | NMP/EtOH | DMSO/MTBE |
|---|---|---|---|
| Possible crystalline forms* | V or VIII (DMSO mesomorphic or solvate) | XI (NMP solvate) | V (DMSO mesomorphic) |
| Appearance | White powder | Blue powder | White powder |
| Yield % | 72~85% | 65~74% | 59~65% |
| Residual solvent ICH class | Class III (low toxicity) | Class II | Class III (low toxicity) |

Example 8: Optimizing EMSO/EtOH Solvent Ratio

Figure 22:
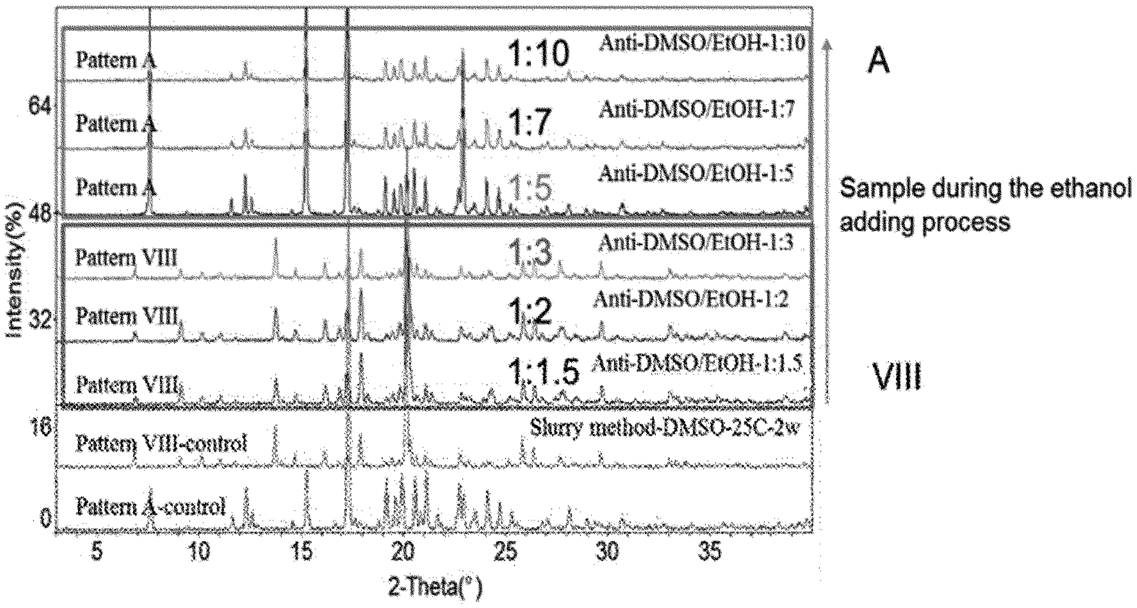
FIG. 22 shows X-ray powder diffraction pattern (XRPD) analysis results for the compound of Chemical Formula 1 recrystallized at varying DMSO/EtOH ratios.

Example 8-1: Experiments to Optimize DMSO/EtOH Anti-Solvent Ratio 200 mg of the compound of Chemical Formula 1 was placed in 1 mL DMSO, heated to 60° C., then filtered using a 0.45 μm PTFE membrane. To the solution obtained, 10 times the amount of DMSO of EtOH (10 mL) was slowly added at 50° C. over 35 hours. The crystalline forms of the initial solid obtained at time points where the amount of EtOH introduced was 1.5 times, 2 times, 3, times, 5 times, 7 times and 10 times the amount of DMSO were measured and analyzed. FIG. 22 shows X-ray powder diffraction pattern (XRPD) analysis results for the compound of Chemical Formula 1 recrystallized at varying DMSO/EtOH ratios. As can be seen in FIG. 22, the solvate Crystalline Form VIII is formed at 1:3 or less, and Crystalline Form A was found to be formed in cases where DMSO/EtOH=1:5 or higher. To identify a more accurate ratio, optimization of slurrification conditions was carried out in the next step.

Example 8-2: Experiment to Optimize Ratio of Mixed DMSO/EtOH Solvent at 50° C.

Figure 23:
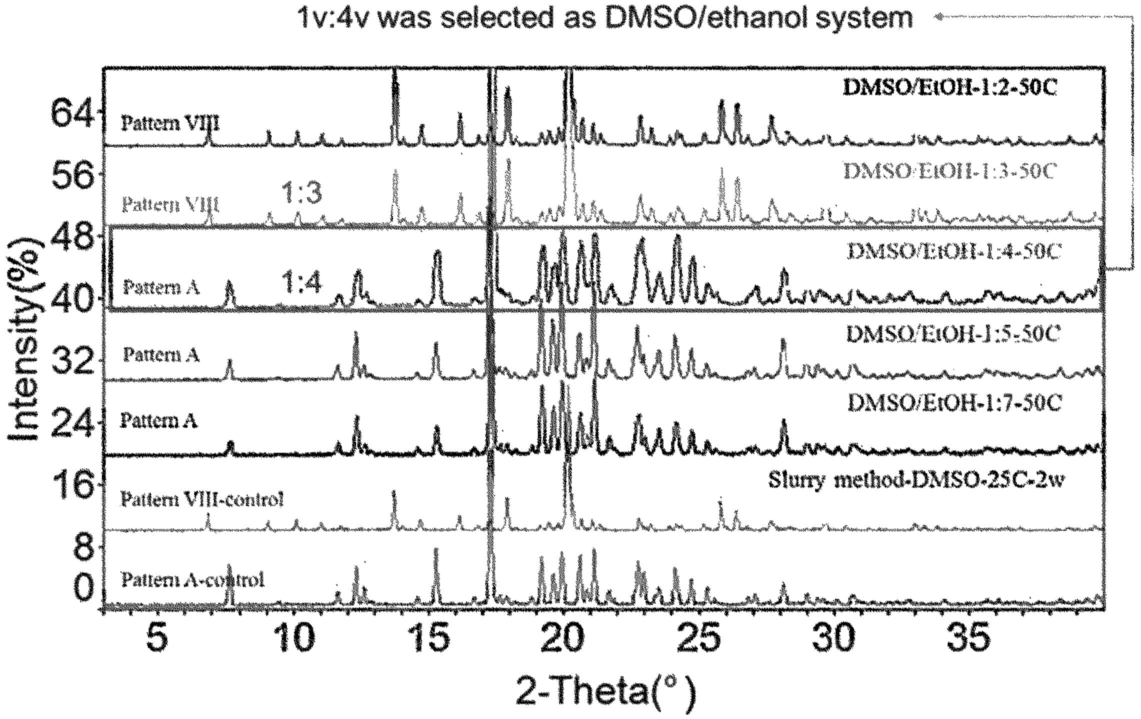
FIG. 23 shows X-ray powder diffraction pattern (XRPD) analysis results for the compound of Chemical Formula 1 recrystallized at varying DMSO/EtOH ratios (1:2, 1:3, 1:4, 1:5, 1:7) at 50° C.

1 mL of DMSO/EtOH mixed solvent (1:2, 1:3, 1:4, 1:5, 1:7) and 200 mg of the compound of Chemical Formula 1 were added to each of 5 vessels and agitated for one day at 50° C. The crystalline form of the solid obtained using a centrifuge was measured and analyzed using XRPD. FIG. 23 shows X-ray powder diffraction pattern (XRPD) analysis results for the compound of Chemical Formula 1 slurrified at varying DMSO/EtOH ratios (1:2, 1:3, 1:4, 1:5, 1:7) at 50° C. As can be seen in FIG. 23, Crystalline Form A was stably formed at 50° C. in cases where the DMSO/EtOH ratio was 1:4, 1:5 and 1:7, and the optimum ratio was determined to be DMSO:EtOH=1:4.

Figure 24:
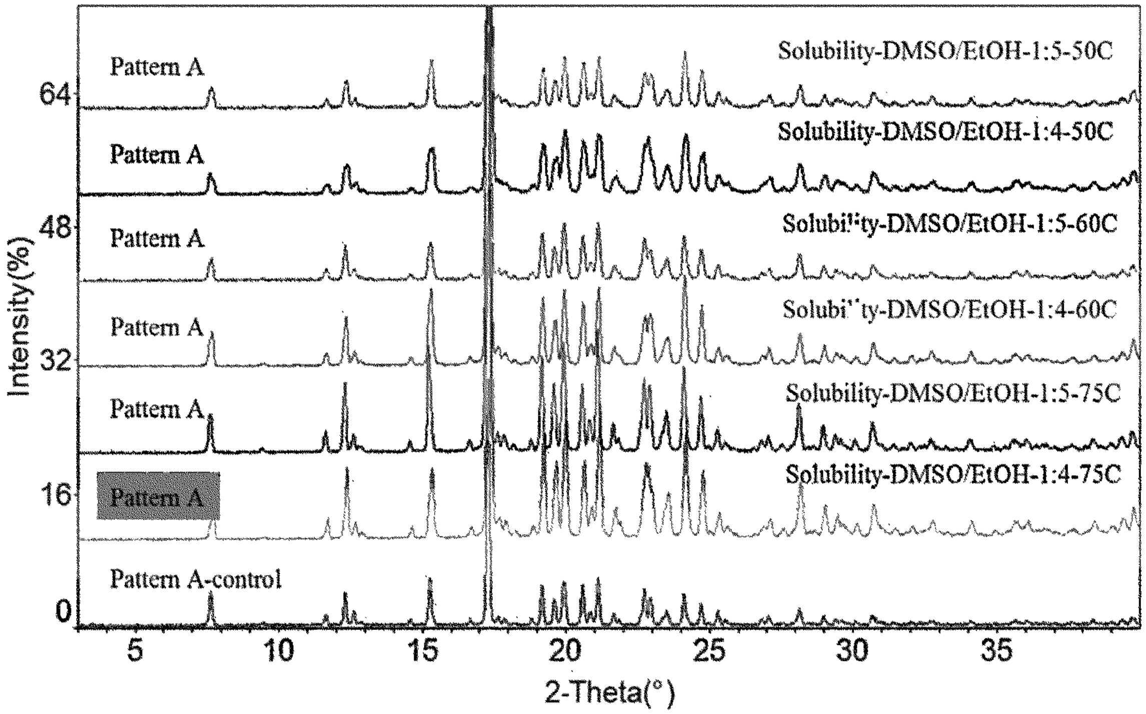
FIG. 24 shows XRPD analysis results for the compound of Chemical Formula 1 slurrified in mixed DMSO/EtOH solvent at various temperatures.

Example 9: Solubility Equilibrium and Super-Saturation in DMSO/EtOH Mixed Solvent by Temperature 200 mg of the compound of Chemical Formula 1 was placed in 1 mL each of two types of DMSO/EtOH (1:4, 1:5) mixed solvent to prepare 200 mg/mL suspensions. These were respectively heated and held at 50° C., 60° C., and 75° C. while being agitated for 6 hours. The supernatants from the suspensions 6 hours later were analyzed with HPLC to find the solubility equilibrium, and the XRPD analysis results of the solids are shown in Table 20 and FIG. 24. FIG. 24 shows XRPD analysis results for the compound of Chemical Formula 1 slurrified in mixed DMSO/EtOH solvent at various temperatures. It was found that the solids existing in all temperature (50° C., 60° C., 75° C.) and mixed solvent (1:4, 1:5) conditions had Crystalline Form A. The solubility in the DMSO/EtOH 1:4 mixed solvent was 31 mg/mL at 75° C., meaning that the recrystallization method using DMSO/EtOH 1:4 mixed solvent was unsuitable from the start. Accordingly, it was decided that a super-saturation method would be considered.

TABLE 20

Solubility of the compound of Chemical Formula 1 in DMSO/EtOH mixed solvent at various temperatures

| DMSO/EtOH | Temperature | Solubility (mg/mL) | XRPD |
|---|---|---|---|
| 1:4 | 75° C. | 31 | Pattern A |
| | 60° C. | 19 | Pattern A |
| | 50° C. | 15 | Pattern A |
| 1:5 | 75° C. | 19 | Pattern A |
| | 60° C. | 14 | Pattern A |
| | 50° C. | 12 | Pattern A |

Note:
Super-saturation = (40 mg/mL)/(31 mg/mL) = 1.3

200 mg of the compound of Chemical Formula 1 was dissolved in 1 mL DMSO and heated to 75° C., then 4 times EtOH was added to create a transparent super-saturated solution with a concentration of 40 mg/mL and a super-saturation of 1.3 times (40/31) the mixed solvent. Based on the results of Example 5-1, it appeared that to target 200 mg the compound of Chemical Formula 1/1 mL DMSO, high yield could be maintained only if solubility was at least 40 mg/mL. Accordingly, it was decided to proceed with the super-saturation method.

Example 10: Method for Preparing Crystalline Form A Through a Super-Saturation/Recrystallization Method Using a Seed Crystal 3 g of the compound of Chemical Formula 1 was added to 15 mL DMSO and dissolved at 75° C., then foreign materials were removed using a 0.45 μm PTFE membrane filter. Holding at 75° C., 60 mL EtOH was added (confirming that a clear solution was maintained in this state), and when 2% seed crystal (Crystalline Form A) was added, a suspension started to be observed. Holding at 75° C., an additional 45 mL EtOH was added slowly over 15 hours. All crystallization was carried out while agitating at 250 RPM. After adding all the EtOH, the mixture was cooled to 5° C. at a rate of 10° C./h. The solid generated was obtained using a 0.45 μm PTFE membrane filter, then vacuum dried for 21 hours at 50° C. As shown in Table 21, recrystallization of the compound of Chemical Formula 1 using a seed crystal exhibited a yield of 74.58% and purity of 99.95%.

TABLE 21

Results of recrystallizing the compound of Chemical Formula 1 (3 g) (Example 10, using seed crystal)

| Method | Appearance | Initial XRPD | Intermediate Products* | Final XRPD | DS yield (%) | Purity (%) |
|---|---|---|---|---|---|---|
| Example 10 | White powder | Crystalline form A | Crystalline form A | Crystalline form A | 74.58 | 99.95 |

Note:
Large amounts of precipitate occurred when EtOH was added.

Figure 25:
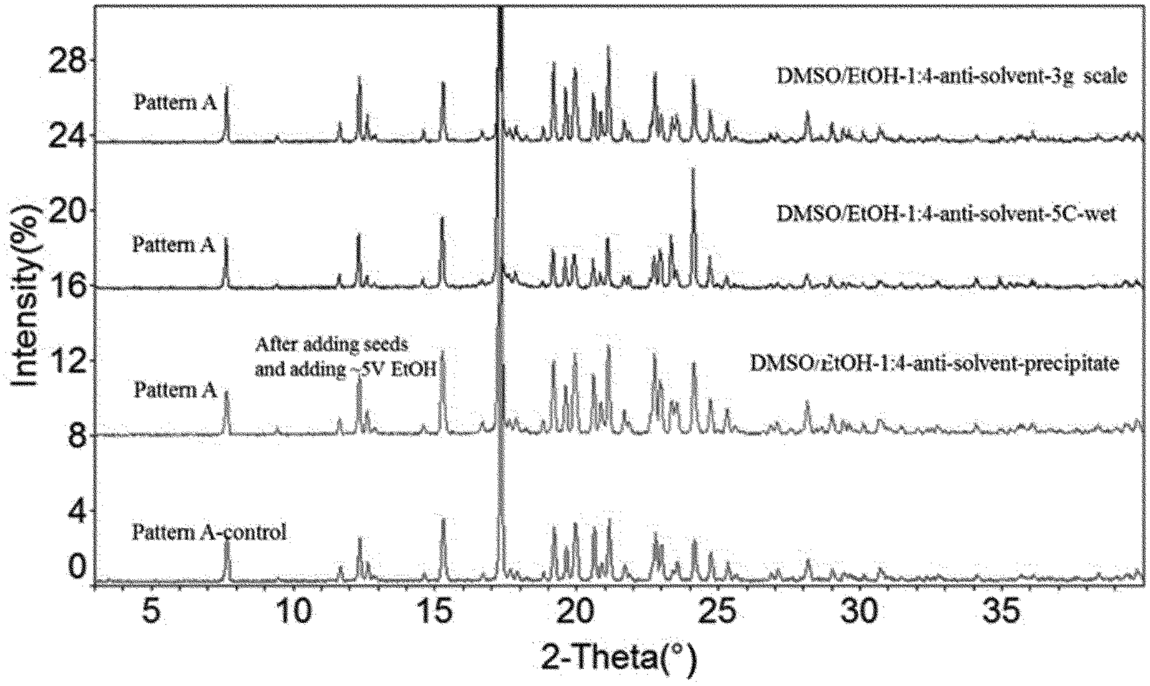
FIG. 25 shows XPRD results at each recrystallization step of the compound of Chemical Formula 1.
Figure 26:
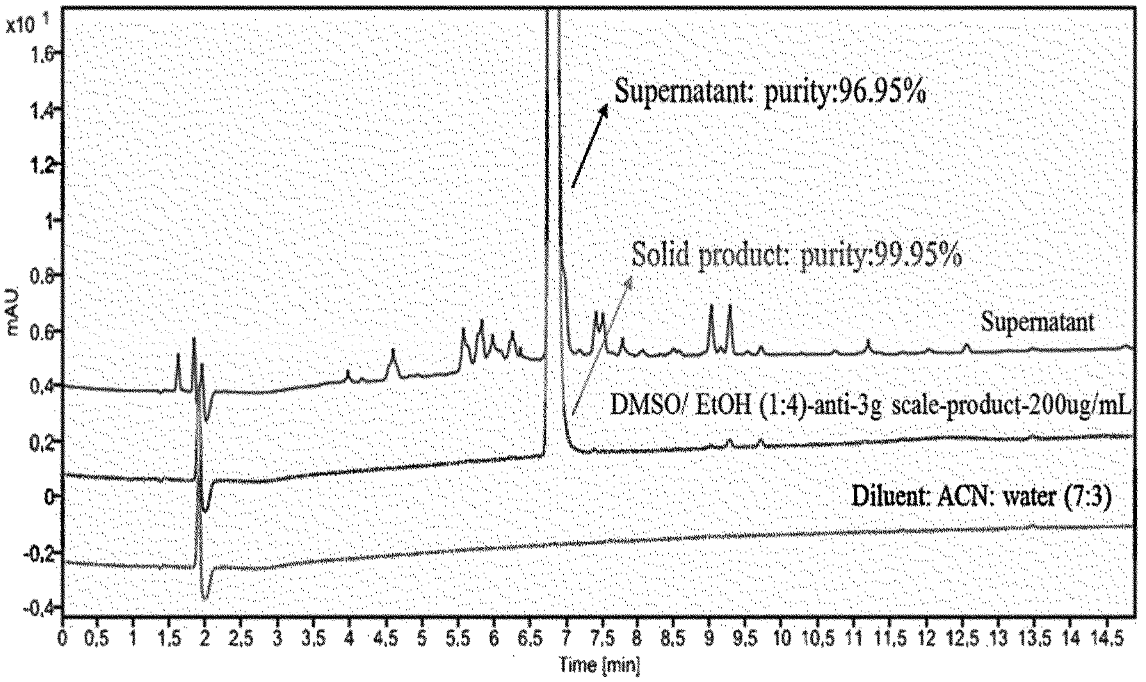
FIG. 26 shows HPLC analysis results for recrystallization products of the compound of Chemical Formula 1.
Figure 27:
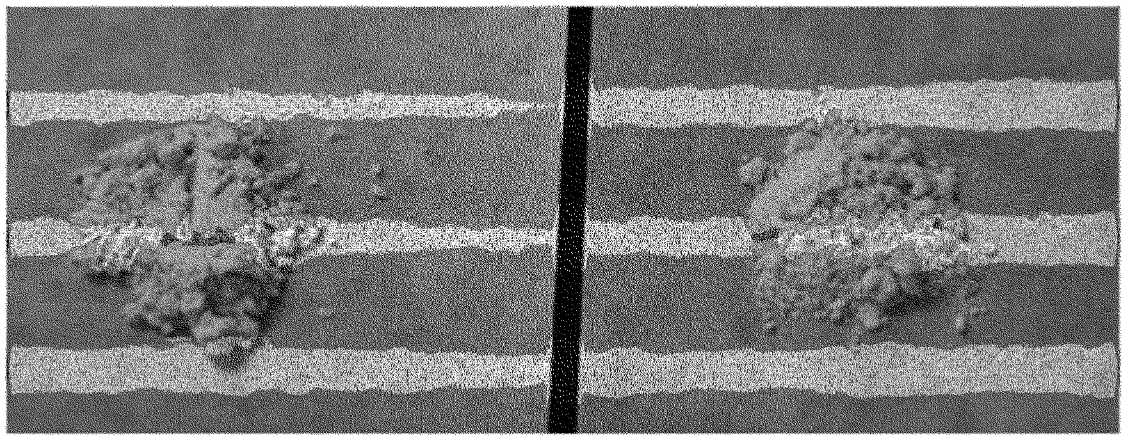
FIG. 27 shows photos of the compound of Chemical Formula 1 prior to recrystallization and recrystallization products thereof.

FIG. 25 shows XPRD results at each recrystallization step of the compound of Chemical Formula 1, FIG. 26 shows HPLC analysis results for recrystallization products of the compound of Chemical Formula 1, and FIG. 27 shows photos of the compound of Chemical Formula 1 prior to recrystallization and recrystallization products thereof. Observing FIG. 27, the compound of Chemical Formula 1 turned from off-white to white after recrystallization, with colored impurities being removed.

Example 11: Method for Preparing Crystalline Form A Through a Super-Saturation/Recrystallization Method not Using a Seed Crystal 2 g of the compound of Chemical Formula 1 was dissolved in 10 mL DMSO at then foreign materials were removed using a 0.45 μm PTFE membrane filter. Holding at 60° C., 40 mL EtOH was added, followed by 30 minutes more agitating (mixture turned into a suspension). [Here, some of the suspension was chilled at room temperature to obtain a solid whose XRPD measurement confirmed it as Crystalline Form V—FIG. 29 (Rapid cooling) solid separated out at room temperature] The temperature was raised again to 75° C. over 12 minutes and held there for 10 minutes (still a suspension). Lowering the temperature slowly to 50° C. over 1.5 hours, the XRPD-1 of the solid formed midway at 60° C. was measured. Holding a temperature of 50° C., 30 mL EtOH was added slowly over 15 hours. All crystallization was carried out while agitating at 250 RPM. The mixture was cooled to 5° C. at a rate of 10° C./h, and the solid formed was isolated with a 0.45 μm PTFE membrane filter to measure XRPD-2, and XRPD-3 was measured after drying in vacuum for 17 hours at 50° C. (Yield 70.35%, purity 99.95%) According to the results in FIG. 29, the XRPDs for each step were all Crystalline Form A.

Figure 29:
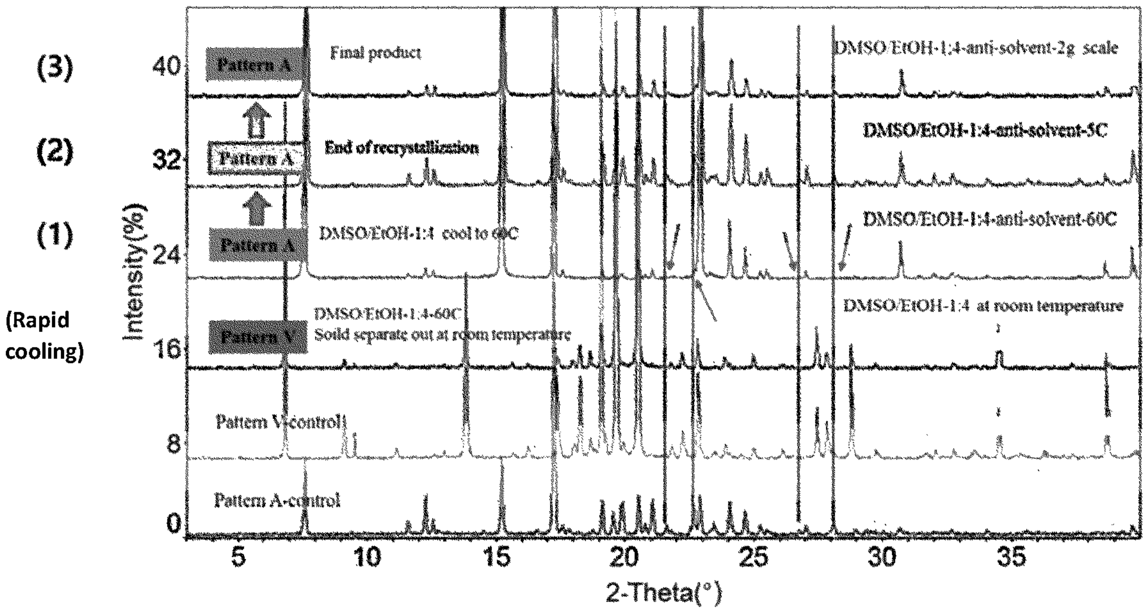
FIG. 29 shows XRPD analysis results of Crystalline Form A prepared using a method not employing a seed crystal.

Further, it was found that if temperature is decreased suddenly during the recrystallization process, Crystalline Form V could act as a nucleus in the recrystallization process, leading to formation of an unwanted crystalline form, confirming that monitoring temperature control was very important (FIG. 29—Rapid cooling).

Comparing Examples 10 and 11, it appeared that Example 10, which uses a seed, was better in terms of yield and form of the powder. It was decided to adjust the total amount of EtOH used as anti-solvent.

Example 12: Adjusting Amount of Anti-Solvent Used in Example 10 (Total DMSO:EtOH=1:5)

1 g of the compound of Chemical Formula 1 was dissolved in 5 mL DMSO at 60° C., then foreign materials were removed using a 0.45 μm PTFE membrane filter. Temperature was raised to 75° C. and held for 30 minutes, then 20 mL EtOH was added, and 2% seed (Crystalline Form A) was added, at which point a suspension began to be observed. Temperature was lowered slowly to 50° C. over 1.5 hours and held while an additional 5 mL EtOH was added slowly over 5 hours followed by 5 hours further agitation at the same temperature. All crystallization was carried out while agitating at 300 RPM. After cooling to 5° C. at a rate of 10° C./hr, the mixture was agitated for 5 more hours at the same temperature. The solid was obtained using a 0.45 μm PTFE membrane filter, then vacuum dried for 20 hours at 50° C. to obtain Crystalline Form A with a yield of 72.12%.

Example 13: Adjusting Amount of Anti-Solvent Used in Example 10 (Total DMSO:EtOH=1:6)

1 g of the compound of Chemical Formula 1 was dissolved in 5 mL DMSO at then foreign materials were removed using a 0.45 μm membrane filter. Temperature was raised to 75° C. and held for 30 minutes, then 20 mL EtOH was added and 2% seed (Crystalline Form A) was added, at which point a suspension began to be observed. Temperature was lowered slowly to 50° C. over 1.5 hours and held while an additional 10 mL EtOH was added slowly over 5 hours followed by 5 hours further agitation at the same temperature. All crystallization was carried out while agitating at 300 RPM. After cooling to 5° C. at a rate of 10° C./hr, the mixture was agitated for 5 more hours at the same temperature. The solid was obtained using a 0.45 μm PTFE membrane filter, then vacuum dried for 20 hours at 50° C. to obtain Crystalline Form A with a yield of 73.28%.

TABLE 22

Summary of results for recrystallization of compound of Chemical Formula 1 (2 g) (Example 11, No Seed crystal)

| Method | Appearance | Initial XRPD | Intermediate products* | Final XRPD | Particle size | DS yield (%) | Purity (%) | DSC | TGA | PLM |
|---|---|---|---|---|---|---|---|---|---|---|
| Example 11 | Slightly green powder | Pattern A | Pattern A | Pattern A | D10: 9.99 vm D50: 55.38 vm D90: 158.06 vm | 69.84 | 99.96 | 272° C., 107 J/g | 0.33% <105° C. | Laminated structure |

Figure 28:
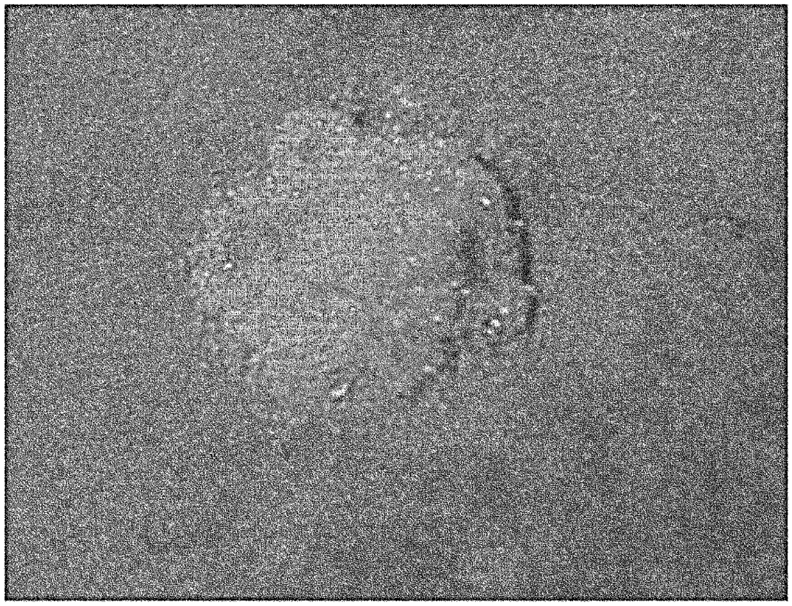
FIG. 28 shows a photograph of Crystalline Form A prepared using a method not employing a seed crystal.
Figure 30:
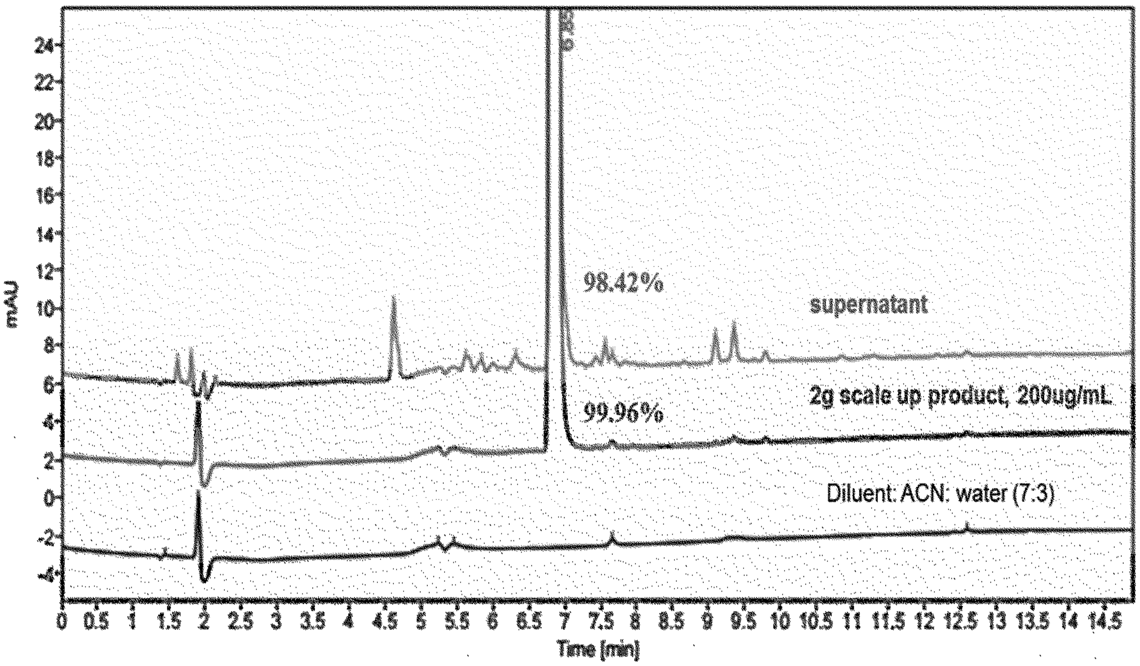
FIG. 30 shows HPLC chromatogram results for Crystalline Form A prepared using a method not employing a seed crystal.
Figure 31:
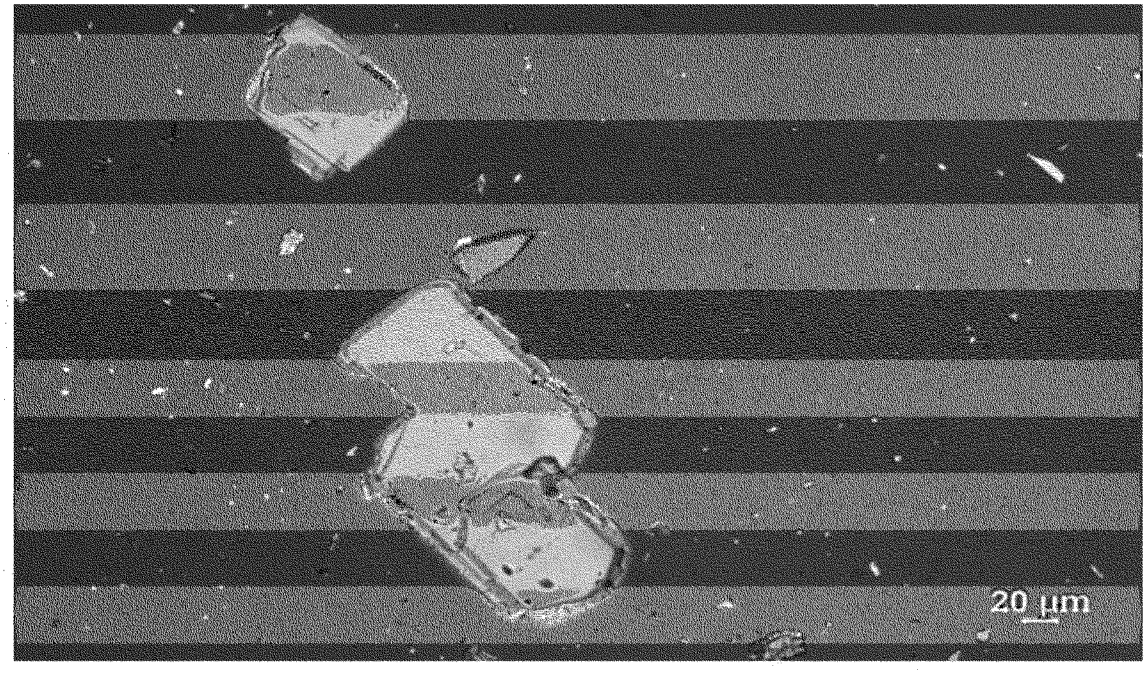
FIG. 31 shows a polarization microscopy image of Crystalline Form A prepared using a method not employing a seed crystal.
Figure 32:
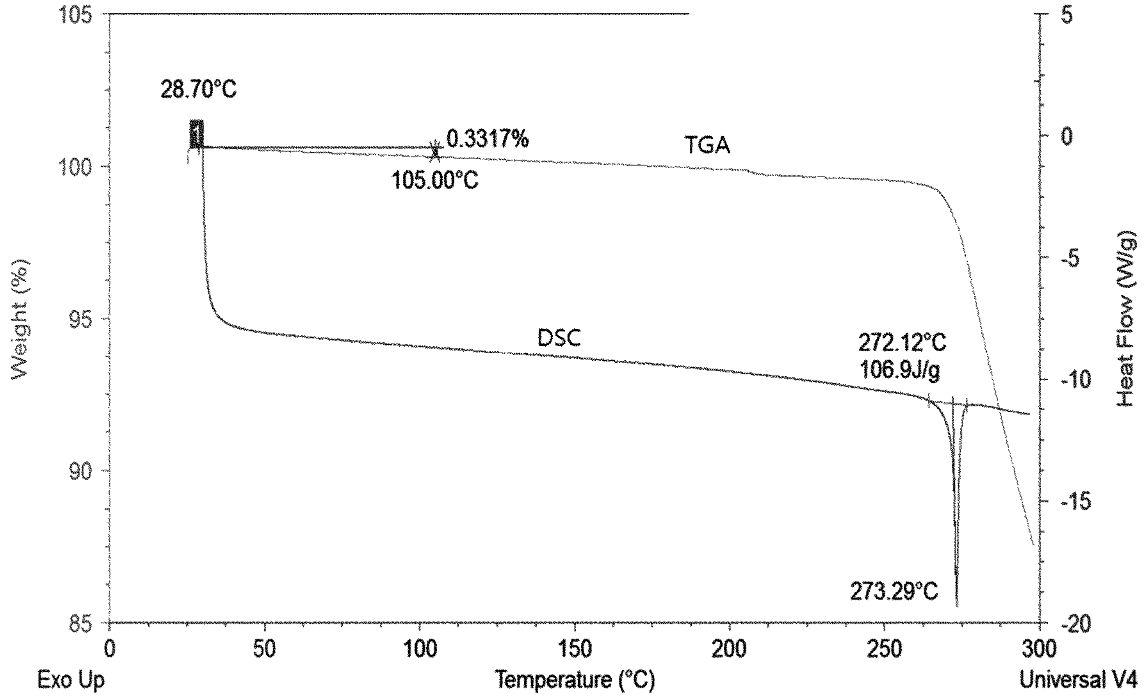
FIG. 32 shows TGA/DSC results of Crystalline Form A prepared using a method not employing a seed crystal.
Figure 33:
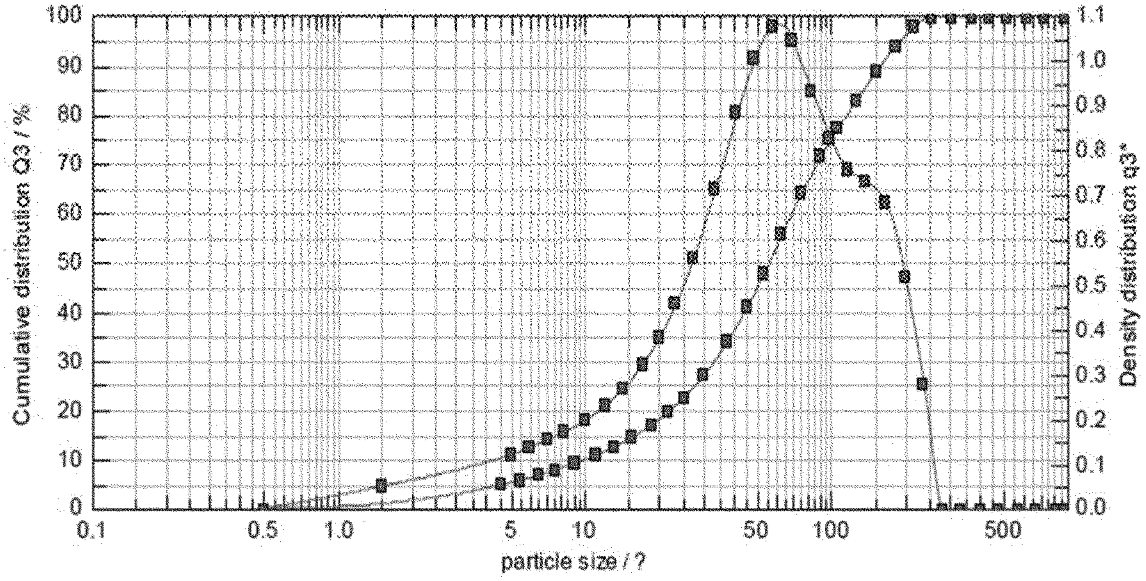
FIG. 33 shows a particle size distribution of Crystalline Form A prepared using a method not employing a seed crystal.

Table 22 shows a summary of recrystallization results for the compound of Chemical Formula 1 (2 g). Analyzing the XRPDs of the crystalline forms at each step showed that yield was around 5% less than that of Example 10 when a seed was not used. A laminated Crystalline Form A having a slightly green color was obtained. FIG. 28 shows a photograph of Crystalline Form A prepared using a method not employing a seed crystal, FIG. 29 shows XRPD analysis results of Crystalline Form A prepared using a method not employing a seed crystal, FIG. 30 shows HPLC chromatogram results for Crystalline Form A prepared using a method not employing a seed crystal, FIG. 31 shows a polarization microscopy image of Crystalline Form A prepared using a method not employing a seed crystal, FIG. 32 shows TGA/DSC results of Crystalline Form A prepared using a method not employing a seed crystal, and FIG. 33 shows a particle size distribution of Crystalline Form A prepared using a method not employing a seed crystal.

Summarizing the results of Examples 10, 12 and 13, Example 10 wherein DMSO:EtOH=1:7 was used appeared to be the best. To confirm reproducibility, the final step was carried out with 30 g of the compound of Chemical Formula 1 and the method using a seed crystal of Example 10.

Example 14: Final Method for Preparing Crystalline Form A (30 g Scale)

30 g of the compound of Chemical Formula 1 was added to 150 mL DMSO and dissolved at 75° C., then foreign materials were removed using a 0.45 μm membrane filter. Holding at 75° C., 600 mL EtOH was added (confirming that a clear solution was maintained in this state), and when 2% seed (Crystalline Form A) was added, a suspension started to be observed. Holding at 75° C., an additional 450 mL EtOH was added slowly over hours. All crystallization was carried out while agitating at 250 RPM. After adding all the EtOH, the mixture was cooled to 5° C. at a rate of 10° C./h. The solid generated was obtained using a 0.45 μm PTFE membrane filter, then vacuum dried for 15 hours at 50° C. As shown in Table 23, recrystallization of the compound of Chemical Formula 1 using a seed crystal exhibited a yield of 70.35% and purity of 99.96%.

Figure 34:
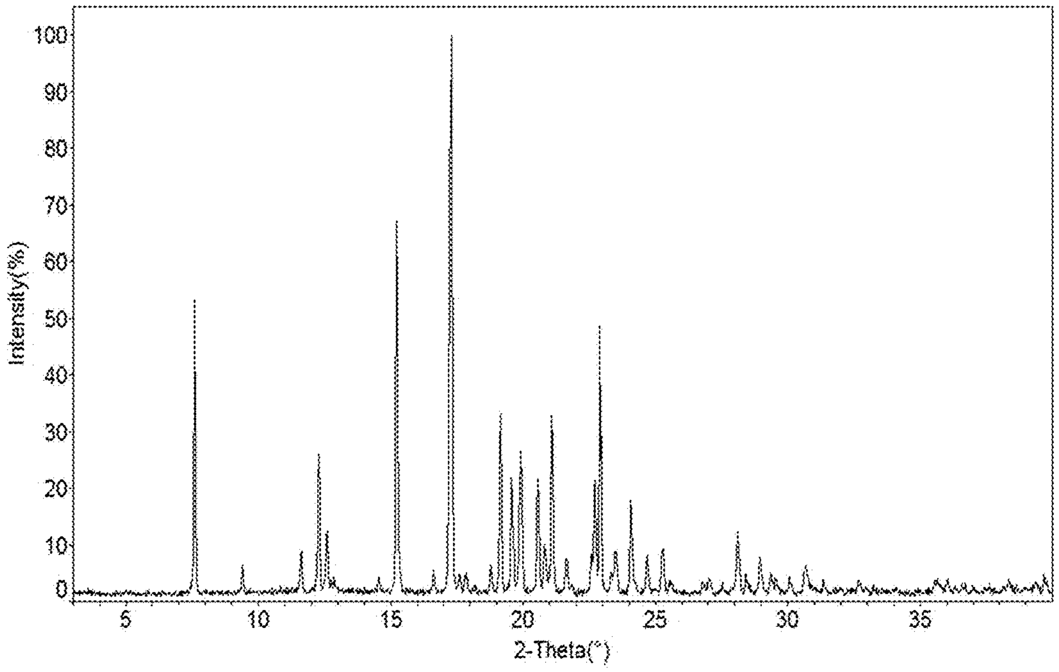
FIG. 34 shows XRPD analysis results for Crystalline Form A generated using the final preparation method.
Figure 35:
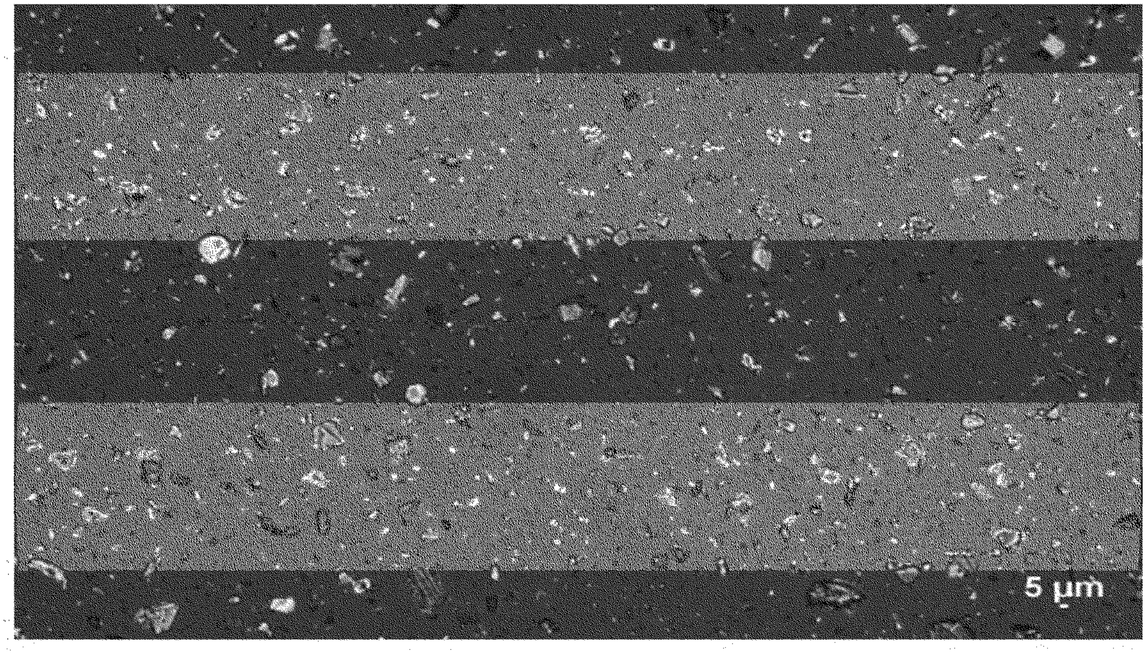
FIG. 35 shows a polarization microscopy (PLM) image of Crystalline Form A generated using the final preparation method.
Figure 36:
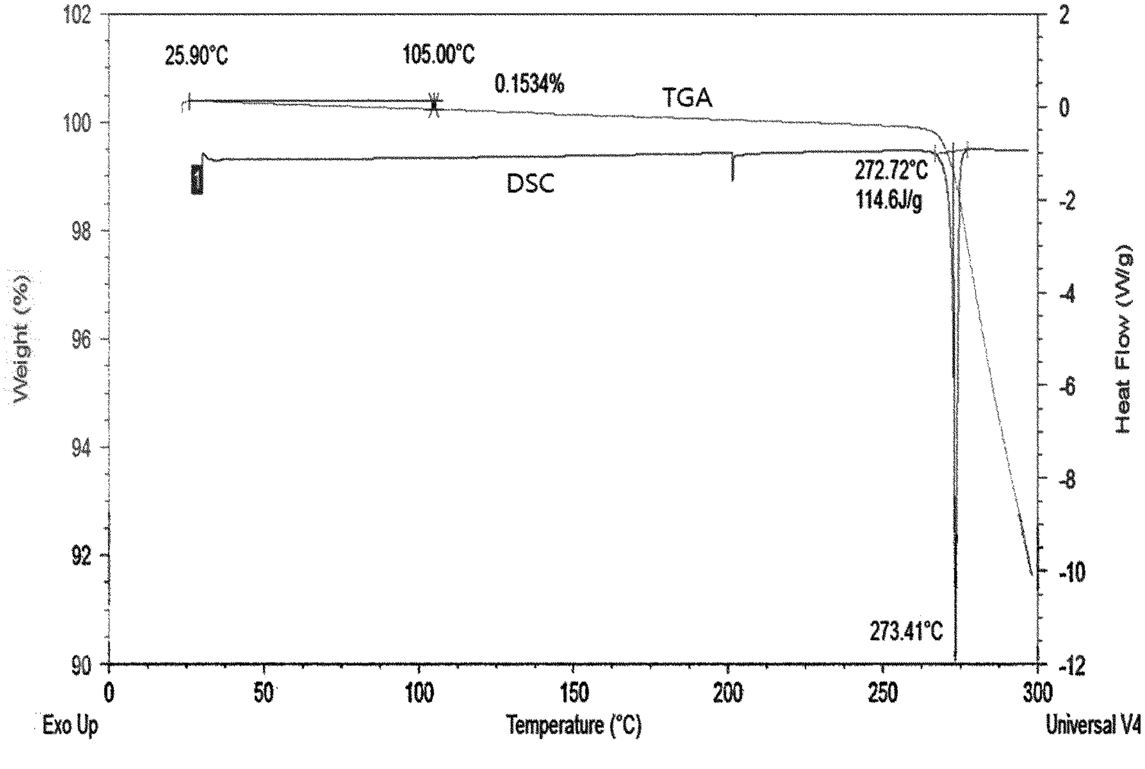
FIG. 36 shows TSA/DSC results for Crystalline Form A generated using the final preparation method.
Figure 37:
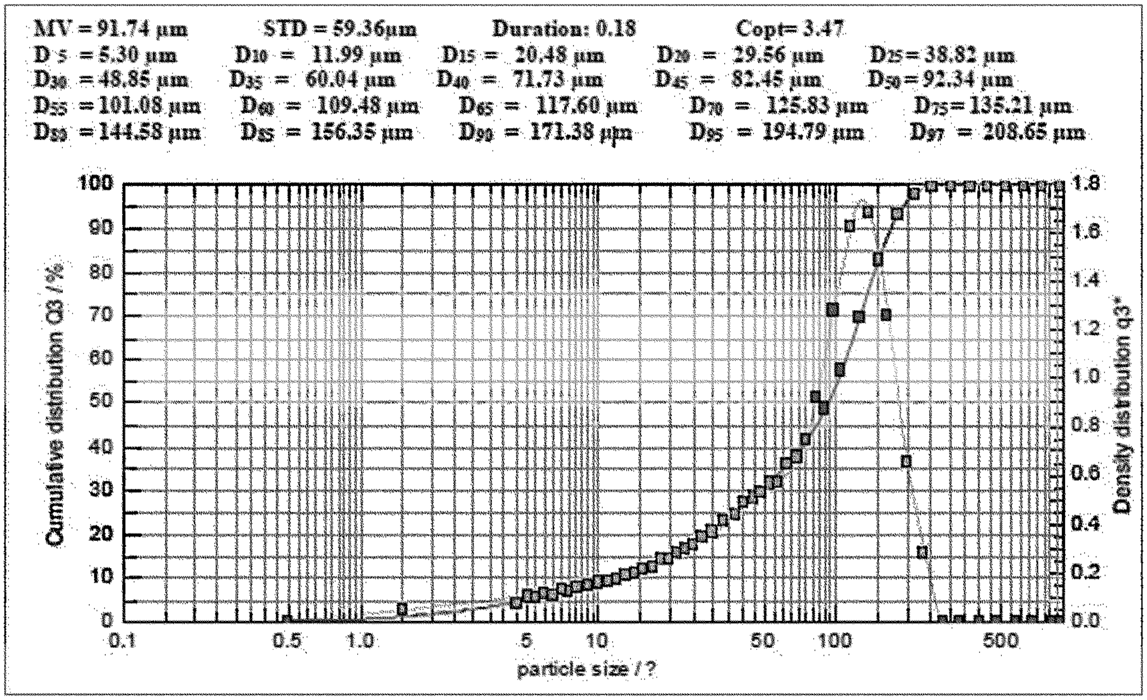
FIG. 37 shows a particle size distribution (PSD) of Crystalline Form A generated using the final preparation method.

Various analyses including XRPD, TSA/DSC, PLM, HPLC, PSM and residual solvent were carried out using the Crystalline Form A obtained here, and the results are shown in Tables 23 through 24 and FIG. 34 through 38. FIG. 34 shows XRPD analysis results for Crystalline Form A generated using the final preparation method, FIG. 35 shows a polarization microscopy (PLM) image of Crystalline Form A generated using the final preparation method, FIG. 36 shows TSA/DSC results for Crystalline Form A generated using the final preparation method, and FIG. 37 shows a particle size distribution (PSD) of Crystalline Form A generated using the final preparation method.

TABLE 23

Characterization of Crystalline Form A produced by final preparation method

| | |
|---|---|
| Method | Example 14: Final preparation method (30 g scale) |
| Appearance | White powder with slightly green |
| Initial XRPD | Pattern A |
| Intermediate products* | Pattern A |
| Final XRPD | Pattern A |
| Particle size | D10: 11.99 μm<br>D50: 92.34 μm<br>D90: 171.38 μm |
| DS Yield (%) | 70.35 |
| Residual solvent content | 0.07% (EtOH), 0.35% (DMSO) |
| Purity (%) | 99.96 |
| DSC | 273° C.; 114 J/g |
| TGA | 0.15%, <105° C. |
| PLM | Tabular shape |

Note:
large amount of solid generated when EtOH was added

The form of Crystalline Form A is characterized by a X-ray powder diffraction pattern comprising at least four diffraction peaks at 2[Θ] values (±0.2) selected from among 7.64, 12.32, 12.62, 15.26, 17.32, 19.18, 19.61, 19.95, 20.60, 21.12, 22.94, 24.11, and 28.15 at a temperature of 25±5° C.

TABLE 24

List of characteristic XRPD peaks of Crystalline Form A(Pattern A) produced by final preparation method

| 2-Theta(°) | Distance(Å) | Counts | Intensity % |
|---|---|---|---|
| 7.635 | 11.5699 | 1107 | 53.0 |
| 9.436 | 9.3652 | 101 | 4.8 |
| 11.653 | 7.5877 | 160 | 7.7 |
| 12.32 | 7.1787 | 518 | 24.8 |
| 12.62 | 7.0083 | 230 | 11.0 |
| 15.259 | 5.8018 | 1395 | 66.8 |
| 16.662 | 5.3164 | 79 | 3.8 |
| 17.316 | 5.1169 | 2089 | 100.0 |
| 17.631 | 5.0263 | 74 | 3.5 |
| 17.889 | 4.9542 | 68 | 3.3 |
| 18.816 | 4.7123 | 99 | 4.7 |
| 19.182 | 4.6231 | 672 | 32.2 |
| 19.613 | 4.5225 | 432 | 20.7 |
| 19.953 | 4.4461 | 532 | 25.5 |
| 20.596 | 4.3088 | 434 | 20.8 |
| 20.856 | 4.2556 | 182 | 8.7 |
| 21.121 | 4.2028 | 667 | 31.9 |
| 21.675 | 4.0967 | 129 | 6.2 |
| 22.753 | 3.9050 | 420 | 20.1 |
| 22.943 | 3.8731 | 1004 | 48.1 |
| 23.547 | 3.7751 | 159 | 7.6 |
| 24.108 | 3.6884 | 352 | 16.9 |
| 24.718 | 3.5988 | 141 | 6.7 |
| 25.342 | 3.5116 | 163 | 7.8 |
| 27.068 | 3.2915 | 59 | 2.8 |
| 28.146 | 3.1678 | 228 | 10.9 |
| 28.453 | 3.1344 | 81 | 3.9 |
| 28.992 | 3.0773 | 135 | 6.5 |
| 29.395 | 3.036 | 81 | 3.9 |
| 30.11 | 2.9655 | 64 | 3.1 |
| 30.721 | 2.9080 | 104 | 5.0 |

NMR Data of Pattern A $^1$H NMR (400 MHz, DMSO-$d_6$) δ ppm 1.40-1.54 (m, 2H), 2.06 (br d, J=11.04 Hz, 2H), 2.88 (br s, 4H), 3.09 (br d, J=4.52 Hz, 4H), 3.44-3.55 (m, 2H), 3.60-3.70 (m, 3H), 3.95 (br d, J=11.29 Hz, 2H), 5.35 (d, J=7.78 Hz, 1H), 6.32 (s, 1H) 6.76 (s, 2H), 7.24-7.36 (m, 1H), 7.48 (t, J=7.78 Hz, 2H), 7.80 (d, J=7.28 Hz, 2H), 10.93 (s, 1H).

Water Sorption and Desorption Study, DVS Cycle

Figure 38:
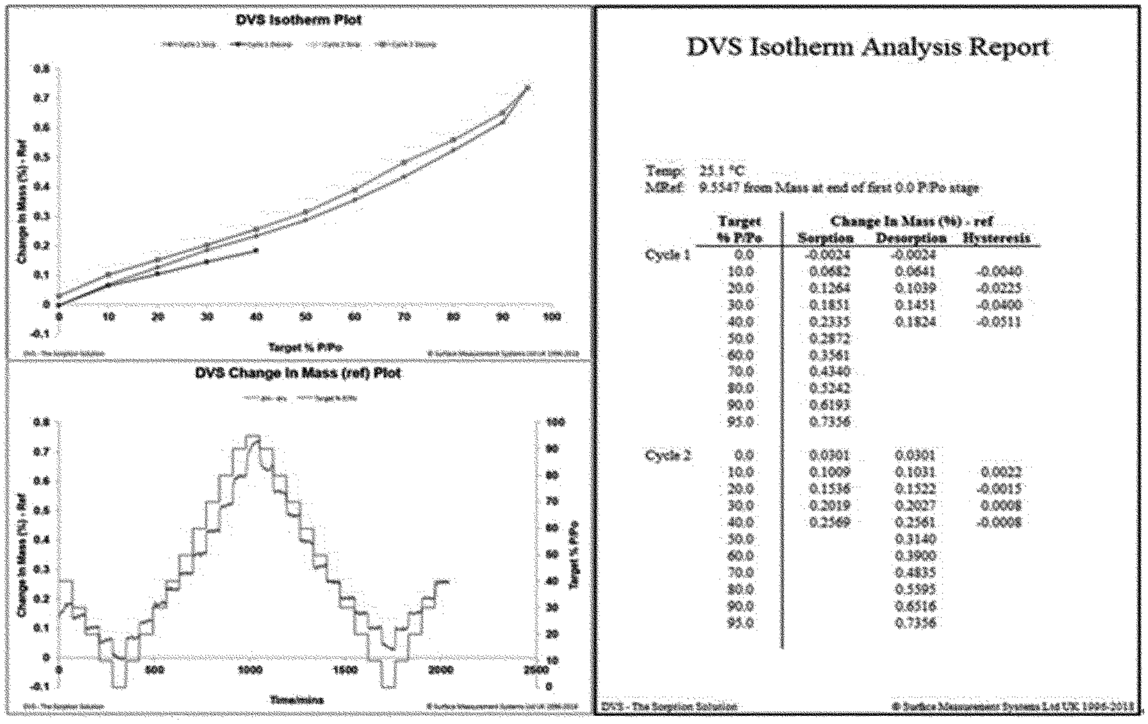
FIG. 38 shows moisture sorption and desorption isotherm analysis results for Crystalline Form A.

Using SMS DVS Advantage 1, 10 mg of Crystalline Form A was placed in a mesh stainless steel basket. The overall test cycle comprises scanning two times (sorption and desorption) at 10% RH intervals in a 40 to 90% range (60 to 360 minutes for each humidity level) at a constant temperature (25° C.). Approximately 0.7% weight increase and absorption and loss relative to sorption level indicates a non-hygroscopic sample. FIG. 38 is an isotherm curve for Crystalline Form A (weight change % v. RH %), and a kinetic curve of weight change % v. time and relative humidity %. XRPD analysis after DVS shows no change in crystalline form, and this appears to be the most stable crystalline form.

Example 15: Evaluating the Suitability of Crystalline Form A for Formulation

Example 15-1. Pressurization Test for Crystalline Form A 100 mg of Crystalline Form A was placed in a die cavity, then made into tablets by pressing for 3 minutes each at pressures of 2, 3 and 4 MPa using an upper punch. XRPD analysis after grinding the respective tablets showed no changes, and this appears to be the most stable crystalline form.

Example 15-2. Grinding Test for Crystalline Form A

1) Dry Grinding 30 mg Crystalline Form A was manually ground for 5 minutes in a mortar and pestle. XRPD analysis results showed no change.

2) Wet Grinding in EtOH 30 mg of Crystalline Form A and 40 mL of EtOH were placed in a mortar and pestle, and manually ground for 5 minutes. XRPD analysis results showed no change.

3) Wet Grinding in $H_2O$ 30 mg of Crystalline Form A and 40 mL of $H_2O$ were placed in a mortar and pestle, and manually ground for 5 minutes. XRPD analysis results showed no change.

Figure 39:
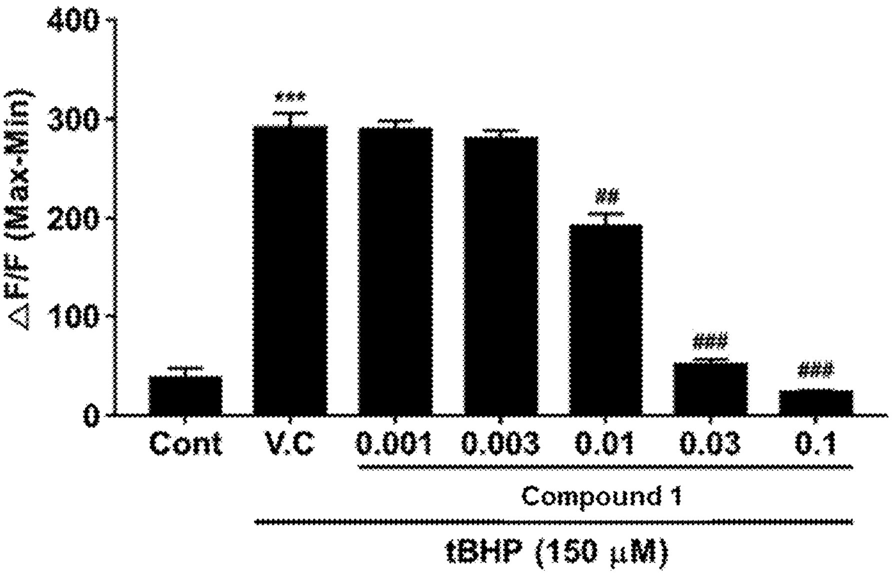
FIG. 39 shows the calcium concentration regulation effect of the compound of Chemical Formula 1 under tBHP treatment conditions.

Example 16: Effect of Maintaining Homeostasis of Cytoplasmic and Mitochondrial Calcium Concentration in Cardiomyocytes To examine the calcium concentration maintenance effect in cardiomyocytes, H9C2 cells were placed in a 96 well plate at $1.5 \times 10^4$ cells/well and cultured for 24 hours. To measure cytoplasmic calcium concentration, a FLIPR Calcium 6 assay kit (Molecular devices; #R8190) was used. Following the manufacturer's experimental method, the cells were treated with probenecid and calcium-specific dye. After 1.75 hours, the cells were treated for 0.25 hours so that the final concentration of the compound of Chemical Formula 1 was 0.1, 0.03, 0.01, 0.03, and 0.001 μM. For stimulation of cells, the cells were treated with tBHP to a final concentration of 150 μM, then cytoplasmic calcium concentration was measured every 30 seconds in real time. FIG. 39 shows the calcium concentration regulation effect of the compound of Chemical Formula 1 under tBHP treatment conditions. The ΔF/F (Max-Min) value of the vertical axis is the difference between the maximum and minimum values for the fluorescence value of calcium-specific dye after tBHP treatment. The ΔF/F value increases with cytoplasmic calcium concentration. The horizontal axis indicates the concentration of Chemical Formula 1, and V.C. is a control only treated with the vehicle, where cytoplasmic calcium concentration increases most when treated with tBHP. In the case where the cells were treated with 0.01 μM of the compound of Chemical Formula 1, the abnormally increased cytoplasmic calcium concentration caused by tBHP treatment was reduced, and under 0.1 μM treatment, normal level of cytoplasmic calcium concentration was exhibited.

Figure 40:
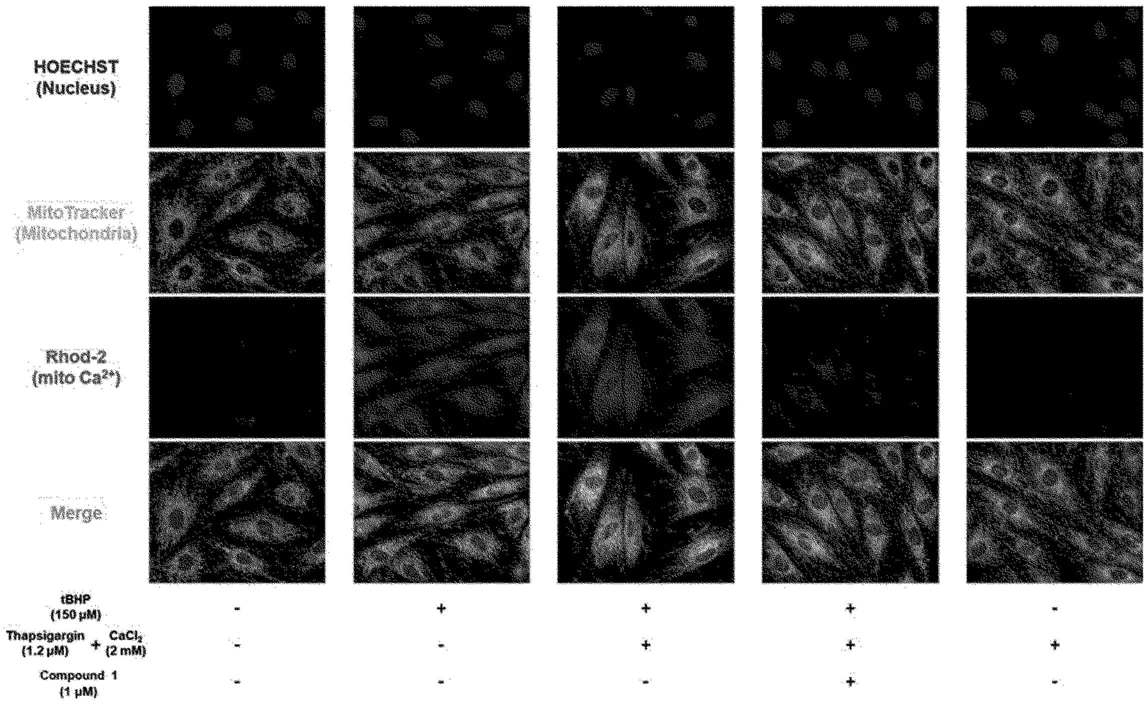
FIG. 40 shows imaging results relating to the regulating effect of mitochondrial calcium concentration of the compound of Chemical Formula 1 in the condition of additional treatment with thapsigargin and CaCl2 in addition to tBHP.

In addition, in order to confirm the effect of inhibiting the increase in mitochondrial calcium concentration in cardiomyocytes by cell imaging, H9C2 cells were seeded in a 35 mm culture dish at $1.5 \times 10^4$ cells and cultured for 24 hours. Imaging of calcium concentration in mitochondria was performed using Rhod-2. The cells were treated with Rhod-2, MitoTracker Green (200 nM), and Hoechst33342 (2 drops/ml) for 50 minutes, washed twice with KRB buffer, and incubated for another 30 minutes with buffer solution. The cells were treated with the compound of Formula 1 for 0.25 hours to final concentration of 10 μM, and treated with tBHP for 30 minutes to final concentration of 150 μM. Then, the cells were treated with 1.2 μM thapsigargin for 10 minutes and 2 mM of $CaCl_2$, and the fluorescence developed in mitochondrial calcium of the living cells was observed through imaging. FIG. 40 shows imaging results related to the effect of inhibiting the increase in mitochondrial calcium of the compound of Formula 1 under the conditions of additional treatment with thapsigargin and $CaCl_2$ in addition to tBHP. As a result of the experiment, it was observed through a decrease in Rhod-2 fluorescence that the compound of Formula 1 effectively inhibited the increase in the calcium concentration in mitochondria that occurred under the conditions of additional treatment with tBHP, thapsigargin and $CaCl_2$. Through this result, it was confirmed that the compound of Chemical Formula 1 strongly inhibits increasing calcium in mitochondria.

The results of this experiment are expected to show prevention, treatment and improvement effects on diseases related to the mechanism of improving ER stress and mitochondrial dysfunction through the function of intracellular calcium regulation.

Figure 41:
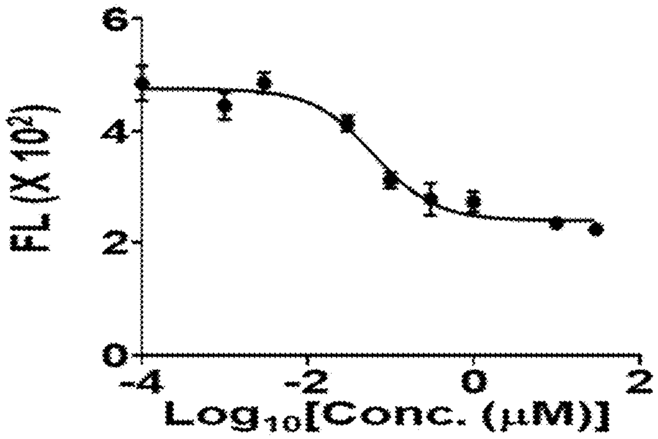
FIG. 41 shows the intra-mitochondrial reactive oxygen species removal effect of the compound of Chemical Formula 1 under tBHP treatment conditions.

Example 17: Intra-Mitochondrial Reactive Oxygen Species Removal Effect in Cardiomyocytes To examine the intra-mitochondrial reactive oxygen species removal effect in cardiomyocytes, H9C2 cells were placed in a 96 well plate at $1.5 \times 10^4$ cells/well and cultured for 24 hours. To measure mitochondria-specific reactive oxygen species, fluorometry using dihydrorhodamine-123 (DHR-123) was used. After treating the cells with DHR-123 0.5 hours ahead, the cells were treated with the compound of Chemical Formula 1 for 0.25 hours to final concentrations of 0.0001, 0.001, 0.003, 0.03, 0.1, 0.3, 1, 10 and 30 μM. tBHP was added to the cells to a final concentration of 400 μM, and intracellular reactive oxygen species were measured every 3 minutes in real time through intensity of fluorescence. FIG. 41 shows the intra-mitochondrial reactive oxygen species removal effect of the compound of Chemical Formula 1 under tBHP treatment conditions. The horizontal axis represents the concentration of Chemical Formula 1 on a log scale, and the vertical axis represents the total amount of intra-mitochondrial reactive oxygen species occurring over 2 hours following tBHP treatment. Whereas intra-mitochondrial reactive oxygen species increased drastically due to tBHP treatment, treatment with the compound of Chemical Formula 1 was observed to inhibit occurrence of reactive oxygen species in a concentration-dependent manner.

Figure 42:
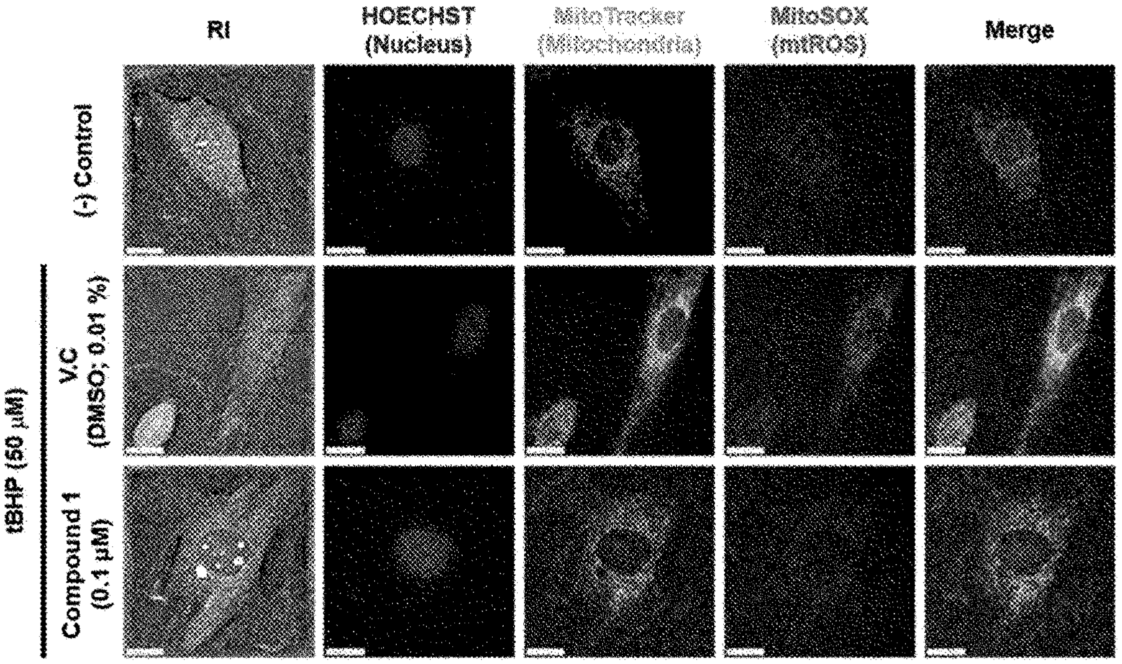
FIG. 42 shows imaging results relating to the intra-mitochondrial superoxide removal effect of the compound of Chemical Formula 1 under tBHP treatment conditions.

To confirm the reactive oxygen species removal effect of the compound of Chemical Formula 1 through cell imaging, H9C2 cells were placed in a 35 mm confocal microscope culture plate at $1.5 \times 10^4$ cells and cultured for 24 hours. To measure the superoxides among the reactive oxygen species occurring in mitochondria, intracellular fluorescent imaging was used by using MitoSOX™ (Red Mitochondrial Superoxide Indicator). The cells were pretreated for 0.25 hours with the compound of Chemical Formula 1 to a concentration of 1 μM, then tBHP was added to the cells to a final concentration of 50 μM, then treated for 1 hour. The cell culture medium was replaced with a medium without phenol red, then the cells were treated for 30 minutes with HOECHST (0.5 drop/ml), MitoTracker Green (150 nM) and MitoSOX (2 μM) before observing intracellular fluorescence through imaging. FIG. 42 shows imaging results relating to the intra-mitochondrial superoxide removal effect of the compound of Chemical Formula 1 under tBHP treatment conditions. The result of the experiment, it was observed through reduction of fluorescence when the compound of Chemical Formula 1 was treated with MitoSOX that the compound of Chemical Formula 1 effectively removes intra-mitochondrial reactive oxygen species including superoxides, and thereby it was confirmed that Chemical Formula 1 acts as a powerful antioxidant that potently removes reactive oxygen species occurring in mitochondria.

The effect of removing reactive oxygen species in mitochondria shown in the above experiment is related to cell necrosis, thus it is expected to show prevention, treatment, and improvement effects on cell damage and diseases related to necrosis.

Figure 43:
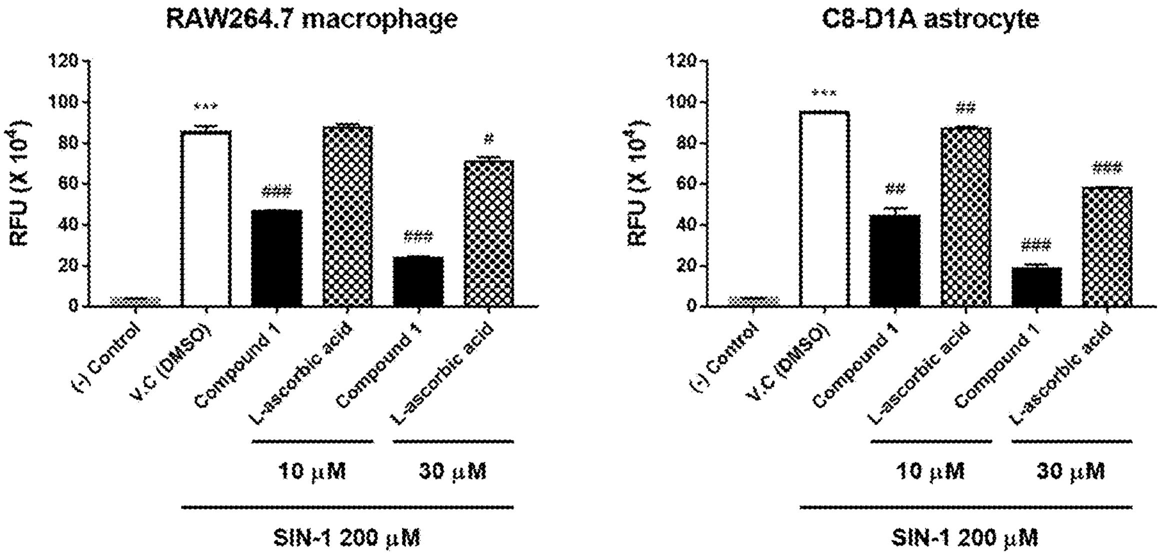
FIG. 43 shows the intracellular peroxynitrite removal effect of the compound of Chemical Formula 1 under SIN-1 treatment conditions.

Example 18: Effect of Removing Peroxynitrite Produced in Macrophages and Astrocytes To confirm the effect of removing peroxynitrite produced from macrophages, RAW264.7 cells were seeded in a 96 well plate at $1 \times 10^5$ cells/well and cultured for 24 hours. Peroxynitrite was measured by fluorescence measurement using DAX-J2™ PON Green dye. After pretreating the cells with DAX-J2™ PON Green dye for 1 hour, the cells were treated with the compound of Chemical Formula 1 and ascorbic acid as a positive control to a final concentration of 10 μM and 30 μM, respectively, for 5 minutes. Thereafter, SIN-1 was treated to a final concentration of 200 μM, and the amount of peroxynitrite generated in the cell every 2 minutes in real time was measured through fluorescence intensity. To confirm the effect of removing peroxynitrite from astrocytes, C8-D1A cells were seeded in a 96 well plate at $6\times10^4$ cells/well and cultured for 24 hours, and the experiment was performed under the same conditions. FIG. 43 shows the intracellular peroxynitrite removal effect of the compound of Formula 1 under SIN-1 treatment conditions. In the figure, the results showed macrophages on the left and astrocyte on the right. The horizontal axis represents the concentrations of the compound of Formula 1 and ascorbic acid, and V.C is the control treated with only the vehicle, and the concentration of intracellular peroxynitrite increases the most during SIN-1 treatment. The vertical axis represents the total amount of peroxynitrite generated 1 hour after SIN-1 treatment. Although intracellular peroxynitrite was rapidly increased by SIN-1, peroxynitrite generation was inhibited by treatment with the compound of Formula 1 in a concentration-dependent manner, and exhibited a superior inhibitory effect than ascorbic acid, a positive control.

The results of this experiment were confirmed by confirming the peroxynitrite removal effect of the compound of Chemical Formula 1 in macrophages and astrocytes involved in inflammation. It is expected to show prevention, treatment and improvement effects on various inflammatory-based diseases such as pancreatitis, rheumatoid arthritis, degenerative arthritis, bacterial and viral infections, glomerulonephritis, acute/chronic kidney disease, necrotizing colitis, pneumonia, hepatitis, mucositis, etc., and aging and neurodegenerative diseases such as Alzheimer's disease, Parkinson's disease, amyotrophic lateral sclerosis, Limb gridle/Becker muscular dystrophy, and Duchenne muscular atrophy, etc.

Figure 44:
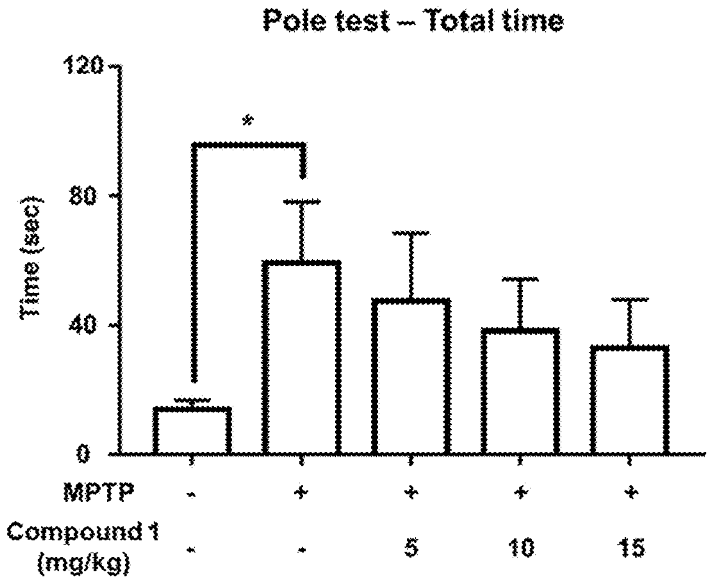
FIG. 44 shows the effect of improving the total time upon treatment with the compound of Chemical Formula 1 in MPTP-induced Parkinson's disease mouse model.
Figure 45:
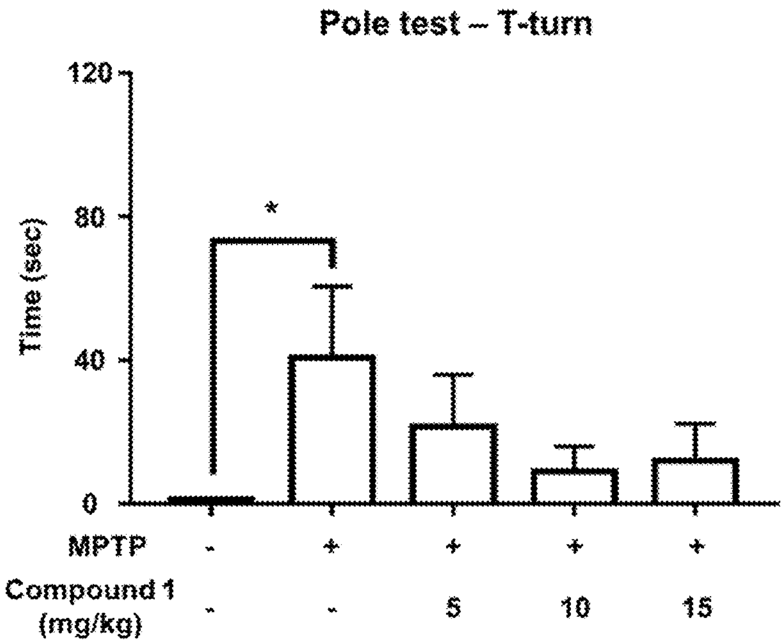
FIG. 45 shows the T-turn improvement effect upon treatment with the compound of Chemical Formula 1 in MPTP-induced Parkinson's disease mouse model.

Example 19: Motor Performance Improvement Effect in MPTP-Induced Parkinson's Disease Mouse Model MPTP (1-Methyl-4-phenyl-1,2,3,6-tetrahydropyridine) is a pro-drug of the neurotoxin MPP+(1-methyl-4-phenylpyridinium). When administered, it destroys dopaminergic neurons and causes symptoms of Parkinson's disease. Behavioral disorders were induced by administering 20 mg/kg MPTP to C57BL/6 mice a total of 4 times at 2 hour intervals. The compound of Chemical Formula 1 was administered intraperitoneally once a day at low, medium and high doses for 6 days from 2 days after MPTP administration. The pole test was performed to confirm the effect of improving the motor performance of the compound of Formula 1. FIG. 44 shows the effect of improving the Total time when treating the compound of Formula 1 in the MPTP-induced Parkinson's disease mouse model, and FIG. 45 shows the T-turn improvement effect when the compound of Formula 1 is treated in the MPTP-induced Parkinson's disease mouse model. Total time and T-turn values of the MPTP administration group were significantly increased compared to the control group. At this time, it was confirmed that the total time and T-turn time were recovered in a concentration-dependent manner in the group to which the compound of Formula 1 was administered.

Figure 46:
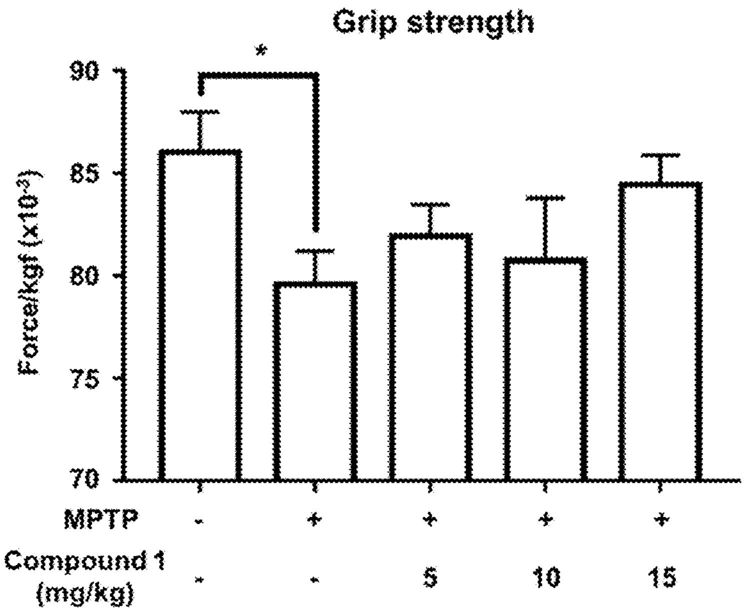
FIG. 46 shows the effect of improving grip strength upon treatment with the compound of Chemical Formula 1 in MPTP-induced Parkinson's disease mouse model.

In addition, a grip strength test was performed to confirm the motor performance improvement effect of the compound of Formula 1. FIG. 46 shows the effect of improving grip strength when treated with the compound of Formula 1 in an MPTP-induced Parkinson's disease mouse model. The grip force value of the MPTP-administered group was significantly reduced compared to the control group. At this time, it was confirmed that the grip force value in the group administered with the compound of Formula 1 was restored in a concentration-dependent manner.

Figure 47:
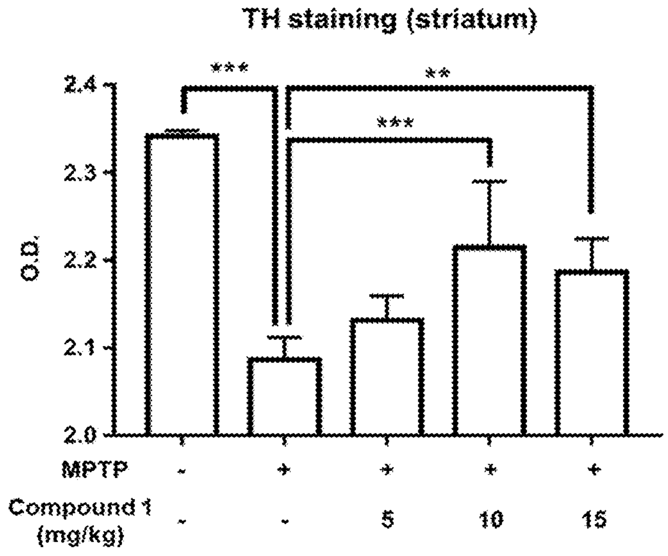
FIG. 47 shows the effect of restoring TH levels in the striatum upon treatment with the compound of Chemical Formula 1 in MPTP-induced Parkinson's disease mouse model.
Figure 48:
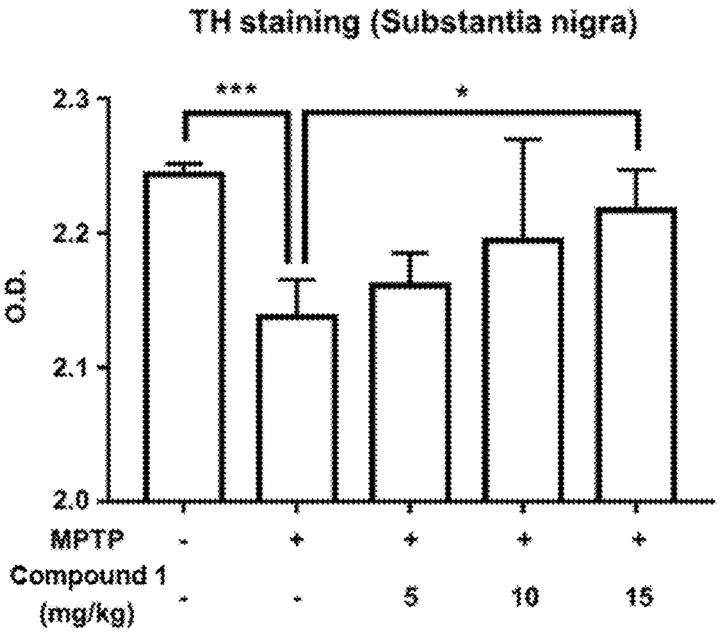
FIG. 48 shows the effect of restoring TH levels in the substantia nigra upon treatment with the compound of Chemical Formula 1 in an MPTP-induced Parkinson's disease mouse model.

Example 20: Dopaminergic Neuron Protective Effect in MPTP-Induced Parkinson's Disease Mouse Model Behavioral disorders were induced by administering 20 mg/kg MPTP to C57BL/6 mice a total of 4 times at 2 hour intervals. The compound of Chemical Formula 1 was administered intraperitoneally once a day at low, medium and high doses for 6 days from 2 days after MPTP administration. On the 6th day after administration of the compound of Formula 1, mice were sacrificed, frozen sections of brain tissue were prepared, and TH (Tyrosine hydroxylase) staining was performed. FIG. 47 shows the effect of restoring TH levels in the striatum when the compound of Chemical Formula 1 is treated in a mouse model of MPTP-induced Parkinson's disease. In the striatum, the TH level of the MPTP-administered group was significantly reduced compared to the control group. At this time, the TH level was recovered in a concentration-dependent manner in the group administered with the compound of Formula 1, and significantly increased at the medium and high doses. FIG. 48 shows the effect of restoring TH levels in the substantia nigra when the compound of Chemical Formula 1 is treated in an MPTP-induced Parkinson's disease mouse model. In the substantia nigra, the TH level of the MPTP-administered group was significantly reduced compared to the control group. At this time, in the group administered with the compound of Chemical Formula 1, the TH level was recovered in a concentration-dependent manner, and there was a significant difference at the high dose.

The invention claimed is:

1. A Crystalline Form A of a compound of Chemical Formula 1,

[Chemical Formula 1]

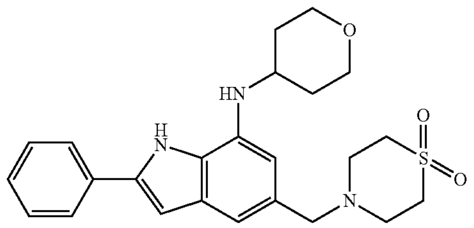

wherein the crystalline form is identified with an X-ray powder diffraction pattern having at least 4 diffraction peaks selected from 2[Θ] values 7.64±0.2, 12.32±0.2, 12.62±0.2, 15.26±0.2, 17.32±0.2, 19.18±0.2, 19.61±0.2, 19.95±0.2, 20.60±0.2, 21.12±0.2, 22.94±0.2, 24.11±0.2, and 28.15=0.2.

2. A solid pharmaceutical composition comprising the Crystalline Form A of the compound of Chemical Formula 1 according to claim 1, and a pharmaceutically acceptable carrier.

3. A method for preparing Crystalline Form A of a compound represented by Chemical Formula 1 according to claim 1, the method comprising:

a step of crystallizing by adding an anti-solvent in a solution obtained by dissolving the compound of Chemical Formula 1 in a solvent, wherein the solvent is selected from DMSO, DMF or NMP, and the anti-solvent is ethanol or MTBE; and a step of growing crystals by cooling the solution over 6 to 48 hours to 0 to 25° C. while stirring

[Chemical Formula 1]

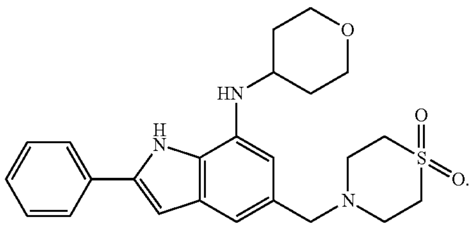

4. The method according to claim 3 for preparing Crystalline Form A of a compound represented by Chemical Formula 1 the method further comprising, in the step of adding the anti-solvent, adding a Crystalline Form A of the compound of Chemical Formula 1 as a seed crystal.

5. The method according to claim 3 for preparing Crystalline Form A of a compound represented by Chemical Formula 1, wherein the weight of solvent is at least 2 times the weight of the compound of Chemical Formula 1.

6. The method according to claim 3 for preparing Crystalline Form A of a compound represented by Chemical Formula 1, wherein the weight of anti-solvent is at least 2 times the weight of the solvent.

* * * * *